(12) United States Patent
Maggard, Jr. et al.

(10) Patent No.: US 11,819,702 B2
(45) Date of Patent: Nov. 21, 2023

(54) PEROVSKITE MATERIALS AND METHODS OF MAKING AND USE THEREOF

(71) Applicant: NORTH CAROLINA STATE UNIVERSITY, Raleigh, NC (US)

(72) Inventors: Paul A. Maggard, Jr., Raleigh, NC (US); Shaun O'Donnell, Raleigh, NC (US); Jacob L. Jones, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 254 days.

(21) Appl. No.: 17/192,022

(22) Filed: Mar. 4, 2021

(65) Prior Publication Data

US 2021/0275821 A1    Sep. 9, 2021

Related U.S. Application Data

(60) Provisional application No. 62/984,943, filed on Mar. 4, 2020.

(51) Int. Cl.
*A61N 1/378*     (2006.01)
*B01J 23/02*     (2006.01)
(Continued)

(52) U.S. Cl.
CPC ............ *A61N 1/378* (2013.01); *B01J 23/002* (2013.01); *B01J 23/02* (2013.01); *B01J 23/14* (2013.01); *B01J 35/004* (2013.01); *C01B 3/042* (2013.01); *C01G 25/006* (2013.01); *H10N 30/8536* (2023.02); *C01P 2002/34* (2013.01); *C01P 2002/50* (2013.01); *C01P 2002/72* (2013.01); *C01P 2002/76* (2013.01); *C01P 2002/77* (2013.01); *C01P 2002/84* (2013.01); *C01P 2002/85* (2013.01); *C01P 2002/90* (2013.01); *C01P 2006/40* (2013.01)

(58) Field of Classification Search
CPC ....... A61N 1/378; B01J 23/002; B01J 35/004; C01B 3/042; C01G 25/006; H01L 41/1871; H01L 41/1876; C01P 2022/34; C01P 2006/40
See application file for complete search history.

(56) References Cited

U.S. PATENT DOCUMENTS 8,043,987 B2    10/2011   Chen et al.
8,179,025 B1    5/2012    Takeuchi et al.
(Continued)

FOREIGN PATENT DOCUMENTS

CN    10678008      * 12/2016
CN    107651957     * 2/2018
(Continued)

OTHER PUBLICATIONS

Kresse et al, "Efficient interative schemes for ab initio total-energy calculcations using a plane-wave basis set", Phys Rev B, vol. 54 , No. 16, Oct. 15, 98, pp. II 169-II 186.*
(Continued)

*Primary Examiner* — C Melissa Koslow
(74) *Attorney, Agent, or Firm* — Meunier Carlin & Curfman LLC

(57) ABSTRACT

Disclosed herein are perovskite materials and methods of making an use thereof.

19 Claims, 40 Drawing Sheets
(22 of 40 Drawing Sheet(s) Filed in Color)

(51) Int. Cl.

| | | |
|---|---|---|
| B01J 23/14 | (2006.01) | |
| B01J 23/00 | (2006.01) | |
| B01J 35/00 | (2006.01) | |
| C01B 3/04 | (2006.01) | |
| C01G 25/00 | (2006.01) | |
| H10N 30/853 | (2023.01) | |

(56) References Cited

U.S. PATENT DOCUMENTS

| | | | |
|---|---|---|---|
| 9,773,967 B2 | 9/2017 | Maurya et al. | |
| 2009/0207551 A1* | 8/2009 | Suzuki | C04B 35/49 |
| | | | 501/137 |
| 2009/0291324 A1* | 11/2009 | Cohen | C04B 35/472 |
| | | | 423/598 |

FOREIGN PATENT DOCUMENTS

| | | | |
|---|---|---|---|
| JP | 2010-215435 | * | 9/2010 |
| JP | 2012-206864 | * | 10/2012 |
| WO | WO 2005/075377 | * | 8/2005 |

OTHER PUBLICATIONS

Suzuki et al, "Effects of Sn2+ Ion Size on Sn Doped SrTiO3", Jpn. J. Appl. Phys., 52, 52, 09KC04,(2013), pp. 09KC04-1 to 09KC04-3, Sep. 20, 2013.*

Diehl et al, "Structure-Directing Lone Pairs: Synthesis and Structural Characterization of SnTiO3", Chem. Mater., 2018, 30, pp. 8932-8938. Nov. 28, 2018.*

Aksel E et al. Local Atomic Structure Deviation from Average Structure of Na0.5Bi0.5TiO3: Combined x-Ray and Neutron Total Scattering Study. Phys. Rev. B—Condens. Matter Mater. Phys. 2013, 87 (10), 1-10.

Aykol M et al. Thermodynamic Limit for Synthesis of Metastable Inorganic Materials. Sci. Adv. 2018, 4, eaaq0148.

Boltersdorf et al. Single- and Double-Site Substitutions in Mixed-Metal Oxides: Adjusting the Band Edges Toward the Water Redox Couples. J. Phys. Chem. C 2016, 120 (34), 19175-19188.

Boltersdorf J et al. Flux Synthesis, Optical and Photocatalytic Properties of n-Type Sn2TiO4: Hydrogen and Oxygen Evolution Under Visible Light. Chem. Mater. 2017, 28, 8876-8889.

Boltersdorf J et al. Flux-mediated Crystal Growth of Metal Oxides: Synthetic Tunability of Particle Morphologies, Sizes, and Surface Features for Photocatalysis Research. CrystEngComm, 2015, 17, 2225-2241.

Boltersdorf J et al. Synthesis and Optical Properties of Ag(I), Pb(II), and Bi(III) Tantalate-Based Photocatalysts. ACS Catal. 2013, 3, 2943-2953.

Campo CM et al. Thermal Behaviour of Romarchite Phase SnO in Different Atmospheres: A Hypothesis about the Phase Transformation. Heliyon 2016, 2 (5), e00112.

Choi J et al. Metastable Cu(I)-Niobate Semiconductor with a Low-Temperature Nanoparticle-Mediated Synthesis. ACS Nano 2013, 7(2), 1699-1708.

Diehl L et al. Structure-Directing Lone Pairs: Synthesis and Structural Characterization of SnTiO3. Chem. Mater. 2018, 30 (24), 8932-8938.

Emery AA et al. Data descriptor: High-Throughput DFT Calculations of Formation Energy, Stability and Oxygen Vacancy Formation Energy of ABO3 Perovskites Scient. Data 2017, 4, 170153.

Gardner J et al. Tin Titanate—the Hunt for a New Ferroelectric Perovskite. Reports Prog. Phys. 2019, 82, 092501.

Gauzzi F et al. X-Ray Diffraction and Mössbauer Analyses of SnO Disproportionation Products. Inorganica Chim. Acta 1985, 104 (1), 1-7.

Goudochnikov P et al. Correlations Between Transition Temperature, Tolerance Factor and Cohesive Energy in 2+:4+ Perovskites. J. Phys.: Condens. Matter 2007, 19, 176201.

Ha VA et al. Structural Design Principles for Low Hole Effective Mass s-Orbital-Based p-Type Oxides. J. Mater. Chem. C 2017, 5 (23), 5772-5779.

Hautier G et al. Accuracy of Density Functional Theory in Predicting Formation Energies of Ternary Oxides from Binary Oxides and its Implication on Phase Stability. Phys. Rev. B—Condens. Matter Mater. Phys. 2012, 85, 155028.

Kato H et al. Construction of Z-scheme type heterogeneous photocatalysis systems for water splitting into H2 and O2 under visible-light irradiation. Chem. Lett. 2004, 33, 1348-1349.

King N et al. Synthesis, Structure and Thermal Instability of the Cu2Ta4O11 Phase. Cryst. Grow. Des. 2015, 15, 552-558.

Kirkpatrick S. Percolation and Conduction. Rev. Mod. Phys. 1973, 45, 574.

Lu B et al. "Ultra-flexible piezoelectric devices integrated with heart to harvest the biomechanical energy", Scientific Reports 2015, 5, 16065.

Martinolich AJ et al. Circumventing Diffusion in Kinetically Controlled Solid-State Metathesis Reactions. J. Am. Chem. Soc. 2016, 138 (34), 11031-11037.

Matar SF et al. First Principles Studies of SnTiO3 Perovskite as Potential Environmentally Benign Ferroelectric Material. Chem. Phys. 2009, 355 (1), 43-49.

McLamb N et al. Flux Growth of Single-Crystal Na2Ta4O11 Particles and their Photocatalytic Hydrogen Production. Cryst. Growth Des. 2013, 13, 2322-2326.

Nishiro R et al. A CoOx-modified SnNb2O6 photoelectrode for highly efficient oxygen evolution from water. ChemCommun. 2017, 53, 629-632.

Noureldine D et al. State-of-the-Art Sn2+-Based Ternary Oxides as Photocatalysts for Water Splitting: Electronic Structures and Optoelectronic Properties. Catal. Sci. Technol. 2016, 6 (21), 7656-7670.

O'Donnell S et al. Fast Flux Reaction Approach for the Preparation of Sn2TiO4: Tuning Particle Sizes and Photocatalytic Properties. J. Electrochem. Soc. 2019, 166 (5), H3084-H3090.

Palasyuk O et al. Site-Differentiated Solid Solution in (Na1—xCux)2Ta4O11 and its Electronic Structure and Optical Properties. Inorg. Chem. 2010, 49 (22), 10571-10578.

Parker WD et al. First-Principles Study of Misfit Strain-Stabilized Ferroelectric SnTiO3. Phys. Rev. B—Condens. Matter Mater. Phys. 2011, 84 (24), 1-7.

Perdew J et al. Generalized Gradient Approximation Made Simple. Phys. Rev. Lett. 1996, 77, 3865.

Pitike KC et al. First-Principles Studies of Lone-Pair-Induced Distortions in Epitaxial Phases of Perovskite SnTiO3 and PbTiO3. Phys. Rev. B—Condens. Matter Mater. Phys. 2015, 91 (3), 1-8.

Proffen T et al. Obtaining Structural Information from the Atomic Pair Distribution Function. Zeitschrift fur Krist. 2004, 219 (3), 130-135.

Ribeiro RAP et al. DFT/PBE0 Study on Structural, Electronic and Dielectric Properties of SnZr0.5Ti0.5O3 Lead-Free Ferroelectric Material. J. Alloys. Compds. 2017, 714, 553-559.

Rost CM et al. Entropy-Stabilized Oxides. Nat. Commun. 2015, 6, 8485.

Saal JE et al. Materials Design and Discovery with High-Throughput Density Functional Theory: The Open Quantum Materials Database (OQMD). JOM 2013, 65, 1501-1509.

Shante KS et al. An introduction to percolation theory. Adv. Phys. 1971, 20(85), 325-357.

Simmons EL. Reflectance Spectroscopy: Application of the Kubelka-Munk Theory to the Rates of Photoprocesses of Powders. Appl. Opt. 1976, 15 (4), 951.

Sun W et al. The Thermodynamic Scale of Inorganic Crystalline Metastability. Sci. Adv. 2016, 2 (11), e160025.

Suzuki S et al. Effects of Sn2+ ion Size on Sn Doped SrTiO3. Jpn. J. Appl. Phys. 2013, 52 (9 Part2), 7-10.

Suzuki S et al. Ferroelectricity of Sn-Doped SrTiO3 Perovskites with Tin at Both A and B Sites. Phys. Rev. B—Condens. Matter Mater. Phys. 2012, 86 (6), 8-11.

Walsh A et al. Stereochemistry of Post-Transition Metal Oxides: Revision of the Classical Lone Pair Model. Chem. Soc. Rev. 2011, 40 (9), 4455-4463.

(56) References Cited

OTHER PUBLICATIONS

Wu J et al. Universal Bandgap Bowing in Group-III Nitride Alloys. Solid St. Comm. 2003, 127, 411-414.
Yeh JW et al. Nanostructured High-Entropy Alloys with Multiple Principal Elements: Novel Alloy Design Concepts and Outcomes. Adv. Eng. Mater. 2004, 6 (5), 299-303.
Zoellner B et al. Impact of Nb(V) Substitution on the Structure and Optical and Photoelectrochemical Properties of the $Cu_5(Ta_{1-x}Nb_x)_{11}O_{30}$ Solid Solution. Inorg. Chem. 2019, 58, 6845.
Kresse G et al. Efficiency of Ab-Initio Total Energy Calculations for Metals and Semiconductors Using a Plane-Wave Basis Set. Comput. Mater. Sci. 1996, 6 (1), 15-50.

* cited by examiner

PEROVSKITE MATERIALS AND METHODS OF MAKING AND USE THEREOF

CROSS-REFERENCE TO RELATED APPLICATIONS

This application claims the benefit of priority to U.S. Provisional Application No. 62/984,943 filed Mar. 4, 2020, which is hereby incorporated herein by reference in its entirety.

BACKGROUND

Research into Sn(II)-containing semiconductors has garnered significant interest owing to their potential technological importance, such as within the fields of solar energy conversion, ferroelectrics and transparent conducting oxides (TCOs). In the field of ferroelectrics, Sn(II)-containing perovskites have been intensely investigated as Pb-free, isoelectronic versions of $PbTiO_3$ and $PbZr_{0.5}Ti_{0.5}O_3$. One of the most widely used ceramics in the electronics industry is lead zirconate titanate, known as ferroelectric PZT, which shows a strong piezoelectric effect. This material contains over 60% highly toxic lead by weight and can cause significant safety issues during its processing and use, as lead is volatile and easily released into the environment. The toxicity of PZT also hinders important in vivo uses, as lead can slowly dissolve into a subject's bloodstream. While the increasing use of PZT represents a dangerous and growing concern, it also continues to be mass produced and utilized in a plethora of products because there are currently no suitable replacements for it. Precious few Sn(II)-containing oxides have been synthesized as compared to other metal oxide systems. A primary reason is that, as a reactant, SnO is easily oxidized in air and disproportionates when heated under vacuum or in an inert atmosphere beginning at ~300° C. The compositions and methods discussed herein addresses these and other needs.

SUMMARY

In accordance with the purposes of the disclosed compositions and methods as embodied and broadly described herein, the disclosed subject matter relates to perovskite materials and methods of making and methods of use thereof.

Additional advantages of the disclosed compositions and methods will be set forth in part in the description which follows, and in part will be obvious from the description. The advantages of the disclosed compositions and methods will be realized and attained by means of the elements and combinations particularly pointed out in the appended claims. It is to be understood that both the foregoing general description and the following detailed description are exemplary and explanatory only and are not restrictive of the disclosed systems and methods, as claimed.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

The patent or application file contains at least one drawing executed in color. Copies of this patent or patent application publication with color drawing(s) will be provided by the Office upon request and payment of the necessary fee.

The accompanying figures, which are incorporated in and constitute a part of this specification, illustrate several aspects of the disclosure, and together with the description, serve to explain the principles of the disclosure.

DETAILED DESCRIPTION

Figure 1:
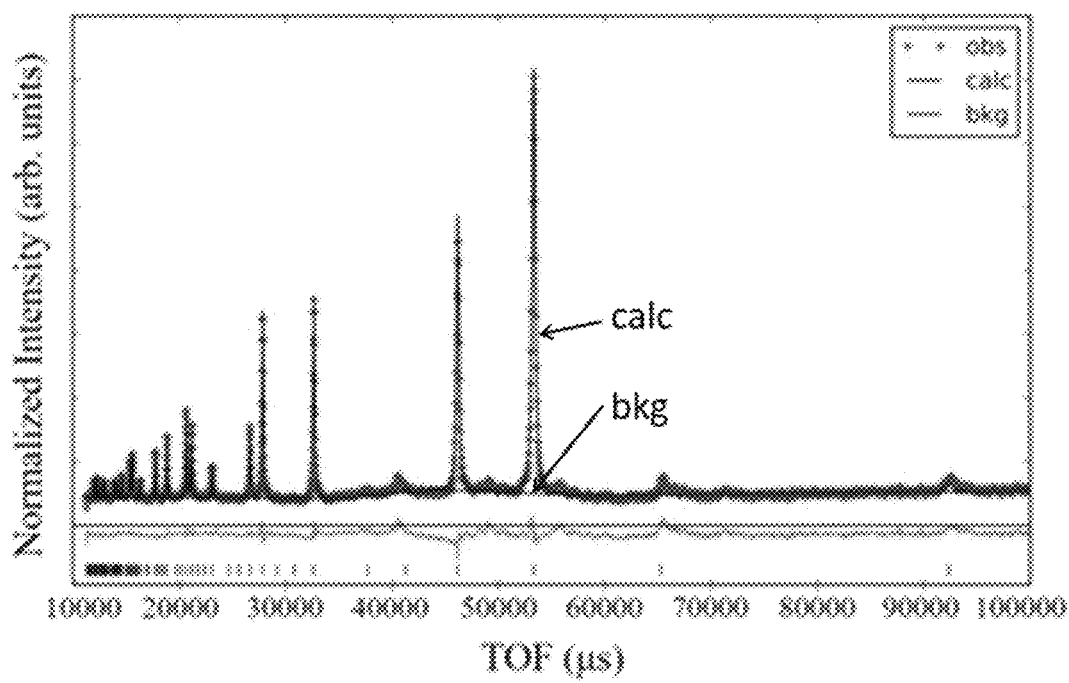
FIG. 1: Plot of Rietveld refinement of neutron diffraction data at room temperature for $(Ba_{0.6}Sn_{0.4})(Zr_{0.5}Ti_{0.5})O_3$.
Figure 2:
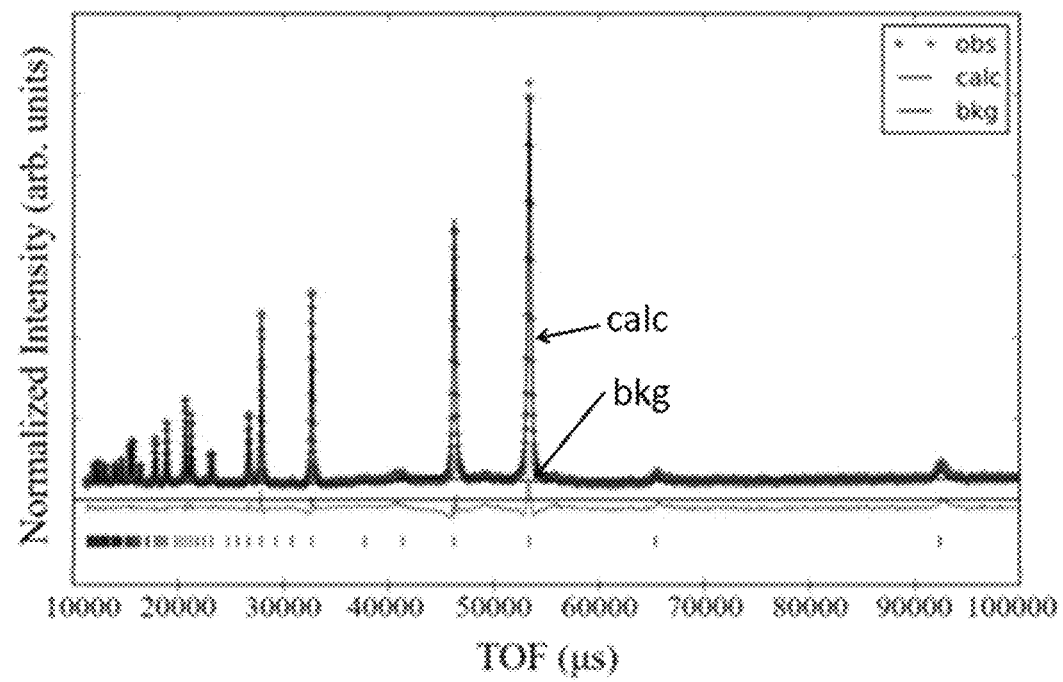
FIG. 2: Plot of Rietveld refinement of neutron diffraction data at room temperature for $(Ba_{0.4}Sn_{0.6})(Zr_{0.5}Ti_{0.5})O_3$.
Figure 3:
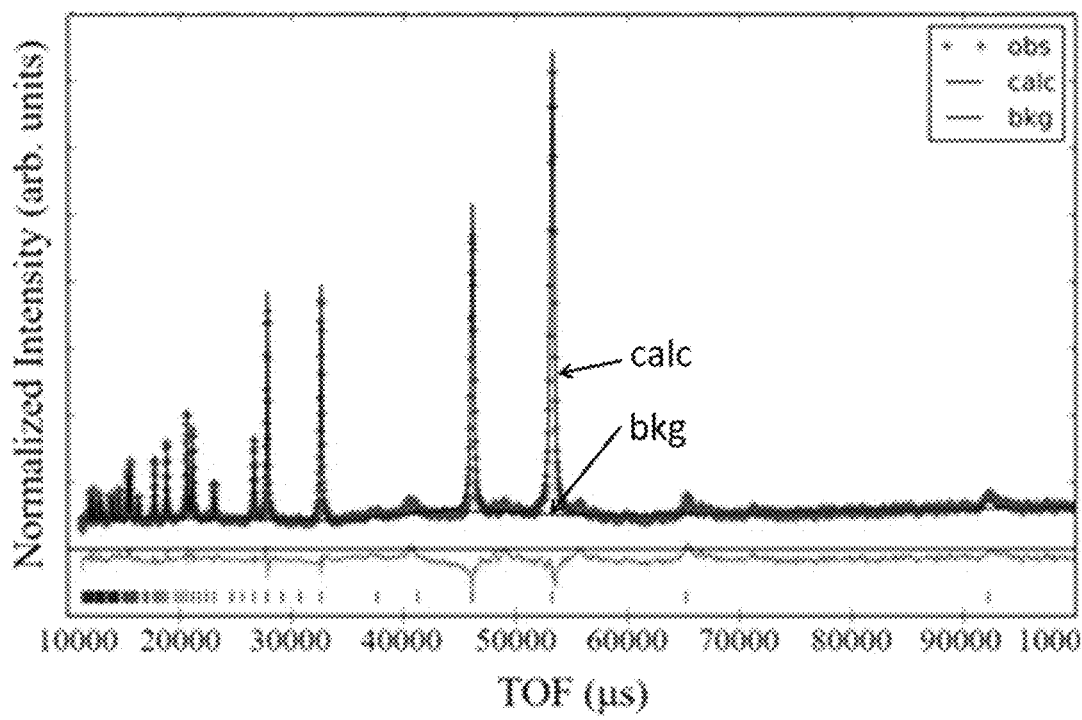
FIG. 3: Plot of Rietveld refinement of neutron diffraction data at 20 K for $(Ba_{0.6}Sn_{0.4})(Zr_{0.5}Ti_{0.5})O_3$.
Figure 4:
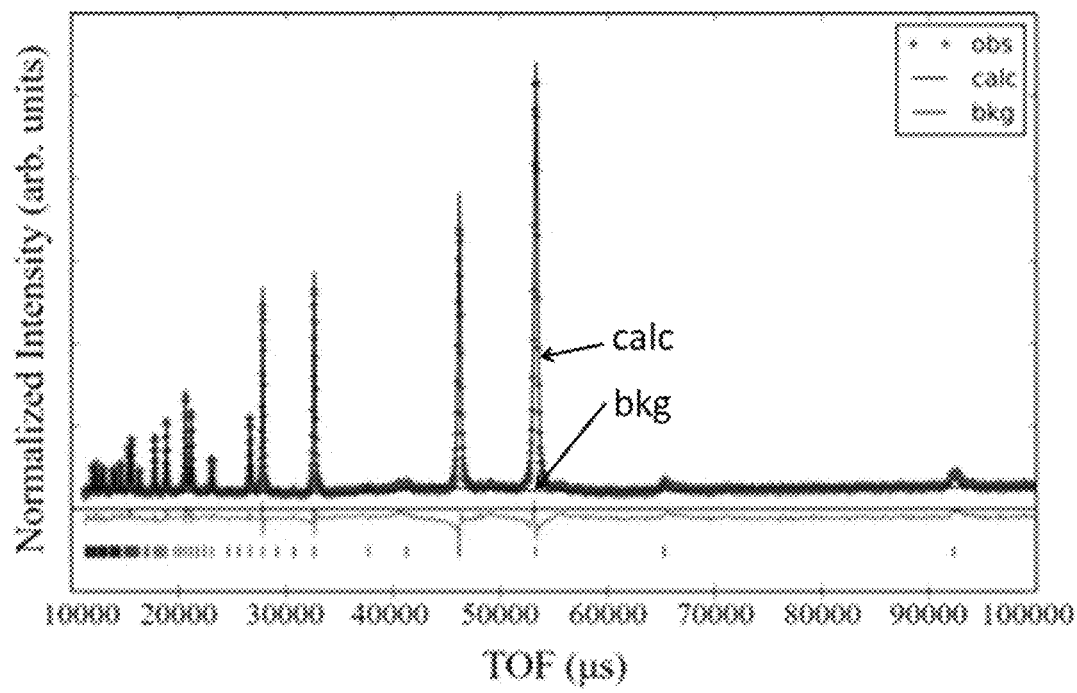
FIG. 4: Plot of Rietveld refinement of neutron diffraction data 20 K for $(Ba_{0.4}Sn_{0.6})(Zr_{0.5}Ti_{0.5})O_3$.

The compositions and methods described herein may be understood more readily by reference to the following detailed description of specific aspects of the disclosed subject matter and the Examples included therein.

Before the present compositions and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Perovskite Materials

Disclosed herein are perovskite materials comprising:

where:
A, if present, is selected from the group consisting of Li, Na, K, Rb, Cs, Be, Mg, Ca, Sr, Ba, Sc, Y, La, Ag, Cd, Tl, Pb, Ce, Pr, Nd, Pm, Sm, Eu, Gd, Tb, Dy, Ho, Er, Tm, Yb, Lu, or a combination thereof;

B and B', if present, are independently selected from the group consisting of Al, Sc, Ti, V, Cr, Mn, Fe, Co, Ni, Cu, Zn, Ga, Ge, Y, Zr, Nb, Mo, Ru, Rh, Pd, Ag, Cd, In, Sn, Sb, Te, La, Hf, Ta, W, Re, Os, Ir, Pt, Au, Bi, or a combination thereof;

x is from greater than 0 to 1; and y is from 0 to 1;

with the proviso that A and B are different, A and B' are different, and B and B' are different.

In some examples, x is greater than 0 (e.g., 0.01 or more, 0.02 or more, 0.03 or more, 0.04 or more, 0.05 or more, 0.06 or more, 0.07 or more, 0.08 or more, 0.09 or more, 0.1 or more, 0.15 or more, 0.2 or more, 0.25 or more, 0.3 or more, 0.35 or more, 0.4 or more, 0.45 or more, 0.5 or more, 0.55 or more, 0.6 or more, 0.65 or more, 0.7 or more, 0.75 or more, 0.8 or more, 0.85 or more, or 0.9 or more). In some examples, x is 1 or less (e.g., 0.95 or less, 0.9 or less, 0.85 or less, 0.8 or less, 0.75 or less, 0.7 or less, 0.65 or less, 0.6 or less, 0.55 or less, 0.5 or less, 0.45 or less, 0.4 or less, 0.35 or less, 0.3 or less, 0.25 or less, 0.2 or less, 0.15 or less, 0.1 or less, 0.09 or less, 0.08 or less, 0.07 or less, 0.06 or less, or 0.05 or less). The value of x can range from any of the minimum values described above to any of the maximum values described above. For example, x can be from greater than 0 to 1 (e.g., from greater than 0 to 0.5, from 0.5 to 1, from greater than 0 to 0.4, from 0.4 to 0.7, from 0.7 to 1, from 0.1 to 1, from greater than 0 to 0.9, from 0.1 to 0.9, from 0.1 to 0.5, from 0.1 to 0.4, from 0.2 to 1, from 0.4 to 1, from 0.6 to 1, from 0.8 to 1, from 0.9 to 1, from 0.1 to 0.6, or from 0.5 to 0.6). In some examples, x is 1.

In some examples, y is 0 or more (e.g., 0.05 or more, 0.1 or more, 0.15 or more, 0.2 or more, 0.25 or more, 0.3 or more, 0.35 or more, 0.4 or more, 0.45 or more, 0.5 or more, 0.55 or more, 0.6 or more, 0.65 or more, 0.7 or more, 0.75 or more, 0.8 or more, 0.85 or more, 0.9 or more, or 0.95 or more). In some examples, y is 1 or less (e.g., 0.95 or less, 0.9 or less, 0.85 or less, 0.8 or less, 0.75 or less, 0.7 or less, 0.65 or less, 0.6 or less, 0.55 or less, 0.5 or less, 0.45 or less, 0.4 or less, 0.35 or less, 0.3 or less, 0.25 or less, 0.2 or less, 0.15 or less, 0.1 or less, or 0.05 or less). The value of y can range from any of the minimum values described above to any of the maximum values described above. For example, y can be from 0 to 1 (e.g., from 0 to 0.5, from 0.5 to 1, from 0 to 0.2, from 0.2 to 0.4, from 0.4 to 0.6, from 0.6 to 0.8, from 0.8 to 1, from 0 to 0.9, from 0.1 to 1, from 0.1 to 0.9, or from 0.25 to 0.75). In some examples, y is 0. In some examples, y is 1.

In some examples, the perovskite material comprises $[Ba_{1-x}Sn_x][Zr_{1-y}Ti_y]O_3$. For example, the perovskite material can comprise $[Ba_{1-x}Sn_x][Zr_{1-y}Ti_y]O_3$, where x is from 0.1 to 1 and y is 0, 0.25, 0.5, 0.75, or 1. In some examples, the perovskite material comprises $[Ba_{1-x}Sn_x][Zr_{0.25}Ti_{0.75}]O_3$, where x is from 0.1 to 0.4. In some examples, the perovskite material comprises $[Ba_{1-x}Sn_x][Zr_{0.5}Ti_{0.5}]O_3$, where x is from 0.1 to 0.6 (e.g., wherein x is from 0.5 to 0.6). In some examples, the perovskite material comprises $[Ba_{1-x}Sn_x]ZrO_3$, where x is from 0.1 to 0.6 (e.g., wherein is from 0.5 to 0.6). The perovskite material can, for example, comprise $Ba_{0.8}Sn_{0.2}Zr_{0.25}Ti_{0.75}O_3$, $Ba_{0.8}Sn_{0.2}Zr_{0.5}Ti_{0.5}O_3$, $Ba_{0.6}Sn_{0.4}Zr_{0.5}Ti_{0.5}O_3$, $Ba_{0.4}Sn_{0.6}Zr_{0.5}Ti_{0.5}O_3$, $Ba_{0.8}Sn_{0.2}Zr_{0.75}Ti_{0.25}O_3$, $Ba_{0.8}Sn_{0.2}ZrO_3$, $Ba_{0.6}Sn_{0.4}ZrO_3$, $Ba_{0.9}Sn_{0.1}TiO_3$, or a combination thereof.

In some examples, the perovskite material comprises $[Pb_{1-x}Sn_x][Zr_{1-y}Ti_y]O_3$. For example, the perovskite material cam comprise $[Pb_{1-x}Sn_x][Zr_{1-y}Ti_y]O_3$ where x is from greater than 0 to 1 (e.g., wherein x is from 0.1 to 1, or from 0.5 to 1) and y is 0, 0.25, 0.5, 0.75, or 1.

In some examples, the perovskite material substantially excludes lead, such that the perovskite material comprises a lead-free perovskite material. In some examples, the perovskite material is biocompatible.

The perovskite materials described herein can, for example, have a cubic perovskite structure.

The perovskite materials described herein can, in some example, comprise a particle (e.g., a perovskite particle), e.g. also described herein are particles comprising the perovskite materials described herein. As used herein, "a perovskite particle" and "the perovskite particle" are meant to include any number of perovskite particles. Thus, for example "the perovskite particle" includes one or more perovskite particles. In some examples, the perovskite particle can comprise a plurality of perovskite particles.

The perovskite particle can comprise a particle of any shape. The perovskite particle can have an irregular shape, a regular shape, an isotropic shape, an anisotropic shape, or a combination thereof. In some examples, the perovskite particle can have an isotropic shape. In some examples, the perovskite particle can have an anisotropic shape. In some examples, the perovskite particle can have a shape that is substantially spherical, ellipsoidal, triangular, pyramidal, tetrahedral, cylindrical, rectangular, cuboidal, or cuboctahedral. In some examples, the perovskite particle can have a shape that is substantially rectangular, cuboidal, or cuboctahedral.

The perovskite particle can have an average particle size. "Average particle size" and "mean particle size" are used interchangeably herein, and generally refer to the statistical mean particle size of the particles in a population of particles. For example, the average particle size for a plurality of particles with a substantially spherical shape can comprise the average diameter of the plurality of particles. For a particle with a substantially spherical shape, the diameter of a particle can refer, for example, to the hydrodynamic diameter. As used herein, the hydrodynamic diameter of a particle can refer to the largest linear distance between two points on the surface of the particle. For an anisotropic particle, the average particle size can refer to, for example, the average maximum dimension of the particle (e.g., the length of a rod shaped particle, the diagonal of a cube shape particle, the bisector of a triangular shaped particle, etc.) For an anisotropic particle, the average particle size can refer to, for example, the hydrodynamic size of the particle. Mean particle size can be measured using methods known in the art, such as evaluation by scanning electron microscopy, transmission electron microscopy, and/or dynamic light scattering.

The perovskite particle can, for example, have an average particle size of 10 nm or more (e.g., 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (micron, µm) or more, 2 microns or more, 3 microns or more, 4 microns or more, 5 microns or more, 10 microns or more, 15 microns or more, 20 microns or more, 25 microns or more, 30 microns or more, 35 microns or more, 40 microns or more, 45 microns or more, 50 microns or more, 60 microns or more, 70 microns or more, 80 microns or more, 90 microns or more, 100 microns or more, 125 microns or more, 150 microns or more, 175 microns or more, 200 microns or more, 225 microns or more, 250 microns or more, 300 microns or more, 350 microns or more, 400 microns or more, 450 microns or more, 500 microns or more, 600 microns or more, 700 microns or more, 800 microns or more, or 900 microns or more). In some examples, the perovskite particle can have an average particle size of 1 millimeter (mm) or less (e.g., 900 microns or less, 800 microns or less, 700 microns or less, 600 microns or less, 500 microns or less, 450 microns or less, 400 microns or less, 350 microns or less, 300 microns or less, 250 microns or less, 225 microns or less, 200 microns or less, 175 microns or less, 150 microns or less, 125 microns or less, 100 microns or less, 90 microns or less, 80 microns or less, 70 microns or less, 60 microns or less, 50 microns or less, 45 microns or less, 40 microns or less, 35 microns or less, 30 microns or less, 25 microns or less, 20 microns or less, 15 microns or less, 10 microns or less, 5 microns or less, 4 microns or less, 3 microns or less, 2 microns or less, 1 micron or less, 900 nm or less, 800 nm or less, 700 nm or less, 600 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, or 15 nm or less).

The average particle size of the perovskite particle can range from any of the minimum values described above to any of the maximum values described above. For example, the perovskite particle can have an average particle size of from 10 nm to 1 mm (e.g., from 10 nm to 100 nm, from 100 nm to 1 micron, from 1 micron to 10 microns, from 10 microns to 100 microns, from 100 microns to 1 mm, from 1 nm to 500 nm, from 500 nm to 1 micron, from 1 micron to 500 microns, from 500 microns to 1 mm, from 125 nm to 5 microns, from 125 nm to 500 nm, from 100 nm to 5 microns, or from 500 nm to 2 microns). The average particle size of the perovskite particle can, for example, be measured using electron microscopy.

In some examples, the perovskite particle can comprise a plurality of perovskite particles, and the plurality of perovskite particles can be substantially monodisperse. "Monodisperse" and "homogeneous size distribution," as used herein, and generally describe a population of particles where all of the particles have the same or nearly the same particle size. As used herein, a monodisperse distribution refers to particle distributions in which 80% of the distribution (e.g., 85% of the distribution, 90% of the distribution, or 95% of the distribution) lies within 25% of the average particle size (e.g., within 20% of the average particle size, within 15% of the average particle size, within 10% of the average particle size, or within 5% of the average particle size).

In some examples, the perovskite particle has a bandgap that overlaps with at least a portion of the solar spectrum. The size, shape, and/or composition of the perovskite particle can be selected in view of a variety of factors. In some examples, the size, shape, and/or composition can be selected such that the perovskite particle has a bandgap that overlaps with at least a portion of the solar spectrum. In some examples, the size, shape, and/or composition of the perovskite particle can be selected in view of the intended use of the perovskite material.

In some examples, the perovskite particle can comprise a plurality of perovskite particles and the plurality of perovskite particles can comprise: a first population of particles comprising a first material and having a first average particle size and a first particle shape; and a second population of particles comprising a second material and having a second average particle size and a second particle shape; wherein the first average particle size and the second average particle size are different, the first particle shape and the second particle shape are different, the first material and the second material are different, or a combination thereof. In some examples, the plurality of perovskite particles can comprise a mixture of a plurality of populations of particles, wherein each population of particles within the mixture has a different size, shape, composition, or combination thereof.

The perovskite materials described herein can, in some examples, be metastable. For example, the perovskite materials can have a reaction energy of 0.25 eV atom$^{-1}$ or more with respect to decomposition to a simpler oxide and/or to an ilmenite structure (e.g., 0.3 eV atom$^{-1}$ or more, 0.35 eV atom$^{-1}$ or more, 0.4 eV atom$^{-1}$ or more, or 0.45 eV atom$^{-1}$ or more). In some examples, the perovskite material can have a reaction energy of 0.5 eV atom$^{-1}$ or less with respect to decomposition to a simpler oxide and/or to an ilmenite structure (e.g., 0.45 eV atom-1 or less, 0.4 eV atom$^{-1}$ or less, 0.35 eV atom$^{-1}$ or less, or 0.3 eV atom$^{-1}$ or less). The reaction energy of the perovskite material with respect to decomposition to a simpler oxide and/or to an ilmenite structure can range from any of the minimum values described above to any of the maximum values described above. For example, the perovskite materials can have a reaction energy of from 0.25 eV atom$^{-1}$ to 0.5 eV atom$^{-1}$ with respect to decomposition to a simpler oxide and/or to an ilmenite structure (e.g., from 0.25 eV atom$^{-1}$ to 0.35 eV atom$^{-1}$, from 0.35 eV atom$^{-1}$ to 0.5 eV atom$^{-1}$, from 0.25 eV atom$^{-1}$ to 0.3 eV atom$^{-1}$, from 0.3 eV atom$^{-1}$ to 0.35 eV atom$^{-1}$, from 0.35 eV atom$^{-1}$ to 0.4 eV atom$^{-1}$, from 0.45 eV atom$^{-1}$ to 0.5 eV atom$^{-1}$, from 0.3 eV atom$^{-1}$ to 0.5 eV atom$^{-1}$, from 0.25 eV atom$^{-1}$ to 0.45 eV atom$^{-1}$, from 0.3 eV atom$^{-1}$ to 0.45 eV atom$^{-1}$, from 0.3 eV atom$^{-1}$ to 0.5 eV atom$^{-1}$, or from 0.4 eV atom$^{-1}$ to 0.5 eV atom$^{-1}$).

In some examples, the perovskite material is ferroelectric. In some examples, the perovskite material comprises a lead-free ferroelectric material.

In some examples, the perovskite material comprises a semiconductor with a bandgap that overlaps with at least a portion of the solar spectrum. For example, the perovskite material can comprise a semiconductor with a bandgap of 1.6 eV or more (e.g., 1.65 eV or more, 1.7 eV or more, 1.75 eV or more, 1.8 eV or more, 1.85 eV or more, 1.9 eV or more, 1.95 eV or more, 2 eV or more, 2.1 eV or more, 2.2 eV or more, 2.3 eV or more, 2.4 eV or more, 2.5 eV or more, 2.6 eV or more, 2.7 eV or more, 2.8 eV or more, 2.9 eV or more, 3 eV or more, 3.1 eV or more, 3.2 eV or more, 3.3 eV or more, 3.4 eV or more, 3.5 eV or more, 3.6 eV or more, 3.7 eV or more, or 3.8 eV or more). In some examples, the perovskite material can comprise a semiconductor with a bandgap of 3.9 eV or less (e.g., 3.8 eV or less, 3.7 eV or less, 3.6 eV or less, 3.5 eV or less, 3.4 eV or less, 3.3 eV or less, 3.2 eV or less, 3.1 eV or less, 3 eV or less, 2.9 eV or less, 2.8 eV or less, 2.7 eV or less, 2.6 eV or less, 2.5 eV or less, 2.4 eV or less, 2.3 eV or less, 2.2 eV or less, 2.1 eV or less, 2 eV or less, 1.95 eV or less, 1.9 eV or less, 1.85 eV or less, 1.8 eV or less, 1.75 eV or less, or 1.7 eV or less). The bandgap can range from any of the minimum values described above to any of the maximum values described above. For example, the perovskite can comprise a semiconductor with a bandgap of from 1.6 eV to 3.9 eV (e.g., from 1.6 eV to 2.8 eV, from 2.8 eV to 3.9 eV, from 1.6 eV to 2 eV, from 2 eV to 2.4 eV, from 2.4 eV to 2.8 eV, from 2.8 eV to 3.2 eV, from 3.2 eV to 3.6 eV, from 3.6 eV to 2.9 eV, from 1.6 eV to 3.8 eV, from 1.7 eV to 3.9 eV, from 1. eV 7 to 3.8 eV, or from 1.95 eV to 3 eV).

The perovskite material can, for example, comprise a photocatalyst. In some examples, the perovskite material comprises a photocatalyst that exhibits a photocatalytic rate of 100 μmol $O_2$ $h^{-1}$ $g^{-1}$ or more (e.g., 125 μmol $O_2$ $h^{-1}$ $g^{-1}$ or more, 150 μmol $O_2$ $h^{-1}$ $g^{-1}$ or more, 175 μmol $O_2$ $h^{-1}$ $g^{-1}$ or more, 200 μmol $O_2$ $h^{-1}$ $g^{-1}$ or more, 225 μmol $O_2$ $h^{-1}$ $g^{-1}$ or more, 250 μmol $O_2$ $h^{-1}$ $g^{-1}$ or more, 275 μmol $O_2$ $h^{-1}$ $g^{-1}$ or more, 300 μmol $O_2$ $h^{-1}$ $g^{-1}$ or more, 325 μmol $O_2$ $h^{-1}$ $g^{-1}$ or more, 350 μmol $O_2$ $h^{-1}$ $g^{-1}$ or more, 375 μmol $O_2$ $h^{-1}$ $g^{-1}$ or more, 400 μmol $O_2$ $h^{-1}$ $g^{-1}$ or more, 425 μmol $O_2$ $h^{-1}$ $g^{-1}$ or more, 450 μmol $O_2$ $h^{-1}$ $g^{-1}$ or more, 475 μmol $O_2$ $h^{-1}$ $g^{-1}$ or more, 500 μmol $O_2$ $h^{-1}$ $g^{-1}$ or more, 550 μmol $O_2$ $h^{-1}$ $g^{-1}$ or more, 600 μmol $O_2$ $h^{-1}$ $g^{-1}$ or more, 650 μmol $O_2$ $h^{-1}$ $g^{-1}$ or more, 700 μmol $O_2$ $h^{-1}$ $g^{-1}$ or more, 750 μmol $O_2$ $h^{-1}$ $g^{-1}$ or more, 800 μmol $O_2$ $h^{-1}$ $g^{-1}$ or more, 850 μmol $O_2$ $h^{-1}$ $g^{-1}$ or more, 900 μmol $O_2$ $h^{-1}$ $g^{-1}$ or more, 950 μmol $O_2$ $h^{-1}$ $g^{-1}$ or more, 1000 μmol $O_2$ $h^{-1}$ $g^{-1}$ or more, 1100 μmol $O_2$ $h^{-1}$ $g^{-1}$ or more, 1200 μmol $O_2$ $h^{-1}$ $g^{-1}$ or more, 1300 μmol $O_2$ $h^{-1}$ $g^{-1}$ or more, 1400 μmol $O_2$ $h^{-1}$ $g^{-1}$ or more, 1500 μmol $O_2$ $h^{-1}$ $g^{-1}$ or more, 2000 μmol $O_2$ $h^{-1}$ $g^{-1}$ or more, 2500 μmol $O_2$ $h^{-1}$ $g^{-1}$ or more, 3000 μmol $O_2$ $h^{-1}$ $g^{-1}$ or more, 3500 μmol $O_2$ $h^{-1}$ $g^{-1}$ or more, 4000 μmol $O_2$ $h^{-1}$ $g^{-1}$ or more, or 4500 μmol $O_2$ $h^{-1}$ $g^{-1}$ or more). In some examples, the perovskite material comprises a photocatalyst that exhibits a photocatalytic rate of 5000 μmol 02 $h^{-1}$ $g^{-1}$ or less (e.g., 4500 μmol $O_2$ $h^{-1}$ $g^{-1}$ or less, 4000 μmol $O_2$ $h^{-1}$ $g^{-1}$ or less, 3500 μmol $O_2$ $h^{-1}$ $g^{-1}$ or less, 3000 μmol $O_2$ $h^{-1}$ $g^{-1}$ or less, 2500 μmol $O_2$ $h^{-1}$ $g^{-1}$ or less, 2000 μmol $O_2$ $h^{-1}$ $g^{-1}$ or less, 1500 μmol $O_2$ $h^{-1}$ $g^{-1}$ or less, 1400 μmol $O_2$ $h^{-1}$ $g^{-1}$ or less, 1300 μmol $O_2$ $h^{-1}$ $g^{-1}$ or less, 1200 μmol $O_2$ $h^{-1}$ $g^{-1}$ or less, 1100 μmol $O_2$ $h^{-1}$ $g^{-1}$ or less, 1000 μmol $O_2$ $h^{-1}$ $g^{-1}$ or less, 950 μmol $O_2$ $h^{-1}$ $g^{-1}$ or less, 900 μmol $O_2$ $h^{-1}$ $g^{-1}$ or less, 850 μmol $O_2$ $h^{-1}$ $g^{-1}$ or less, 800 μmol $O_2$ $h^{-1}$ $g^{-1}$ or less, 750 μmol $O_2$ $h^{-1}$ $g^{-1}$ or less, 700 μmol $O_2$ $h^{-1}$ $g^{-1}$ or less, 650 μmol $O_2$ $h^{-1}$ $g^{-1}$ or less, 600 μmol $O_2$ $h^{-1}$ $g^{-1}$ or less, 550 μmol $O_2$ $h^{-1}$ $g^{-1}$ or less, 500 μmol $O_2$ $h^{-1}$ $g^{-1}$ or less, 475 μmol $O_2$ $h^{-1}$ $g^{-1}$ or less, 450 μmol $O_2$ $h^{-1}$ $g^{-1}$ or less, 425 μmol $O_2$ $h^{-1}$ $g^{-1}$ or less, 400 μmol $O_2$ $h^{-1}$ $g^{-1}$ or less, 375 μmol $O_2$ $h^{-1}$ $g^{-1}$ or less, 350 μmol $O_2$ $h^{-1}$ $g^{-1}$ or less, 325 μmol $O_2$ $h^{-1}$ $g^{-1}$ or less, 300 μmol $O_2$ $h^{-1}$ $g^{-1}$ or less, 275 μmol $O_2$ $h^{-1}$ $g^{-1}$ or less, 250 μmol $O_2$ $h^{-1}$ $g^{-1}$ or less, 225 μmol $O_2$ $h^{-1}$ $g^{-1}$ or less, 200 μmol $O_2$ $h^{-1}$ $g^{-1}$ or less, 175 μmol $O_2$ $h^{-1}$ $g^{-1}$ or less, or 150 μmol $O_2$ $h^{-1}$ $g^{-1}$ or less). The photocatalytic rate exhibited by the perovskite material can range from any of the minimum values described above to any of the maximum values described above. For example, the perovskite material comprises a photocatalyst that exhibits a photocatalytic rate from 100 μmol $O_2$ $h^{-1}$ $g^{-1}$ to 5000 μmol $O_2$ $h^{-1}$ $g^{-1}$ (e.g., from 100 μmol $O_2$ $h^{-1}$ $g^{-1}$ to 500 μmol $O_2$ $h^{-1}$ $g^{-1}$, from 500 μmol $O_2$ $h^{-1}$ $g^{-1}$ to 1000 μmol $O_2$ $h^{-1}$ $g^{-1}$, from 1000 μmol $O_2$ $h^{-1}$ $g^{-1}$ to 5000 μmol $O_2$ $h^{-1}$ $g^{-1}$, from 100 μmol $O_2$ $h^{-1}$ $g^{-1}$ to 1000 μmol $O_2$ $h^{-1}$ $g^{-1}$, or from 500 μmol $O_2$ $h^{-1}$ $g^{-1}$ to 5000 μmol $O_2$ $h^{-1}$ $g^{-1}$).

The perovskite material can comprise a photocatalyst that exhibits a photocatalytic rate from 100 μmol $O_2$ $h^{-1}$ $g^{-1}$ to 5000 μmol $O_2$ $h^{-1}$ $g^{-1}$ under electromagnetic irradiation at one or more wavelengths of 230 nm or more (e.g., 240 nm or more, 250 nm or more, 260 nm or more, 270 nm or more, 280 nm or more, 290 nm or more, 300 nm or more, 325 nm or more, 350 nm or more, 375 nm or more, 400 nm or more, 425 nm or more, 450 nm or more, 475 nm or more, 500 nm or more, 525 nm or more, 550 nm or more, 575 nm or more, 600 nm or more, 625 nm or more, 650 nm or more, 675 nm or more, 700 nm or more, 750 nm or more, 800 nm or more, 850 nm or more, 900 nm or more, or 950 nm or more). In some examples, the perovskite material can comprise a photocatalyst that exhibits a photocatalytic rate from 100 µmol $O_2$ $h^{-1}$ $g^{-1}$ to 5000 µmol $O_2$ $h^{-1}$ $g^{-1}$ under electromagnetic irradiation at one or more wavelengths of 1023 nm or less (e.g., 1000 nm or less, 950 nm or less, 900 nm or less, 850 nm or less, 800 nm or less, 750 nm or less, 700 nm or less, 675 nm or less, 650 nm or less, 625 nm or less, 600 nm or less, 575 nm or less, 550 nm or less, 525 nm or less, 500 nm or less, 475 nm or less, 450 nm or less, 425 nm or less, 400 nm or less, 375 nm or less, 350 nm or less, 325 nm or less, 300 nm or less, 290 nm or less, 280 nm or less, 270 nm or less, 260 nm or less, or 250 nm or less). The perovskite material can comprise a photocatalyst that exhibits a photocatalytic rate from 100 µmol $O_2$ $h^{-1}$ $g^{-1}$ to 5000 µmol $O_2$ $h^{-1}$ $g^{-1}$ under electromagnetic irradiation at one or more wavelengths that range from any of the minimum values described above to any of the maximum values described above. For example, the perovskite material can comprise a photocatalyst that exhibits a photocatalytic rate from 100 µmol $O_2$ $h^{-1}$ $g^{-1}$ to 5000 µmol $O_2$ $h^{-1}$ $g^{-1}$ under electromagnetic irradiation at one or more wavelengths from 230 nm to 1023 nm (e.g., from 230 nm to 700 nm, from 700 nm to 1023 nm, from 230 nm to 575 nm, from 400 nm to 575 nm, from 400 nm to 1023 nm, or from 575 nm to 1023 nm).

In some examples, the perovskite material comprises a photocatalyst that exhibits an apparent quantum yield of 0.3% or more (e.g., 0.35% or more, 0.4% or more, 0.45% or more, 0.5% or more, 0.6% or more, 0.7% or more, 0.8% or more, 0.9% or more, 1% or more, 1.25% or more, 1.5% or more, 1.75% or more, 2% or more, 2.25% or more, 2.5% or more, 3% or more, 3.5% or more, 4% or more, 4.5% or more, 5% or more, 6% or more, 7% or more, 8% or more, 9% or more, 10% or more, 15% or more, 20% or more, 25% or more, 30% or more, 35% or more, or 40% or more). In some examples, the perovskite material can comprise a photocatalyst that exhibits an apparent quantum yield of 50% or less (e.g., 45% or less, 40% or less, 35% or less, 30% or less, 25% or less, 20% or less, 15% or less, 10% or less, 9% or less, 8% or less, 7% or less, 6% or less, 5% or less, 4.5% or less, 4% or less, 3.5% or less, 3% or less, 2.5% or less, 2.25% or less, 2% or less, 1.75% or less, 1.5% or less, 1.25% or less, 1% or less, 0.9% or less, 0.8% or less, 0.7% or less, 0.6% or less, 0.5% or less, 0.45% or less, or 0.4% or less). The apparent quantum yield exhibited by the perovskite material can range from any of the minimum values described above to any of the maximum values described above. For example, the perovskite material can comprise a photocatalyst that exhibits an apparent quantum yield of from 0.3% to 50% (e.g., from 0.3% to 1%, from 1% to 10%, from 10% to 50%, from 0.3% to 40%, from 0.5% to 50%, or from 1% to 50%).

Also described herein are films comprising the perovskite materials described herein. The films can, for example, have a thickness of 100 nm or more (e.g., 125 nm or more, 150 nm or more, 175 nm or more, 200 nm or more, 225 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (micron, µm) or more, 1.25 microns or more, 1.5 microns or more, 1.75 microns or more, 2 microns or more, 2.25 microns or more, 2.5 microns or more, 2.75 microns or more, 3 microns or more, 3.25 microns or more, 3.5 microns or more, 3.75 microns or more, 4 microns or more, 4.25 microns or more, or 4.5 microns or more). In some examples, the films can have a thickness of 5 microns or less (e.g., 4.75 microns or less, 4.5 microns or less, 4.25 microns or less, 4 microns or less, 3.75 microns or less, 3.5 microns or less, 3.25 microns or less, 3 microns or less, 2.75 microns or less, 2.5 microns or less, 2.25 microns or less, 2 microns or less, 1.75 microns or less, 1.5 microns or less, 1.25 microns or less, 1 micron or less, 900 nm or less, 800 nm or less, 700 nm or less, 600 nm or less, 500 nm or less, 450 nm or less, 400 nm or less, 350 nm or less, 300 nm or less, 250 nm or less, 225 nm or less, 200 nm or less, 175 nm or less, or 150 nm or less). The thickness of the films can range from any of the minimum values described above to any of the maximum values described above. For example, the films can have a thickness of from 100 nanometers to 5 micrometers (e.g., from 100 nm to 500 nm, from 500 nm to 1 micron, from 1 micron to 5 microns, from 100 nm to 4 microns, from 200 nm to 5 microns, or from 200 nm to 4 microns).

Methods of Making

Also disclosed herein are methods of making perovskite materials, such as metastable perovskite materials. Also disclosed herein are methods of making the perovskite materials disclosed herein. The methods can, for example, comprise a peritectic flux reaction between a preliminary perovskite material and a Sn(II)-halide salt. The term "preliminary perovskite material" is used herein to refer to a perovskite material before it has undergone a peritectic flux reaction with a Sn(II)-halide salt as described herein. It is not meant to imply that the preliminary perovskite material is not yet a perovskite material. For example, the preliminary perovskite material can comprise a perovskite having a formula $A[B_{1-y}B'_y]O_3$. In some examples, the preliminary perovskite comprises lead zirconate titanate (PZT).

In some examples, the method comprises contacting a preliminary perovskite comprising $A[B_{1-y}B'_y]O_3$ with a Sn(II)-halide salt comprising $SnCl_2$ and/or $SnF_2$. In some examples, the preliminary perovskite comprises lead zirconate titanate (PZT). For example, the methods described herein can comprise converting a lead-containing perovskite to a lead-free perovskite by extracting the lead from the lead-containing perovskite.

The method can, for example, be performed at a temperature of 20° C. or more (e.g., 25° C. or more, 30° C. or more, 35° C. or more, 40° C. or more, 45° C. or more, 50° C. or more, 60° C. or more, 70° C. or more, 80° C. or more, 90° C. or more, 100° C. or more, 125° C. or more, 150° C. or more, 175° C. or more, 200° C. or more, 225° C. or more, 250° C. or more, 275° C. or more, 300° C. or more, 325° C. or more, 350° C. or more, 375° C. or more, 400° C. or more, 425° C. or more, or 450° C. or more). In some examples, the method can be performed at a temperature of 500° C. or less (e.g., 475° C. or less, 450° C. or less, 425° C. or less, 400° C. or less, 375° C. or less, 350° C. or less, 325° C. or less, 300° C. or less, 275° C. or less, 250° C. or less, 225° C. or less, 200° C. or less, 175° C. or less, 150° C. or less, 125° C. or less, 100° C. or less, 90° C. or less, 80° C. or less, 70° C. or less, 60° C. or less, 50° C. or less, 45° C. or less, 40° C. or less, 35° C. or less, or 30° C. or less). The temperature at which the method is performed can range from any of the minimum values described above to any of the maximum values described above. For example, the method can be performed at a temperature of from 20° C. to 500° C. (e.g., from 20° C. to 250° C., from 250° C. to 500° C., from 20° C. to 100° C., from 100° C. to 200° C., from 200° C. to 300° C., from 300° C. to 400° C., from 400° C. to 500° C., from 20° C. to 400° C., from 20° C. to 350° C., from 50° C. to 350° C., or from 50° C. to 250° C.).

In some examples, the preliminary perovskite can be contacted with the Sn(II)-halide salt for an amount of time of 5 minutes or more (e.g., 10 minutes or more, 15 minutes or more, 20 minutes or more, 25 minutes or more, 30 minutes or more, 35 minutes or more, 40 minutes or more, 45 minutes or more, 50 minutes or more, 55 minutes or more, 1 hour or more, 1.5 hours or more, 2 hours or more, 2.5 hours or more, 3 hours or more, 3.5 hours or more, 4 hours or more, 4.5 hours or more, 5 hours or more, 5.5 hours or more, 6 hours or more, 7 hours or more, 8 hours or more, 9 hours or more, 10 hours or more, 11 hours or more, 12 hours or more, 14 hours or more, 16 hours or more, 18 hours or more, 20 hours or more, or 22 hours or more). In some examples, the preliminary perovskite can be contacted with the Sn(II)-halide salt for an amount of time of 24 hours or less (e.g., 22 hours or less, 20 hours or less, 18 hours or less, 16 hours or less, 14 hours or less, 12 hours or less, 11 hours or less, 10 hours or less, 9 hours or less, 8 hours or less, 7 hours or less, 6 hours or less, 5.5 hours or less, 5 hours or less, 4.5 hours or less, 4 hours or less, 3.5 hours or less, 3 hours or less, 2.5 hours or less, 2 hours or less, 1.5 hours or less, 1 hours or less, 55 minutes or less, 50 minutes or less, 45 minutes or less, 40 minutes or less, 35 minutes or less, 30 minutes or less, 25 minutes or less, 20 minutes or less, 15 minutes or less, or 10 minutes or less). The amount of time that the preliminary perovskite can be contacted with the Sn(II)-halide salt can range from any of the minimum values described above to any of the maximum values described above. For example, preliminary perovskite can be contacted with the Sn(II)-halide salt for an amount of time of from 5 minutes to 24 hours (e.g., from 5 minutes to 1 hour, from 1 hour to 12 hours, from 12 hours to 24 hours, from 5 minutes to 12 hours, from 10 minutes to 30 minutes, or from 10 hours to 14 hours).

The method can, for example, be performed under vacuum and/or an inert atmosphere (e.g., Ar, $N_2$, etc.).

In some examples, the preliminary perovskite material is contacted with the Sn(II)-halide salt for a first amount of time (e.g., from 10 minutes to 30 minutes) at a first temperature (from 20° C. to 50° C.) under an inert atmosphere (e.g., argon), and subsequently for a second amount of time (e.g., from 10 hours to 14 hours) at a second temperature (e.g., from 300° C. to 400° C.) under vacuum. In some examples, after the second amount of time, the methods can further comprise cooling the perovskite material. In some examples, the methods can further comprise subsequently washing and then drying the perovskite material.

Devices and Methods of Use

Also disclosed herein are methods of use of the perovskite materials described herein.

For example, the methods can comprise using the perovskite material as a ferroelectric, transparent conducting oxide, dielectric, or a combination thereof. In some examples, the methods can comprise using the perovskite material as a photocatalyst.

Also disclosed herein are methods of using the perovskite materials described herein as a photocatalyst for photocatalytic fuel generation. The methods can comprise, for example, contacting the photocatalyst with a fuel precursor to form a mixture and illuminating the mixture with light that overlaps with at least a portion of the bandgap of the perovskite material, thereby converting the fuel precursor to a fuel.

The light can, for example, be provided by a light source. The light source can be any type of light source. Examples of suitable light sources include natural light sources (e.g., sunlight) and artificial light sources (e.g., incandescent light bulbs, light emitting diodes, gas discharge lamps, arc lamps, lasers, etc.). In some examples, the light comprises sunlight.

In some examples, the fuel precursor comprises water. The methods can, for example, comprise using the perovskite material as a photocatalyst for solar water splitting.

In some examples, the fuel comprises hydrogen. The methods can comprise, for example, using the perovskite material as a photocatalyst for photocatalytic hydrogen generation.

In some examples, the perovskite material comprises a photocatalyst that exhibits a photocatalytic rate of from 100 $\mu mol\ O_2\ h^{-1}\ g^{-1}$ to 5000 $\mu mol\ O_2\ h^{-1}\ g^{-1}$ under electromagnetic irradiation at one or more wavelengths from 230 nm to 1023 nm. In some examples, the perovskite material comprises a photocatalyst that exhibits an apparent quantum yield of from 0.3% to 50%.

In some examples, the perovskite materials can be used in various devices and articles of manufacture, such as sensors (e.g., biocompatible sensors), energy conversion devices (e.g., solar cells, fuel cells, photovoltaic cells, piezoelectric devices), charge storage devices (e.g., batteries, capacitors), electronic devices, and the like. Such articles of manufacture of devices can be fabricated by methods known in the art.

In some examples, the perovskite materials can be used as/in a piezoelectric device, wherein the piezoelectric device comprises an actuator, a motor, a sensor (e.g., a biocompatible sensor), a transducer, a high voltage source, a power source (e.g., a piezo-electric-powered pacemaker). In some examples, the methods can comprise using the piezoelectric device in ultrasound, an electric lighter, a microphone, a fuse, a guitar pickup, an inkjet printer, a loudspeaker, laser electronics, an automotive application, or a combination thereof. In some examples, the method can comprise using the piezoelectric device in an automotive application in a motor, an actuator, a power source, or a combination thereof.

Also disclosed herein are devices and articles of manufacture comprising the perovskite materials described herein. Such articles of manufacture of devices can be fabricated by methods known in the art. In some examples, the device comprises a ferroelectric device, a transparent conducting oxide device, a dielectric device, or a combination thereof. In some examples, the device comprises a sensor (e.g., a biocompatible sensor), an energy conversion device (e.g., a solar cell, a fuel cell, a photovoltaic cell, a piezoelectric device), a charge storage device (e.g., a battery, a capacitor), an electronic device, or a combination thereof.

In some examples, the device comprises a piezoelectric device, e.g., also disclosed herein are piezoelectric devices comprising the perovskite materials described herein. The piezoelectric device can, for example, comprise an actuator, a motor, a sensor (e.g., a biocompatible sensor), a transducer, a high voltage source, a power source (e.g., a piezoelectric-powered pacemaker). In some examples, the piezoelectric device comprises a power source in a pacemaker. Also described herein are methods of use of the piezoelectric devices described herein. For example, the methods can comprise using the piezoelectric device as an actuator, a motor, a sensor (e.g., a biocompatible sensor), a transducer, a high voltage source, a power source (e.g., in a piezoelectric-powered pacemaker). In some examples, the method comprises using the piezoelectric device in ultrasound, an electric lighter, a microphone, a fuse, a guitar pickup, an inkjet printer, a loudspeaker, laser electronics, an automotive application, or a combination thereof. In some examples, the method comprises using the piezoelectric device in an automotive application in a motor, an actuator, a power source, or a combination thereof.

A number of embodiments of the invention have been described. Nevertheless, it will be understood that various modifications may be made without departing from the spirit and scope of the invention. Accordingly, other embodiments are within the scope of the following claims.

The examples below are intended to further illustrate certain aspects of the systems and methods described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of measurement conditions, e.g., component concentrations, temperatures, pressures and other measurement ranges and conditions that can be used to optimize the described process.

Example 1—Metastable Semiconducting Perovskite Oxides for Visible-Light-Driven Water Oxidation Described herein is a synthetic route to thermodynamically unstable, i.e., metastable, Sn(II)-perovskite oxides that have been highly sought after as lead-free dielectrics and small bandgap semiconductors. An exchange of Sn(II) is found using a low melting $SnCl_2/SnF_2$ peritectic flux, yielding mixed A-site $(Ba_{1-x}Sn_x)ZrO_3$ and mixed A- and B-site $(Ba_{1-x}Sn_x)(Zr_{1-y}Ti_y)O_3$ (BSZT) solid solutions that exhibit high metastability, with up to 60% Sn(II) cations and a calculated reaction energy for decomposition of up to −0.3 eV atom$^{-1}$. Kinetic stabilization of the higher Sn(II) concentrations can be achieved by the high cohesive energy of the perovskite compositions containing Zr(IV) and mixed Zr(IV)/Ti(IV) cations. Red-shifted band gaps are found with increasing Sn(II) substitution, enabling the optical absorption edge to be broadly tuned from ~3.90 eV to ~1.95 eV. Percolation pathways are calculated to occur for BSZT compositions with >10% Sn(II) and >25% Ti(IV) cations. High photocatalytic rates are found for molecular oxygen production for compositions which exceed the percolation thresholds, wherein extended diffusion pathways should 'open up' across the structure and the charge carriers become delocalized rather than trapped. These results indicate that it can be important to synthetically access metastable semiconductors for the discovery of advanced optical and photocatalytic properties.

Introduction. Research into Sn(II)-containing semiconductors has garnered significant interest owing to their potential technological importance, such as within the fields of solar energy conversion, ferroelectrics and transparent conducting oxides (TCOs) (Noureldine et al. *Catal. Sci. Technol.* 2016, 6 (21), 7656-7670; Ha et al. *J. Mater. Chem. C* 2017, 5 (23), 5772-5779; Matar et al. *Chem. Phys.* 2009, 355 (1), 43-49). Intriguing optical properties of Sn(II)-containing oxides include their small semiconducting band gaps, e.g., ~1.6 to 2.0 eV, as a result of the high energy valence band formed by the filled O 2p/Sn 5 s states. These semiconductors can also exhibit a large valence band dispersion originating from the extended —O—Sn—O—Sn— connectivity and coordination geometries. Consequently, relatively low effective masses and high carrier mobilities are achievable, as highly desired in semiconductor applications such as in photovoltaics, photocatalysis and TCOs. In the field of ferroelectrics, the perovskite-type $SnTiO_3$, $SnZr_{0.5}Ti_{0.5}O_3$ and related phases have been intensely investigated as Pb-free, isoelectronic versions of $PbTiO_3$ and $PbZr_{0.5}Ti_{0.5}O_3$ (Ribeiro et al. *J. Alloys. Compds.* 2017, 714, 553-559; Gardner et al. *Reports Prog. Phys.* 2019, 82, 092501; Parker et al. *Phys. Rev. B—Condens. Matter Mater. Phys.* 2011, 84 (24), 1-7; Pitike et al. *Phys. Rev. B—Condens. Matter Mater. Phys.* 2015, 91 (3), 1-8; Campo et al. *Heliyon* 2016, 2 (5), e00112). The latter perovskite is one of the most widely used ceramics in the electronics industry because of its strong piezoelectric effect. Prior computational studies on the structure of $SnTiO_3$ have posited the occurrence of a very high ferroelectric polarization (~1.1 C·m$^2$) resulting from a stronger tetragonal distortion as compared to $PbTiO_3$ (Parker et al. *Phys. Rev. B—Condens. Matter Mater. Phys.* 2011, 84 (24), 1-7; Pitike et al. *Phys. Rev. B—Condens. Matter Mater. Phys.* 2015, 91 (3), 1-8). However, the bulk syntheses of $SnTiO_3$ and $SnZr_{0.5}Ti_{0.5}O_3$ have so far eluded attempts by many laboratories worldwide (Gardner et al. *Reports Prog. Phys.* 2019, 82, 092501).

Precious few Sn(II)-containing oxides have been synthesized as compared to other metal oxide systems. A primary reason is that, as a reactant, SnO is easily oxidized in air and disproportionates when heated under vacuum or in an inert atmosphere beginning at ~300° C. (Campo et al. *Heliyon* 2016, 2 (5), e00112; Gauzzi et al. *Inorganica Chim. Acta* 1985, 104 (1), 1-7). Recent synthetic studies have demonstrated that low-temperature ion exchange reactions with Sn(II)-halides, e.g., $SnF_2$ and/or $SnCl_2$, can provide an effective synthetic approach. Flux reaction conditions involve the use of relatively low-melting salts, e.g., metal chlorides or sulfates, as an effective medium to react metal oxides (Boltersdorf et al. *CrystEngComm*, 2015, 17, 2225-2241). Its use has enabled the preparation of a growing number of new compounds which exhibit limited stability or metastability such as $Sn_2TiO_4$ (O'Donnell et al. *J. Electrochem. Soc.* 2019, 166 (5), H3084-H3090; Boltersdorf et al. *Chem. Mater.* 2017, 28, 8876-8889), or in related systems such as $Cu_2Ta_4O_{11}$ and $Cu_2Nb_8O_{21}$ (King et al. *Cryst. Grow. Des.* 2015, 15, 552-558; Choi et al. *ACS Nano* 2013, 7(2), 1699-1708). The recent examples with Sn(II) cations include the first high-purity syntheses of $Sn_2TiO_4$, representing the first known Sn(II)-titanate, as well as $SnTiO_3$ with an ilmenite structure-type (Diehl et al. *Chem. Mater.* 2018, 30 (24), 8932-8938). The former phase was synthesized starting from either $K_2Ti_2O_5$ or $Ba_2TiO_4$, e.g., $Ba_2TiO_4(s)+2 SnClF(s) \rightarrow Sn_2TiO_4(s)+2 BaClF(s)$. The exothermicity of salt formation drives the net reaction, with a large enthalpy of formation of BaClF from SnClF of about −1041 kJ mol-1 (O'Donnell et al. *J. Electrochem. Soc.* 2019, 166 (5), H3084-H3090). Thus, this approach leverages the exothermic formation of stable salts to surmount the thermodynamic barriers to forming metastable compounds.

Elucidation of the underlying chemistry that determines the synthesizability of metastable compounds currently represents a highly active research field. The fundamental principles and limits are not well understood and have historically remained primarily empirical in nature. One hypothesized criterion is that the synthesizability of a metastable compound can be determined based upon its excess enthalpy above the ground state, such as within a range of ~0.05 to 0.20 eV atom$^{-1}$ above the convex hull in composition space. More recently, computational investigations have demonstrated that a greater cohesive energy enables the synthesis of compounds with a higher metastability (Sun et al. *Sci. Adv.* 2016, 2 (11), e160025; Aykol et al. *Sci. Adv.* 2018, 4, eaaq0148). Perovskite oxides represent a large family of compounds with relatively high cohesive energies that are a function of the A-site and B-site cations (Goudochnikov et al. *J. Phys.: Condens. Matter* 2007, 19, 176201). A tuning of the mixed A/A'-site and B/B'-site cations in the form of solid solutions can be used as a chemical lever to manipulate their relative stability. Perovskite compounds can serve as a testbed for exploring the underlying principles of the synthesizability of metastable phases, such as for those containing Sn(II) cations. For example, the perovskite-type $SnTiO_3$ and $SnZrO_3$, as well as the $Sn(Zr_{0.5}Ti_{0.5})O_3$ solid solution, are all calculated to be highly metastable, by ~0.4 eV atom$^{-1}$ to 0.5 eV atom$^{-1}$, with respect to decomposition to the simpler oxides or to the ilmenite structure. Prior studies have found that the highest amount of Sn(II) that can be incorporated into the A-site of any titanate or zirconate perovskite is limited to less than about 10 mol % (Suzuki et al. *Phys. Rev. B—Condens. Matter Mater. Phys.* 2012, 86 (6), 8-11; Suzuki et al. *Jpn. J. Appl. Phys.* 2013, 52 (9 PART2), 7-10).

Described herein is the substitution of the destabilizing Sn(II) cation into the perovskite $BaZrO_3$, $BaTiO_3$, and the $Ba(Zr_{1-y}Ti_y)O_3$ solid solutions using low temperature reactions with a salt flux and yielding highly metastable compositions. Perovskites are obtained in bulk form with the highest known amounts of Sn(II) cations and that push the extreme limits of metastability that can be synthesized. The compounds were comprehensively characterized and found to exhibit cubic perovskite structures that become increasingly metastable with both the Sn(II) and Zr(IV) concentrations. Their kinetic stabilization is attributable to the large cohesive energy of the underlying perovskite structure as well as the low reaction temperatures and short reaction time which mitigate ion diffusion and segregation. Their bandgap sizes and photocatalytic activities for water oxidation also show promising properties for solar energy conversion.

Experimental Methods.

Flux Synthesis of $Ba(Zr_{1-y}Ti_y)O_3$ Perovskites. The $BaTiO_3$, $BaZrO_3$ and the $Ba(Zr_{1-y}Ti_y)O_3$ (BZT; y=0.25, 0.5, 0.75) solid solutions were synthesized in a molten NaCl—KCl salt flux. The reactants $BaCO_3$ (0.0055 mol-Alfa Aesar, 99.8%), $TiO_2$ (0.0025 mol-J. T. Baker, >99%), and $ZrO_2$ (0.0025 mol-Beantown Chemical, 99.5%) were ground together for 20 min in the desired stoichiometry with a 10% mole excess of $BaCO_3$. After mixing, an equimolar mixture of NaCl (0.05 mol) and KCl (0.05 mol) were prepared with a salt-to-product ratio of 20:1 that was ground for 20 min. The reactants were loaded into an alumina crucible and heated to 1100° C. at a rate of 10° C. min$^{-1}$ and soaked for 24 hours before cooling to room temperature. Products were washed multiple times in deionized water and centrifuged in order to remove any salt flux and dried overnight at 80° C.

Flux-Assisted Synthesis of $(Ba_{1-x}Sn_x)(Zr_{1-y}Ti_y)O_3$ (BSZT). The BSZT phases (y=0.0, 0.25, 0.5, 0.75, 1.0; x=0.1 to 1.0 in increments of 0.1) were synthesized via flux-assisted reactions using the $BaTiO_3$, $BaZrO_3$, BZT and SnClF reactants. The perovskites (0.001 mol) were ground together with an appropriate stoichiometric amount of $SnCl_2$ (Alfa Aesar, 99% min) and $SnF_2$ (Alfa Aesar, 97.5%) under an argon atmosphere for 20 min and then loaded into a fused-silica tube and placed under dynamic vacuum. The evacuated and flame-sealed tubes were then heated to 350° C. at a rate of 12° C. min$^{-1}$, held for 12 hours, and radiatively cooled to room temperature. Products were thoroughly washed and centrifuged with deionized water to remove any unreacted salt flux or side products, and dried overnight at 80° C.

Characterization. Powder diffractograms for all samples were collected using a Rigaku R-Axis Spider using Cu Kα radiation (λ=1.54056 Å) from a sealed tube X-ray source (40 kV, 36 mA) and a curved image-plate detector. High resolution data sets for selected samples were collected on a PANalytical Empyrean X-Ray diffractometer operating with Cu Kα radiation (45 kV, 40 mA) with a step size of 0.0131 2θ and a 300 sec count time per step. X-ray total scattering measurements for reduced pair distribution function (PDF) analysis were collected at the 11-ID-C Beam line of the Advanced Photon Source (APS) at Argonne National Laboratory. A wavelength of 0.1173 Å was used for 2D data collection acquired using a Perkin-Elmer area detector. The reduction of the 2D data to 1D was performed using FIT2d software. The pair distribution function data was obtained from the 1D data using PDFgetx3 software. Neutron diffraction data were collected on the POWGEN (Beam line 11-A) time-of-flight (TOF) Diffractometer at the Spallation Neutron Source (SNS) at Oak Ridge National Laboratory during cycle run 2019-B. Polycrystalline samples (~2 g) were sealed in cylindrical vanadium sample cans and data were collected at 298 K and 20 K. A neutron beam with a wavelength of 1.5 Å at 60 Hz was used with a detector ~2.0-4.7 m away from the sample. The crystal structures were refined for both the X-ray and neutron diffraction data by the Rietveld method.

UV-vis diffuse reflectance measurements were taken using a Shimadzu UV-3600 equipped with an integrating sphere. The background was a pressed barium sulfate disc. The data were transformed using the Kubelka-Munk, F(R), function (Simmons et al. *Appl. Opt.* 1976, 15 (4), 951). Since F(R) is also equal to k/s, where k and s are the absorption and scattering coefficients, the bandgap sizes can be extracted via Tauc plots of $(F(R) \times hv)^n$ versus photon energy for the allowed direct (n=2) and indirect (n=½) transitions. The direct and indirect bandgap energies were determined by extrapolating the linear portion of the Tauc plots to the baseline fit. SEM images and elemental analysis were performed using a JOEL SM 6010LA scanning electron microscope with a 20 kV accelerating voltage with a secondary electron imaging detector along with a JOEL EDS Silicon Drift Detector.

Suspended Particle Photocatalysis Measurements. Photocatalytic rates for molecular oxygen were measured without the addition of a cocatalyst using similar conditions as reported previously (Boltersdorf et al. *ACS Catal.* 2013, 3, 2943-2953; McLamb et al. *Cryst. Growth Des.* 2013, 13, 2322-2326). The photocatalytic rates of molecular oxygen production were measured using an outer-irradiation type fused-silica reaction cell with a Xe arc-lamp and photon flux of ~200 mW cm-2. The Xe arc lamp was equipped with an IR filter and samples were irradiated with ultraviolet-visible light (λ>230 nm) and visible light (λ>400 nm). Suspensions were degassed via sonication with flowing nitrogen. Photocatalytic rates were measured in an aqueous 0.05 M $AgNO_3$ solution (Alfa Aesar, 99.9%). Measurements were taken every 10 min for 90 min to obtain the initial rate, and then every 30 min thereafter. Gas production was measured volumetrically, and the products were identified via gas chromatography.

Electronic Structure Calculations. Total energy and electronic structure calculations were performed using 4×4×4 supercells of $(Ba_{1-x}Sn_x)(Zr_{1-y}Ti_y)O_3$ using density functional theory methods as implemented in the Vienna Ab initio Simulation Package (ver. 4.6) (Kresse et al. *Comput. Mater. Sci.* 1996, 6 (1), 15-50; Perdew et al. *Phys. Rev. Lett.* 1996, 77, 3865). Calculations were performed using Perdew-Burke-Ernzerhof functionals in the generalized gradients approximation using the projector augmented wave method. The Brillouin-zone was automatically sampled using a 2×2×2 Monkhorst-Pack grid. The cubic phase of BZT and BSZT were simulated using the cubic perovskite Pm-3m space group with lattice constants determined from the experimental values.

Decomposition energies of the Sn(II)-containing BSZT perovskites were calculated following a previously reported procedure by Hautier et al. (Emery et al. *Scient. Data* 2017, 4, 170153; Hautier et al. *Phys. Rev. B—Condens. Matter Mater. Phys.* 2012, 85, 155028), wherein the use of total energy calculations have been demonstrated to accurately predict reaction energies of ternary metal oxides from their binary oxides. Total energies are calculated at 0 K using density-functional theory methods and then used to accurately calculate the overall reaction energy. As all reactants and products are solids, entropic contributions are assumed negligible at room temperature. For example, the decomposition of the Sn(II)-free oxides to their constituent binary oxides, i.e., $Ba(Zr_{1-y}Ti_y)O_3 \rightarrow BaO+(1-y) ZrO_2+y TiO_2$, were calculated to be thermodynamically unfavorable ($\Delta E_{decomp}$ of up to ~0.3 eV atom$^{-1}$). The reaction energy of decomposition of the metastable Sn(II)-containing perovskites were calculated according to the observed decomposition products, as described below. In nearly all cases the Sn(II)-containing perovskites decomposed via the formation of SnO and stoichiometric amounts of $Ba(Zr_{1-y}Ti_y)O_3$, $TiO_2$ and $ZrO_2$. Total energies of the binary oxides and the specific BZT/BSZT compositions were calculated, as well as taken or cross-checked with the Open Quantum Materials Database (Saal et al. JOM 2013, 65, 1501-1509).

Results and Discussion.

Figure 31:
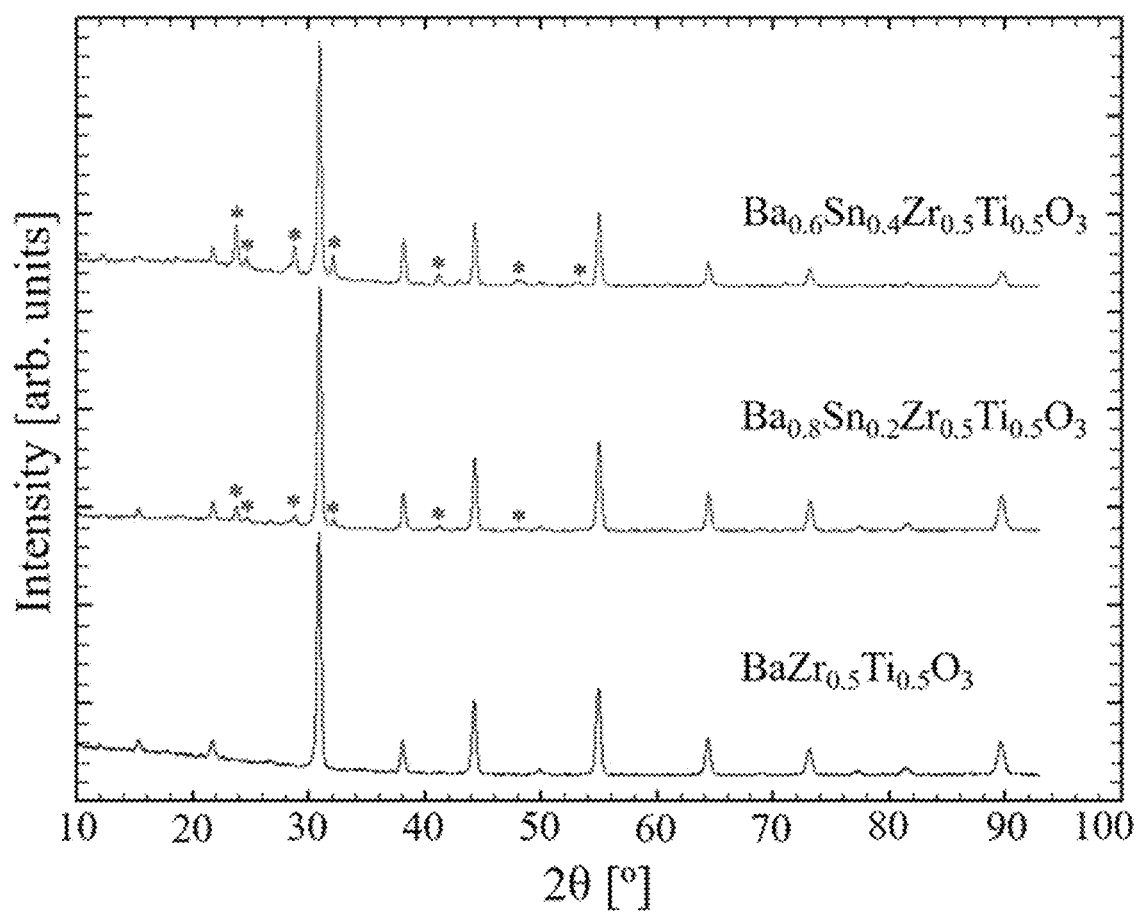
FIG. 31. PXRD of pre-washed $Ba_{1-x}Sn_xZr_{0.5}Ti_{0.5}O_3$ (*—BaClF). PXRD shows expected formation of BaClF in increasing amounts with increasing Sn(II) concentration.
Figure 32:
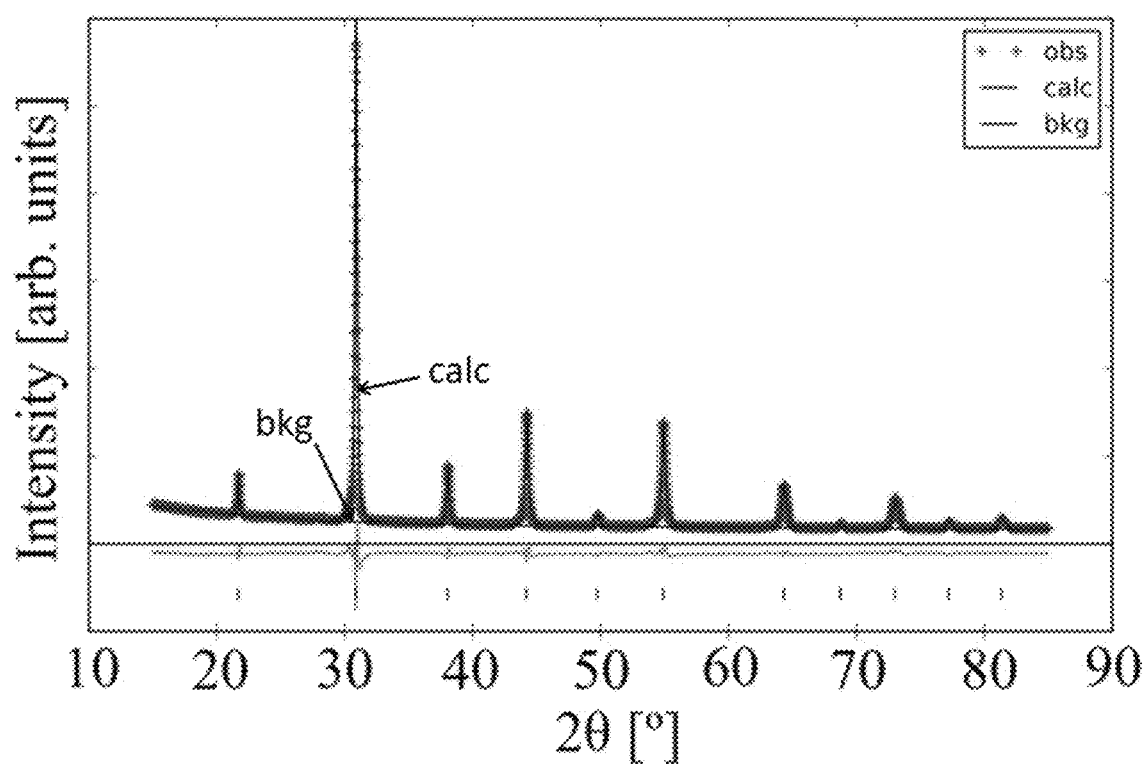
FIG. 32. Plot of Rietveld refinement results of X-ray diffraction data for $Ba(Zr_{0.5}Ti_{0.5})O_3$.
Figure 33:
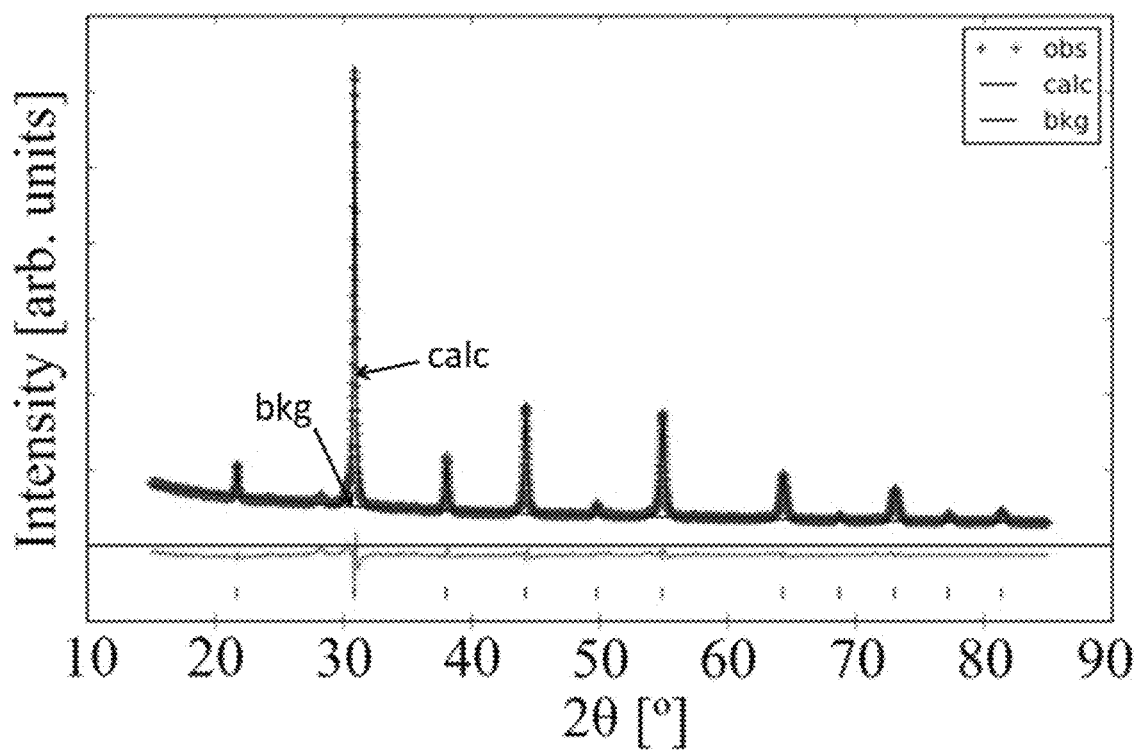
FIG. 33. Plot of Rietveld refinement results of X-ray diffraction data for $(Ba_{0.8}Sn_{0.2})(Zr_{0.5}Ti_{0.5})O_3$.
Figure 34:
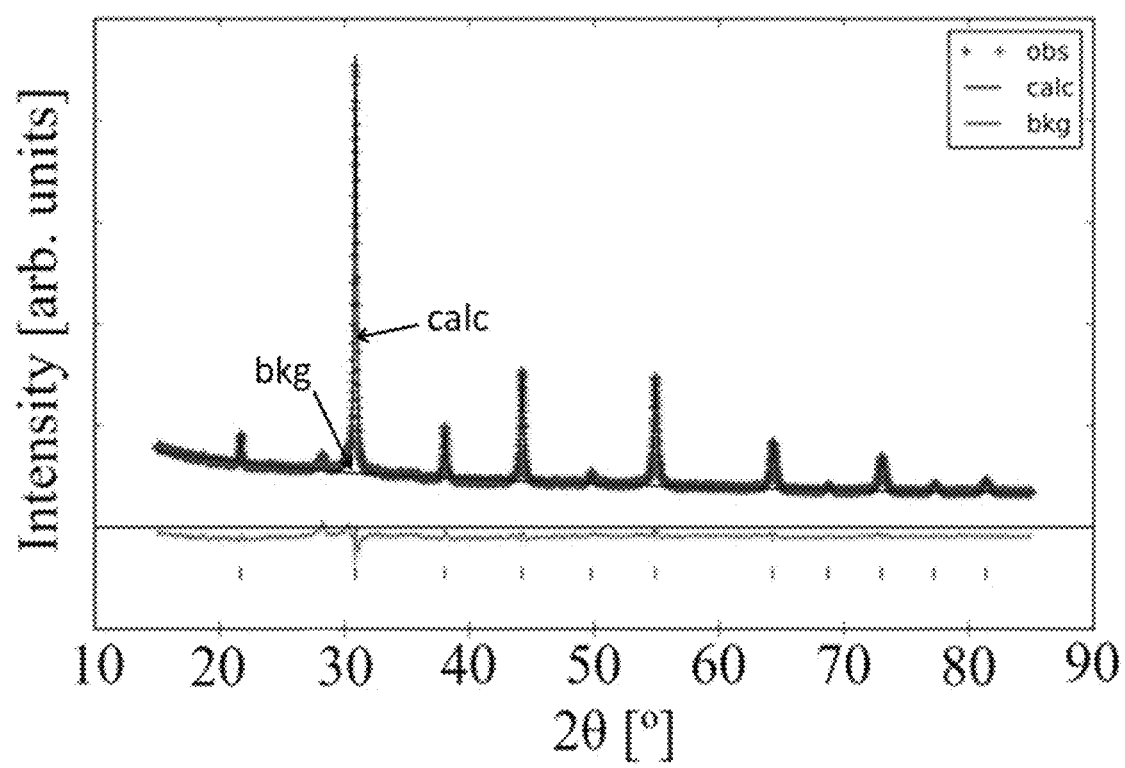
FIG. 34. Plot of Rietveld refinement results of X-ray diffraction data for $(Ba_{0.6}Sn_{0.4})(Zr_{0.5}Ti_{0.5})O_3$.
Figure 35:
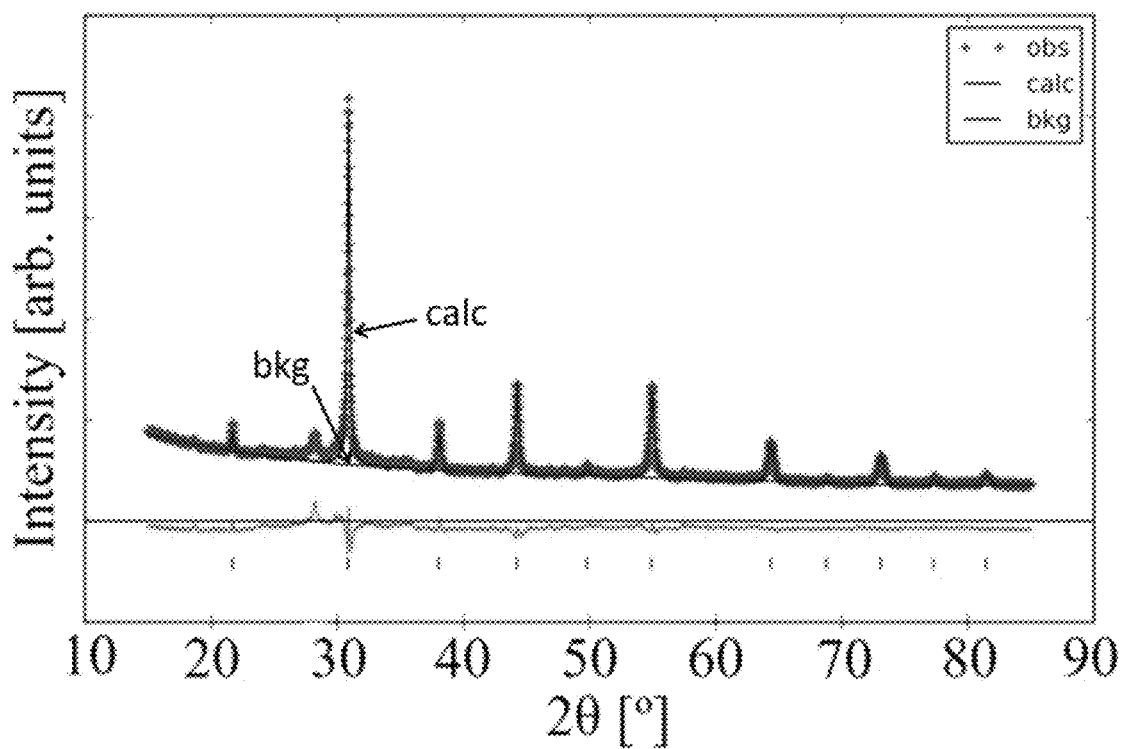
FIG. 35. Plot of Rietveld refinement results of X-ray diffraction data for $(Ba_{0.4}Sn_{0.6})(Zr_{0.5}Ti_{0.5})O_3$.

Synthesis and Structural Characterization. Low temperature flux-assisted reactions were investigated to prepare Sn(II)-containing perovskites starting from the barium perovskites, i.e., $Ba(Zr_{1-y}Ti_y)O_3+x\ SnClF \rightarrow (Ba_{1-x}Sn_x)(Zr_{1-y}Ti_y)O_3+x\ BaClF$. While pure $BaTiO_3$ is tetragonal, all other BZT compositions in this study (i.e., ≥25% Zr, y=0.75) crystallize in the cubic polymorph at room temperature. The $Ba(Zr_{1-y}Ti_y)O_3$ compositions were reacted with SnClF to produce $(Ba_{1-x}Sn_x)(Zr_{1-y}Ti_y)O_3$ (BSZT) in increasing increments of 0.1 (x=0.0 to 1.0). Bulk powder XRD data for each composition are shown in FIG. 26 to FIG. 30. Representative powder XRD data of unwashed BSZT shows the formation of increasing amounts of BaClF, shown in FIG. 31. The highest percentage of Sn(II) substitution into $BaTiO_3$, i.e., $(Ba_{1-x}Sn_x)TiO_3$, that maintained the perovskite structure was only ~10%, or x=0.1. Higher amounts of Sn(II) substitution resulted in the formation of the ilmenite-type $SnTiO_3$ in increasing amounts. With a small increase of 25% Zr on the B-site, i.e., $Ba(Zr_{0.25}Ti_{0.75})O_3$, closer to ~40% Sn(II) could be substituted before the formation of the ilmenite-type $SnTiO_3$ phase. Starting from pure $BaZrO_3$, the maximum amount of Sn(II) substitution in $(Ba_{1-x}Sn_x)ZrO_3$ is further significantly increased to ~50% to 60%, or x=0.5 to 0.6. This represents the highest Sn(II) concentration ever reported on the A-site for a perovskite-type structure. No evidence is found for an ilmenite-type '$SnZrO_3$' composition at higher amounts. Instead, higher amounts of Sn(II) in the loaded reaction stoichiometry result in increasing diffraction peaks for a SnO impurity.

Figure 36:
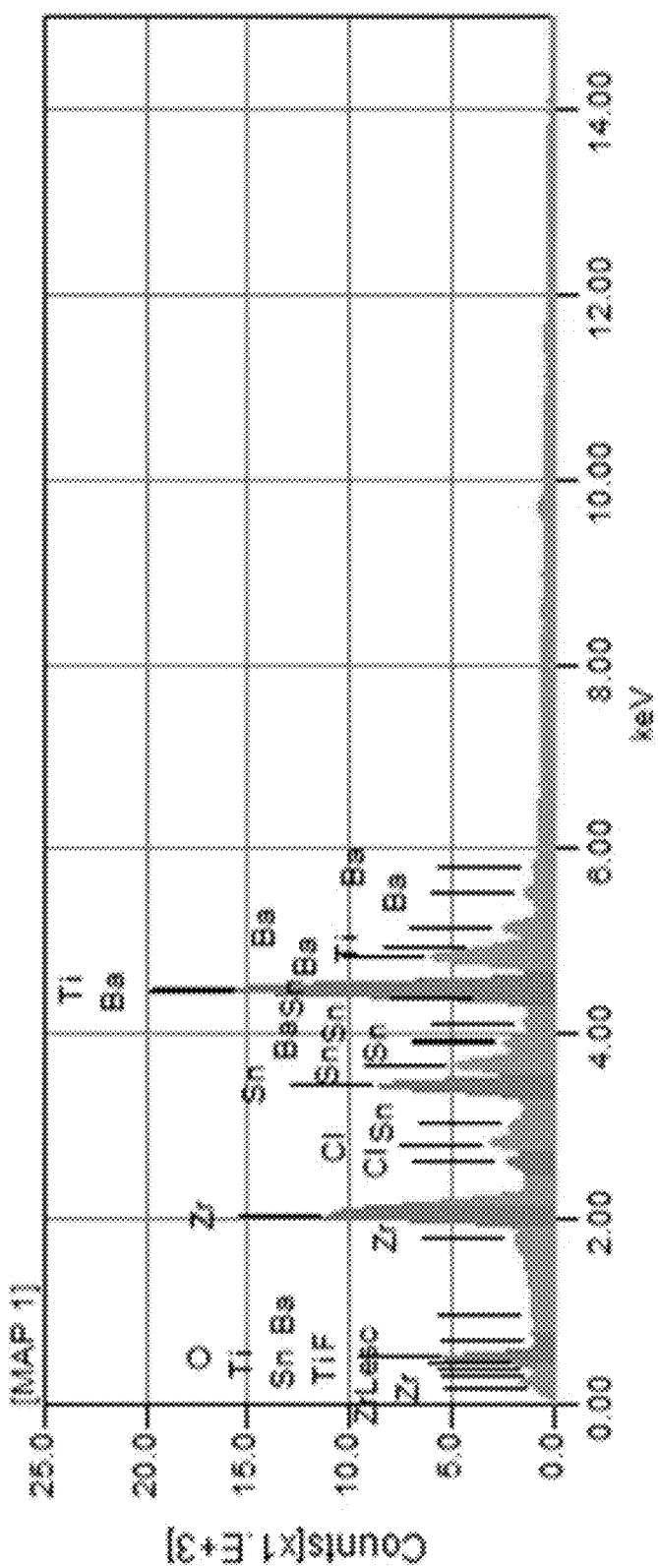
FIG. 36. Representative EDS spectra for BSZT samples. $Ba_{0.6}Sn_{0.4}Zr_{0.5}Ti_{0.5}O_3$— shows detection limit level amount of Cl, likely as a result of trace amounts of BaClF that were not completely washed.
Figure 37:
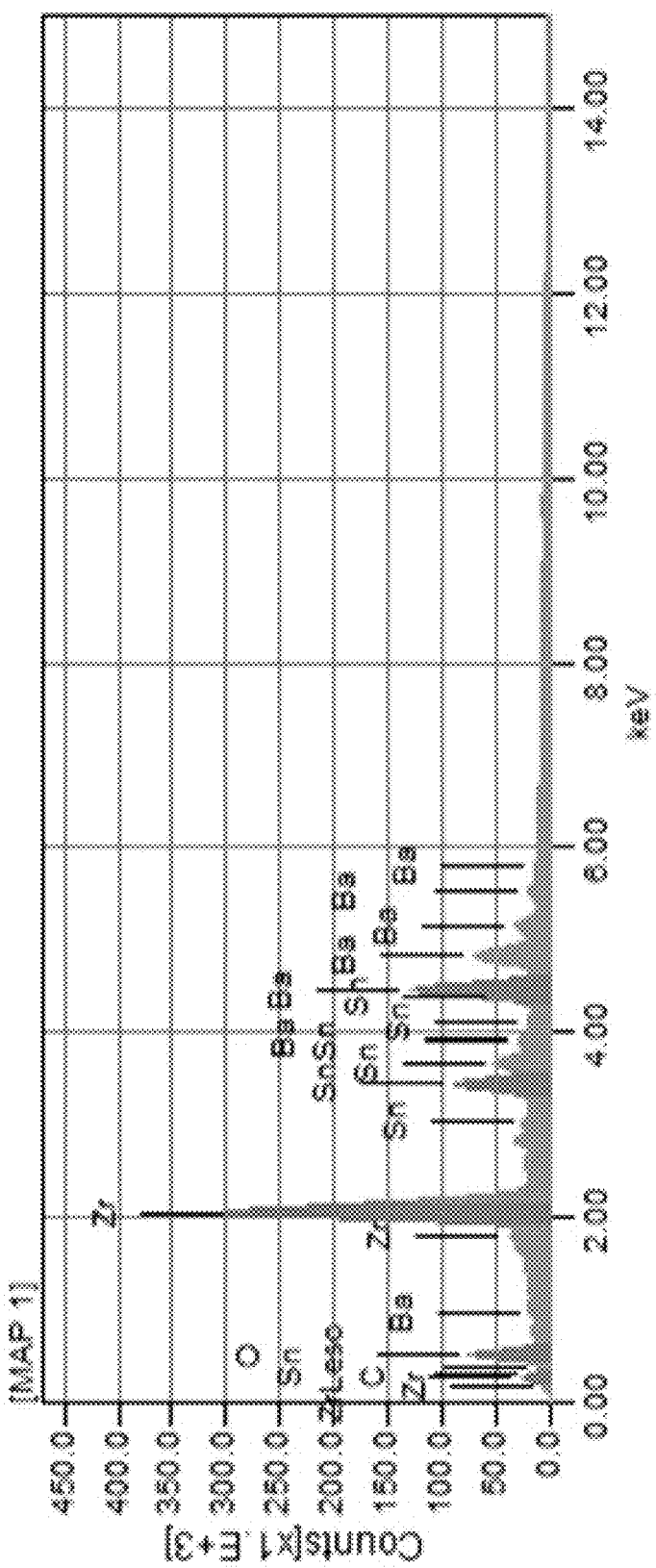
FIG. 37. Representative EDS spectra for BSZT samples. $Ba_{0.6}Sn_{0.4}ZrO_3$— no signals for any remaining BaClF. C in both samples is from the C-tape.

A high amount of Sn(II) substitution was also possible in the 50:50 $BaZrO_3$—$BaTiO_3$ solid solution, i.e., $Ba(Zr_{0.5}Ti_{0.5})O_3$, with up to ~60% Sn(II) cations and the maintenance of the cubic perovskite structure. The powder XRD data show a minor amount of $ZrO_2$ impurity in all samples beyond ~30% Sn(II) concentration. However, the EDS data of the washed samples (FIG. 36 and FIG. 37), listed in Table 1, show that up to ~60% Sn(II) can be incorporated into the structure. The compositional trends in the EDS data are also consistent with the loaded stoichiometries of each reaction, within a standard deviation of ~5%. In order to probe these structures in more detail, high resolution X-ray diffraction data were collected for $Ba(Zr_{0.5}Ti_{0.5})O_3$ and for its compositions with 20%, 40% and 60% Sn(II) cations to perform Rietveld refinements, FIG. 32-FIG. 35. High resolution neutron diffraction data were also collected for the latter two compositions for Rietveld analysis, FIG. 1-FIG. 4. Results of the Rietveld refinements of the $(Ba_{1-x}Sn_x)(Zr_{0.5}Ti_{0.5})O_3$ compositions, Table 2, most closely matched with a cubic perovskite structure, with weighted residuals of ~3 to 6%.

TABLE 1

Selected results from Energy Dispersive Spectroscopy (EDS) data taken on the BSZT phases.

| Composition | Ba [mol %] | Sn [mol %] | x = |
|---|---|---|---|
| $Ba_{0.8}Sn_{0.2}Zr_{0.25}Ti_{0.75}O_3$ | 22.98 | 5.52 | 0.19 |
| $Ba_{0.8}Sn_{0.2}Zr_{0.5}Ti_{0.5}O_3$ | 24.60 | 4.96 | 0.17 |
| $Ba_{0.6}Sn_{0.4}Zr_{0.5}Ti_{0.5}O_3$ | 17.32 | 10.84 | 0.38 |
| $Ba_{0.4}Sn_{0.6}Zr_{0.5}Ti_{0.5}O_3$ | 12.33 | 15.20 | 0.55 |
| $Ba_{0.8}Sn_{0.2}Zr_{0.75}Ti_{0.25}O_3$ | 23.34 | 5.68 | 0.20 |
| $Ba_{0.8}Sn_{0.2}ZrO_3$ | 10.15 | 2.38 | 0.19 |
| $Ba_{0.6}Sn_{0.4}ZrO_3$ | 13.58 | 7.07 | 0.34 |

TABLE 2

Results of Rietveld refinements of neutron and X-ray diffraction data at room temperature for selected compositions of the $(Ba_{1-x}Sn_x)(Zr_{0.5}Ti_{0.5})O_3$ solid solution.

| Loaded Composition | $BaZr_{0.5}Ti_{0.5}O_3$ (0% Sn) | $Ba_{0.8}Sn_{0.2}Zr_{0.5}Ti_{0.5}O_3$ (20% Sn) | $Ba_{0.6}Sn_{0.4}Zr_{0.5}Ti_{0.5}O_3$ (40% Sn) | | $Ba_{0.4}Sn_{0.6}Zr_{0.5}Ti_{0.5}O_3$ (60% Sn) | |
|---|---|---|---|---|---|---|
| Radiation | X-ray | X-ray | X-ray | Neutron | X-Ray | Neutron |
| Lattice Constant [Å] | 4.095(1) | 4.097(0) | 4.095(9) | 4.0922(8) | 4.093(7) | 4.090(8) |
| R(w) [%] | 4.67 | 3.55 | 3.25 | 5.69 | 3.67 | 5.90 |
| Ba fraction | 1.0* | 0.82(3) | 0.61(9) | 0.58(8) | 0.400* | 0.400* |
| Sn fraction | 0.0* | 0.17(7) | 0.38(1) | 0.41(2) | 0.600* | 0.600* |
| Zr fraction | 0.47(3) | 0.44(5) | 0.47(7) | 0.45(1) | 0.47(0) | 0.48(5) |
| Ti fraction | 0.52(7) | 0.55(5) | 0.52(3) | 0.54(9) | 0.53(0) | 0.51(5) |

*Value was fixed during refinement.

The lattice constant was found to slightly contract with Sn(II) substitution and ranged from 4.095(1) Å to 4.090(8) Å. In addition, the refined elemental distributions of Ba/Sn cations on the A-site and the Zr/Ti cations on the B-site were consistent with the loaded reaction stoichiometries. Neutron diffraction data were also taken at 20 K for the 40% and 60% Sn(II) perovskites in order to probe whether a low-temperature phase transition occurs, similar to that known for $BaTiO_3$ and the $Ba(Zr_{1-y}Ti_y)O_3$ solid solution. Both compositions remained well matched to the cubic perovskite structure at low temperatures, FIG. 3 and FIG. 4 and Table 3, with only a small contraction of the lattice constant.

TABLE 3

Selected Rietveld refinement results of neutron diffraction data at 20K.

| | $Ba_{0.6}Sn_{0.4}Zr_{0.5}Ti_{0.5}O_3$ | $Ba_{0.4}Sn_{0.6}Zr_{0.5}Ti_{0.5}O_3$ |
|---|---|---|
| Lattice Constant [Å] | 4.0871(4) | 4.0905(7) |
| Refined Weighted Residuals [%] | 7.030 | 7.629 |
| Refined Ba | 0.600* | 0.400* |
| Refined Sn | 0.400* | 0.600* |
| Refined Zr | 0.45(3) | 0.51(5) |
| Refined Ti | 0.54(7) | 0.485(1) |

*Value was fixed during refinement.

Figure 5:
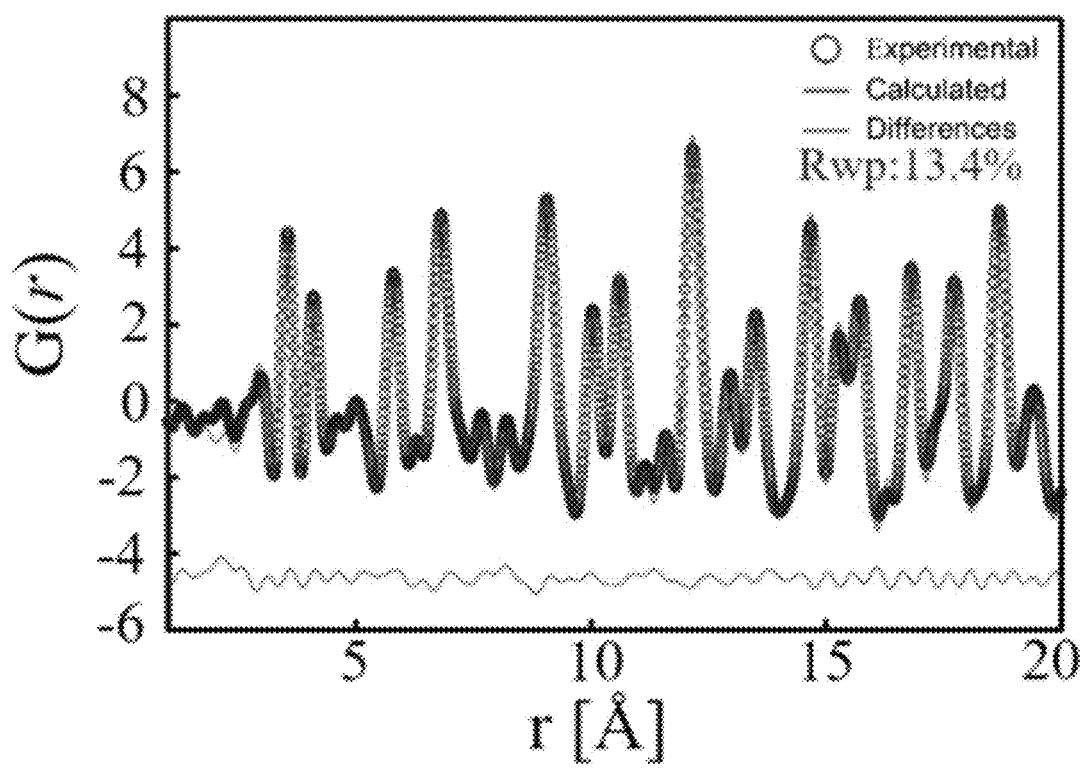
FIG. 5. Pair distribution function refinement for $Ba(Zr_{0.5}Ti_{0.5})O_3$. The cubic perovskite model was used for refinement.
Figure 6:
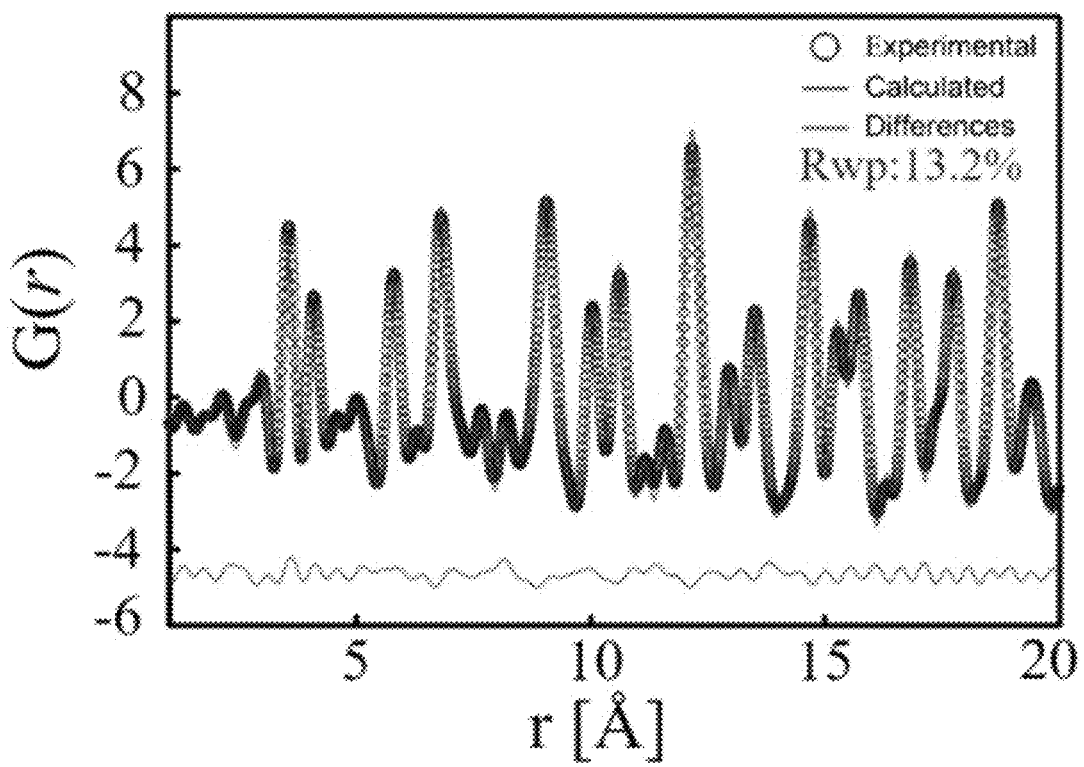
FIG. 6. Pair distribution function refinement for $(Ba_{0.8}Sn_{0.2})(Zr_{0.5}Ti_{0.5})O_3$. The cubic perovskite model was used for refinement.
Figure 7:
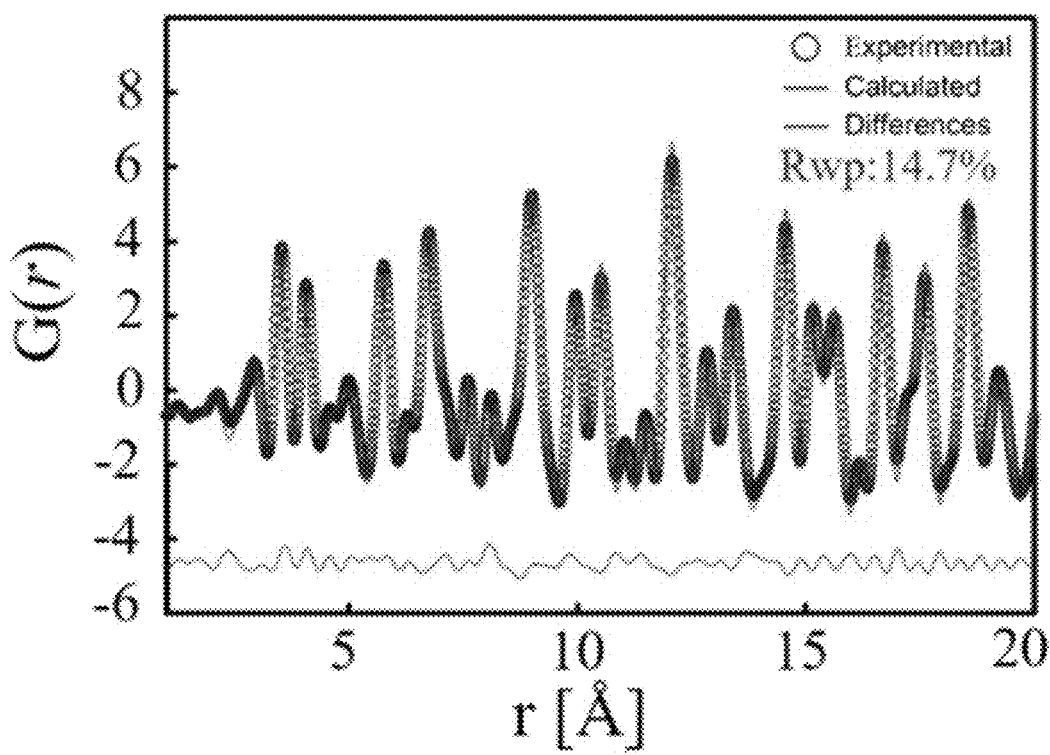
FIG. 7. Pair distribution function refinement for $(Ba_{0.8}Sn_{0.2})(Zr_{0.25}Ti_{0.75})O_3$. The cubic perovskite model was used for refinement.
Figure 8:
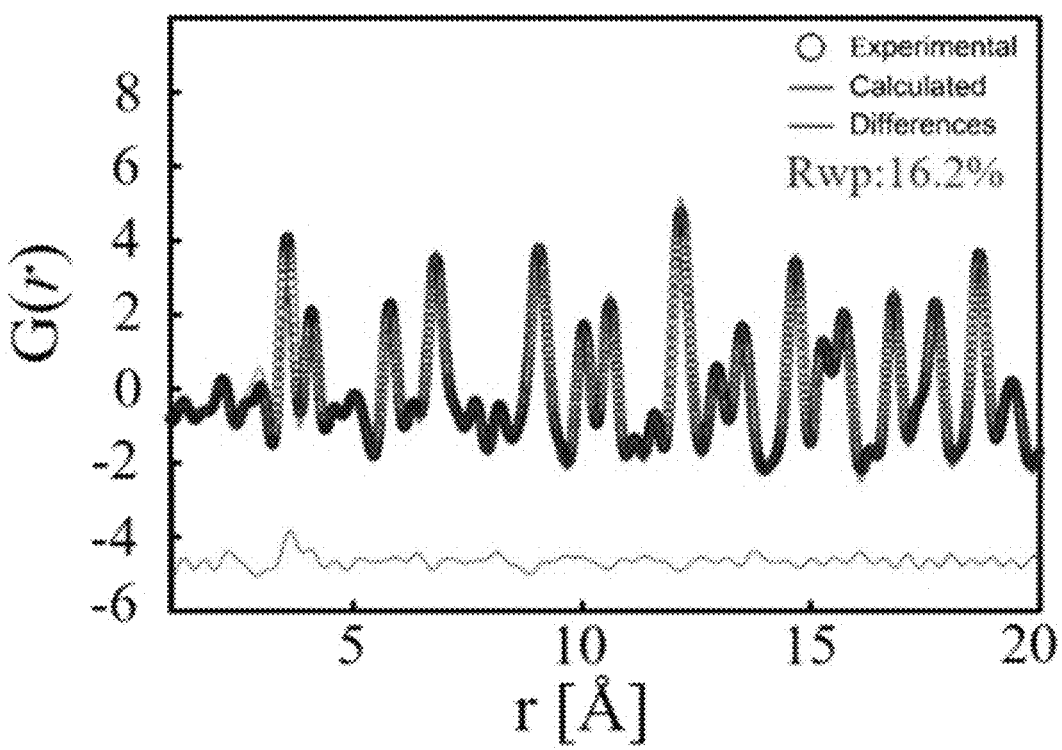
FIG. 8. Pair distribution function refinement for $(Ba_{0.4}Sn_{0.6})(Zr_{0.5}Ti_{0.5})O_3$. The cubic perovskite model was used for refinement.
Figure 9:
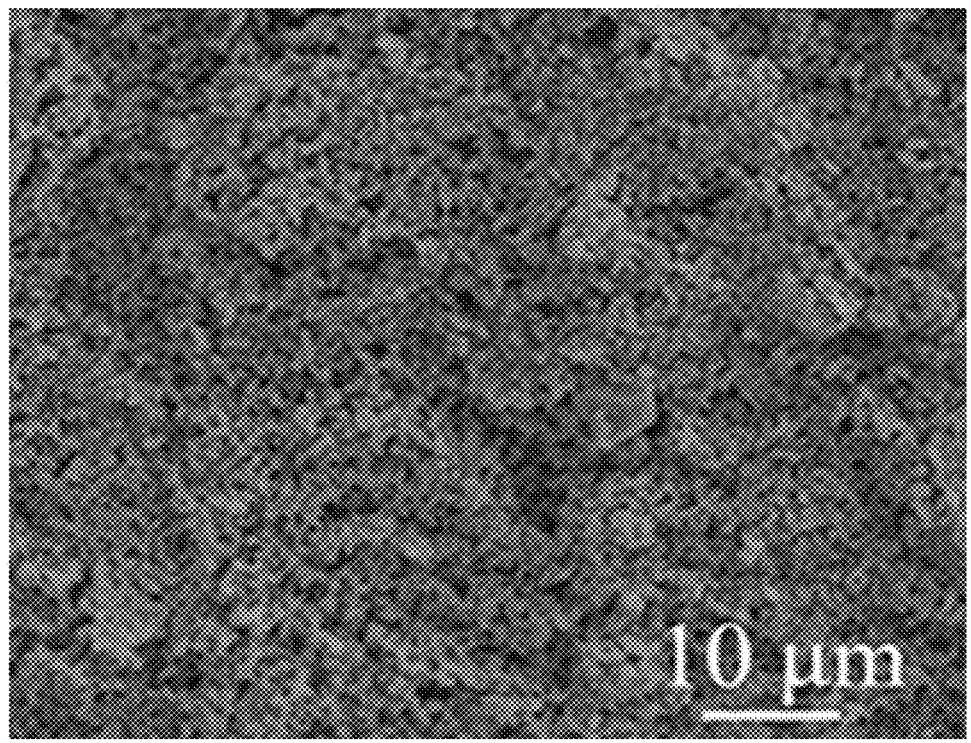
FIG. 9: SEM image of $Ba(Zr_{0.5}Ti_{0.5})O_3$. Particle sizes ranged ~0.5 to 2.0 μm.
Figure 10:
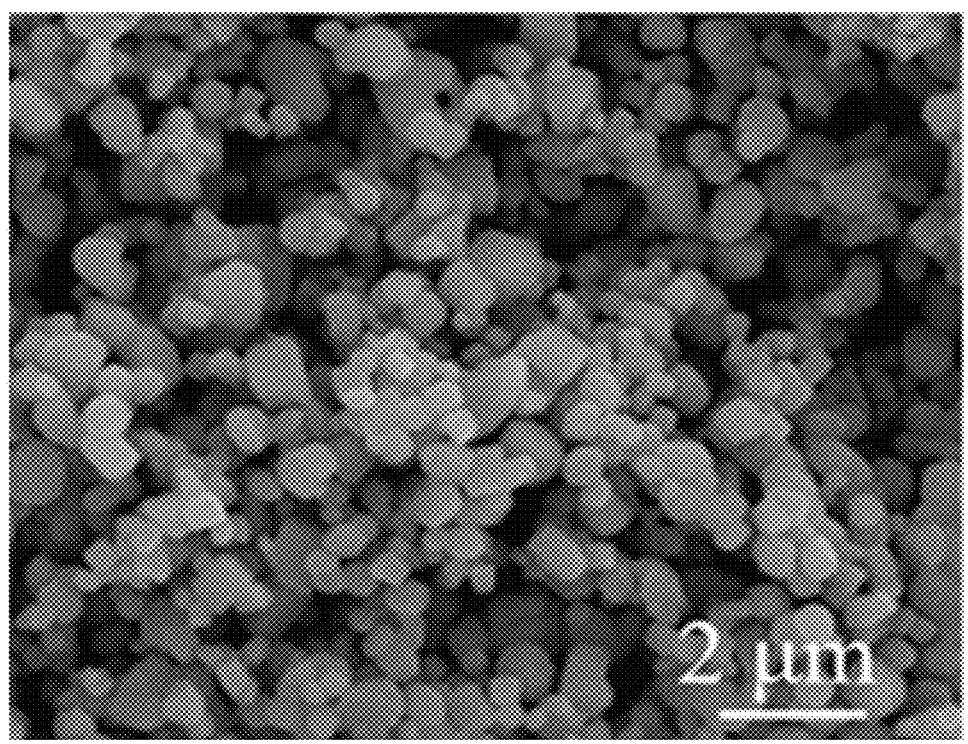
FIG. 10: SEM image of $Ba(Zr_{0.5}Ti_{0.5})O_3$. Particle sizes ranged ~0.5 to 2.0 μm.
Figure 38:
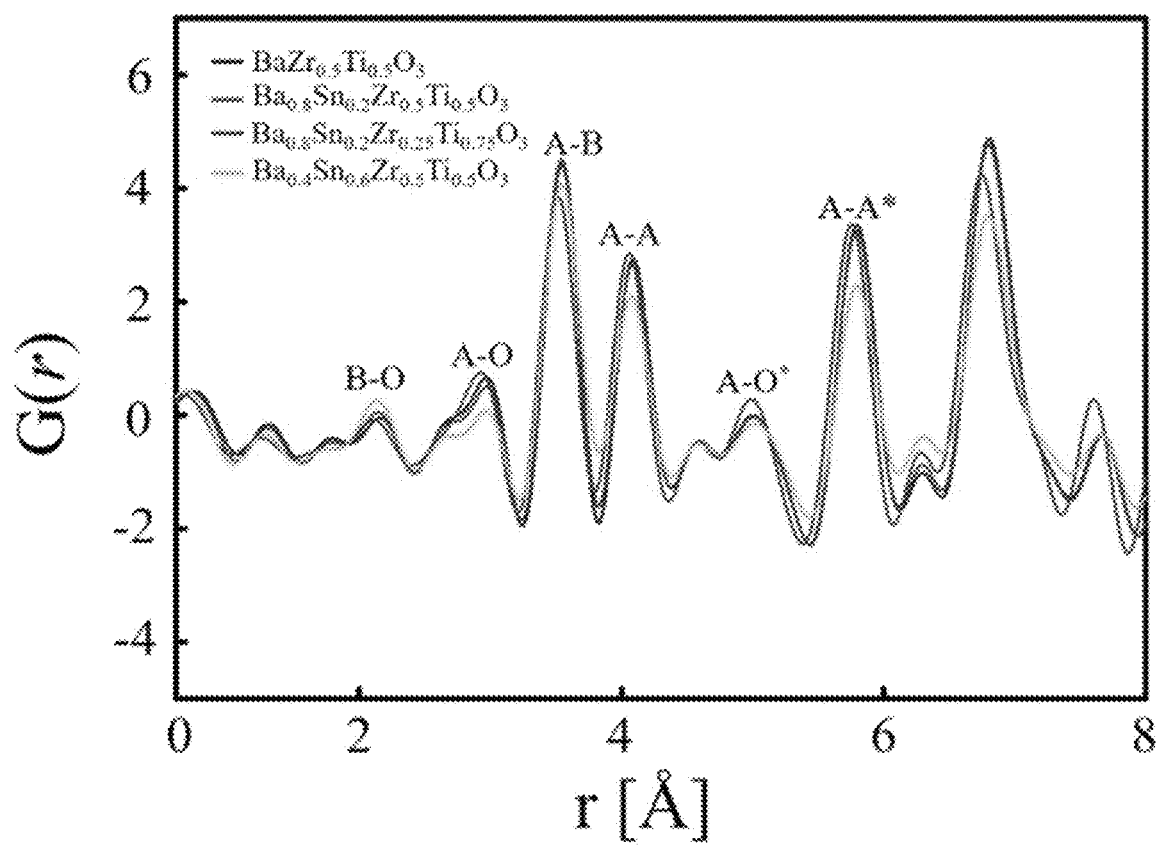
FIG. 38. Overlay of pair distribution function data for $Ba(Zr_{0.5}Ti_{0.5})O_3$, $(Ba_{0.8}Sn_{0.2})(Zr_{0.5}Ti_{0.5})O_3$, $(Ba_{0.4}Sn_{0.6})(Zr_{0.5}Ti_{0.5})O_3$, and $(Ba_{0.8}Sn_{0.2})(Zr_{0.25}Ti_{0.75})O_3$. The profiles for the Sn(II) substituted phases match with cubic $Ba(Zr_{0.5}Ti_{0.5})O_3$. The data shows shifting consistent with lattice constant trends.
Figure 39:
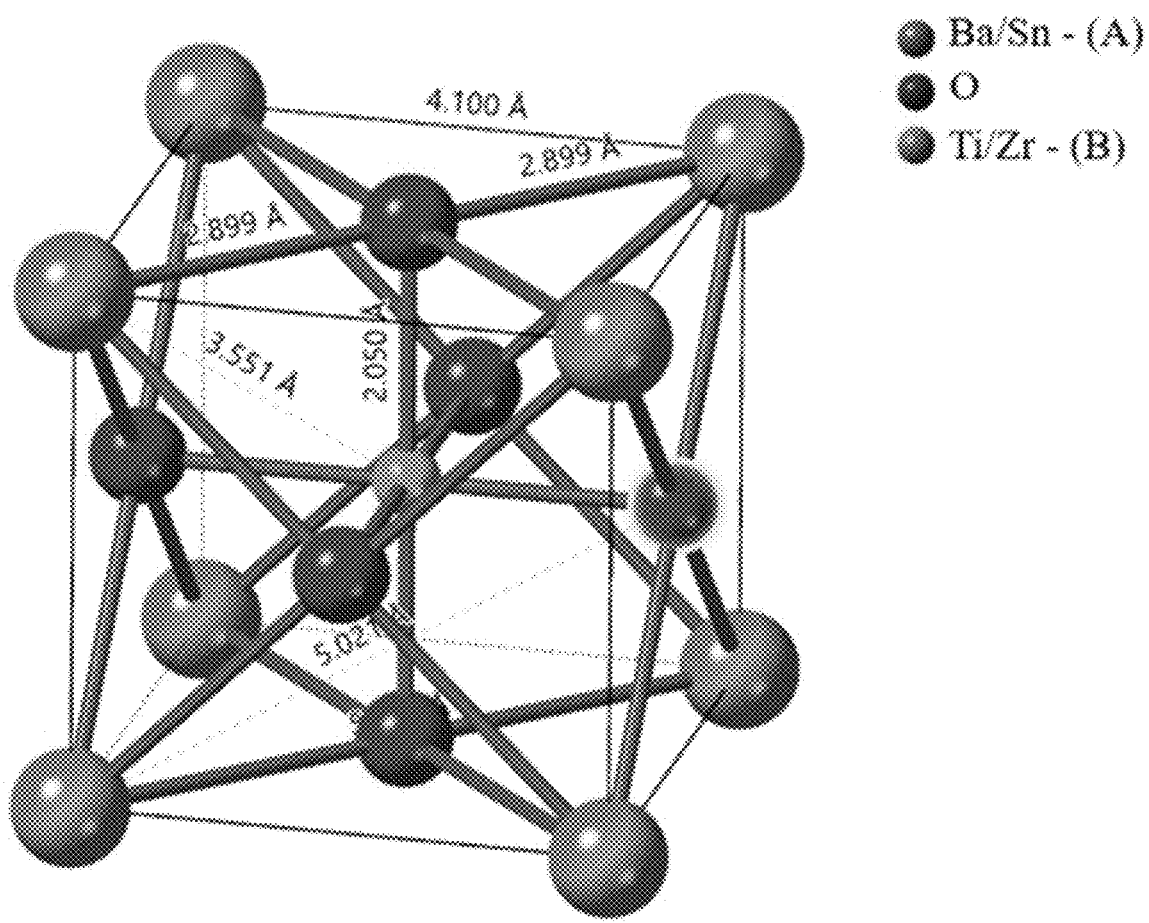
FIG. 39. Cubic BSZT model with interatomic distances.

The BSZT compositions all surprisingly indicated the lack of a stereoactive lone pair on the Sn(II) cation. The Sn(II) cation can undergo an atomic displacement similar to the isoelectronic Pb(II) cation in the well-known PZT compositions. All previously reported crystal structures of binary and ternary Sn(II)-containing oxides have shown the presence of a stereoactive lone pair. In order to investigate the local structures, total X-ray scattering data were collected and the pair distribution functions (PDFs) were calculated for representative compositions (Proffen et al. *Zeitschriftfur Krist.* 2004, 219 (3), 130-135; Aksel et al. *Phys. Rev. B—Condens. Matter Mater. Phys.* 2013, 87 (10), 1-10). These data are shown in FIG. 5, FIG. 6, and FIG. 8 for $Ba(Zr_{0.5}Ti_{0.5})O_3$ with 0%, 20% and 60% Sn(II) substitution, respectively, and in FIG. 7 for $Ba(Zr_{0.25}Ti_{0.75})O_3$ with 20% Sn(II) substitution. The refinement results confirmed the long-range structures and contracting unit cell dimensions of these cubic perovskite structures. Shown in FIG. 38-FIG. 39, the calculated pair distribution functions at small distances (r<8.0 Å) show that all interatomic distances are consistent with the cubic perovskite model. However, the local structure (r<3.0 Å) for the 60% Sn(II) perovskite indicated some small deviations from the ideal cubic symmetry, FIG. 8, that has so far not been adequately modeled in the refinements as it requires more model complexity. Preliminary results show that the introduction of a pseudocubic structure, which allows for small distortions to be modeled in the Sn(II) position along the [001] and [111] directions, can improve the Rietveld refinement results for the 60% Sn composition when compared with the cubic lattice structure.

The stereoactivity of the post-transition metal oxides has been explained by the Revised Lone Pair Model (RLP) previously (Walsh et al. *Chem. Soc. Rev.* 2011, 40 (9), 4455-4463). In brief, metal cations with electron configurations $d^{10}s^2p^0$ in groups 13-16 can exhibit stereoactive lone pairs arising from the mixing of the unoccupied cation p-orbitals with the anti-bonding cation s and anion p states. Strong lone-pair activity occurs when the cation s and anion p states are close in energy, such as for Sn(II) cations bonded to oxygen. Additionally, the net electronic stabilization must be greater than the energetic penalty from the decrease in coordination. Based on the Revised Lone Pair model, the lack of lone pair activity appears unusual. However, the mixed A/A'-site of BSZT contains both Ba(II) and Sn(II), of which only the latter has the requisite electronic configuration to favor a structural distortion. A greater Sn(II) substitution on the A-site would lead to a larger concerted electronic driving force to give the distorted perovskite structure, as predicted for $SnTiO_3$ or $Sn(Zr_{0.5}Ti_{0.5})O_3$. The lack of a lone-pair can thus be attributed to the energetic penalty for the decrease in coordination of both Ba and Sn(II) being greater than the electronic stabilization afforded to Sn(II) in a distorted environment.

Figure 11:
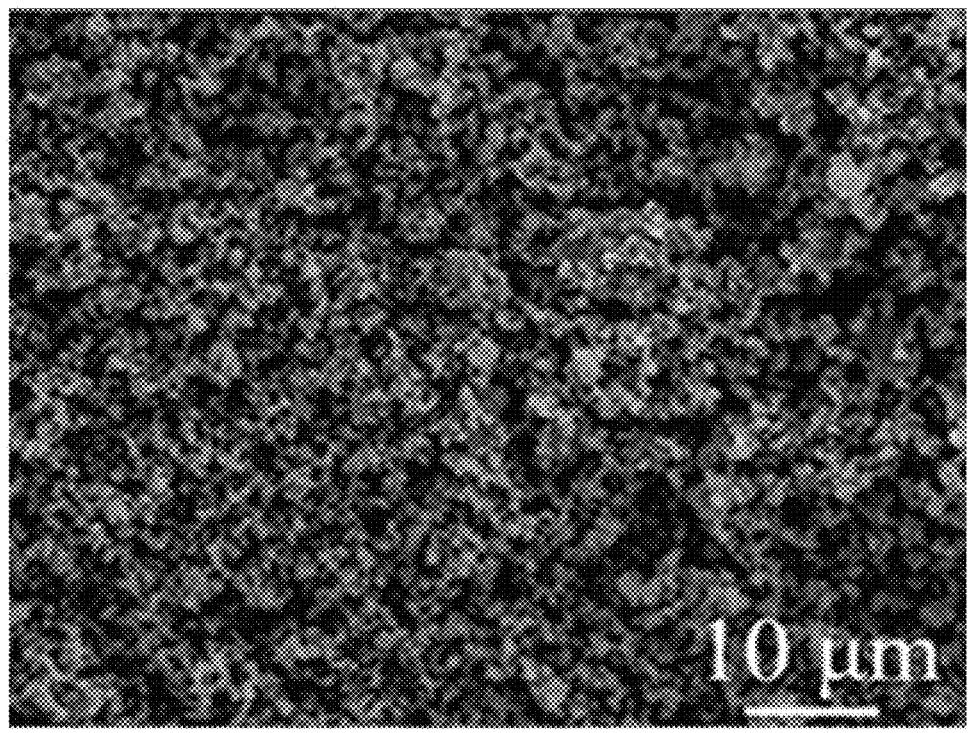
FIG. 11: SEM image of $(Ba_{0.8}Sn_{0.2})(Zr_{0.5}Ti_{0.5})O_3$. Particle sizes ranged ~0.5 to 2.0 μm.
Figure 12:
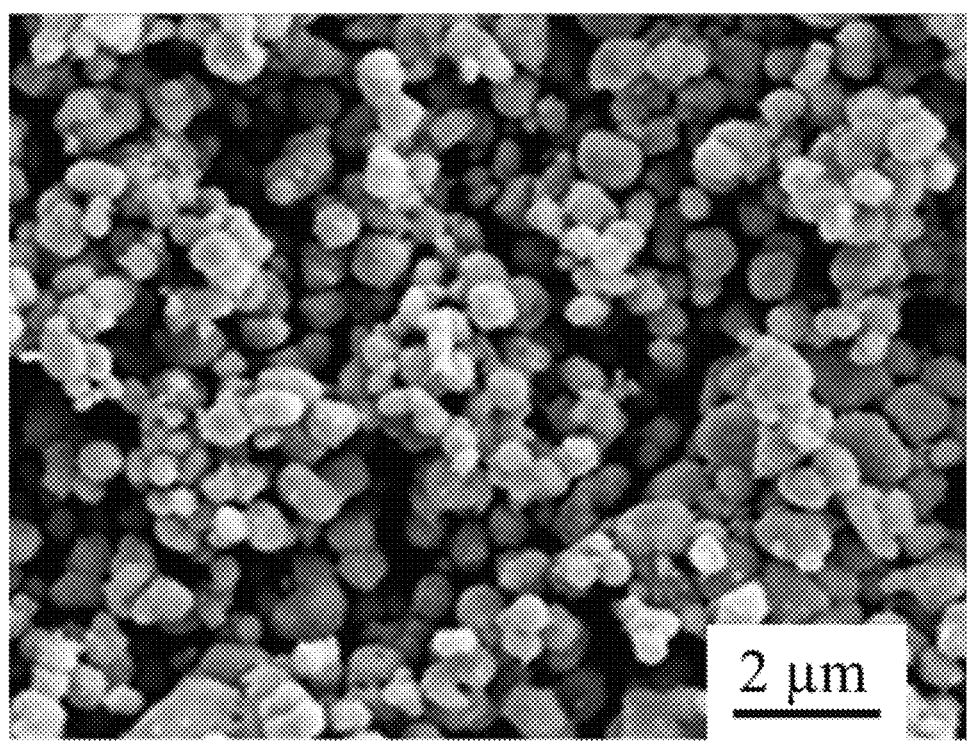
FIG. 12: SEM image of $(Ba_{0.8}Sn_{0.2})(Zr_{0.5}Ti_{0.5})O_3$. Particle sizes ranged ~0.5 to 2.0 μm.
Figure 13:
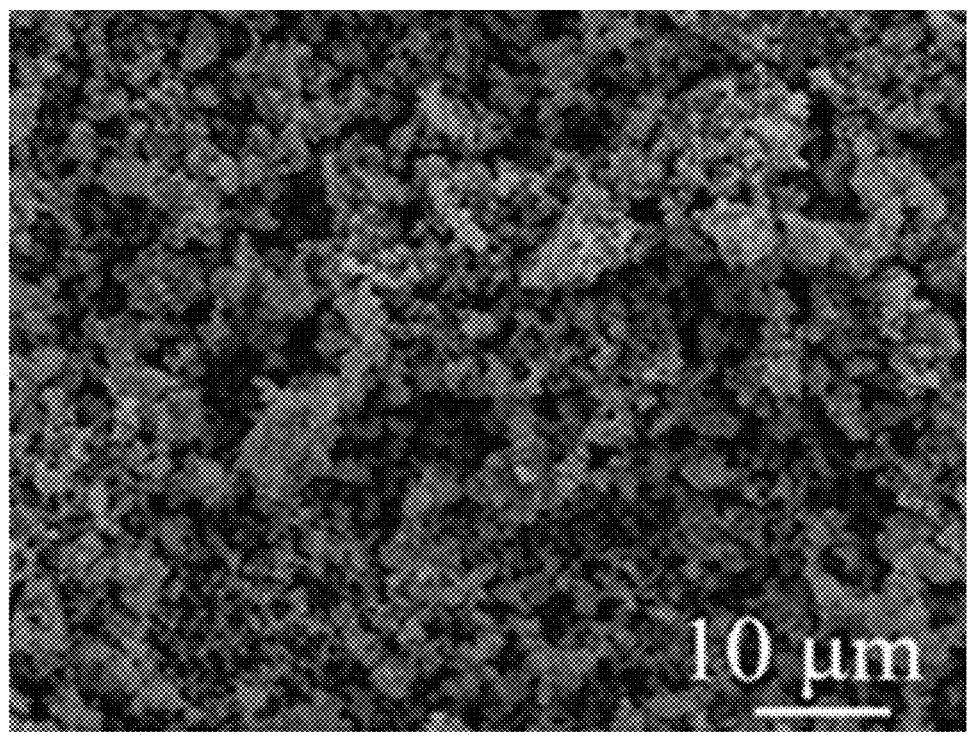
FIG. 13: SEM image of $(Ba_{0.6}Sn_{0.4})(Zr_{0.5}Ti_{0.5})O_3$. Particle sizes ranged ~0.5 to 2.0 μm.
Figure 14:
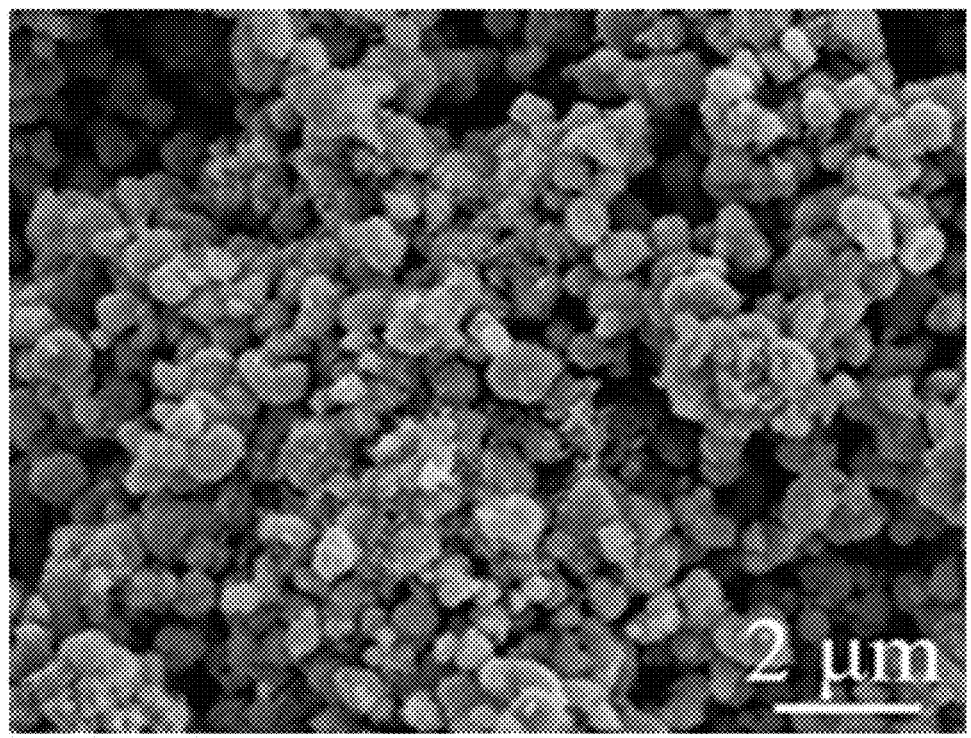
FIG. 14: SEM image of $(Ba_{0.6}Sn_{0.4})(Zr_{0.5}Ti_{0.5})O_3$. Particle sizes ranged ~0.5 to 2.0 μm.
Figure 15:
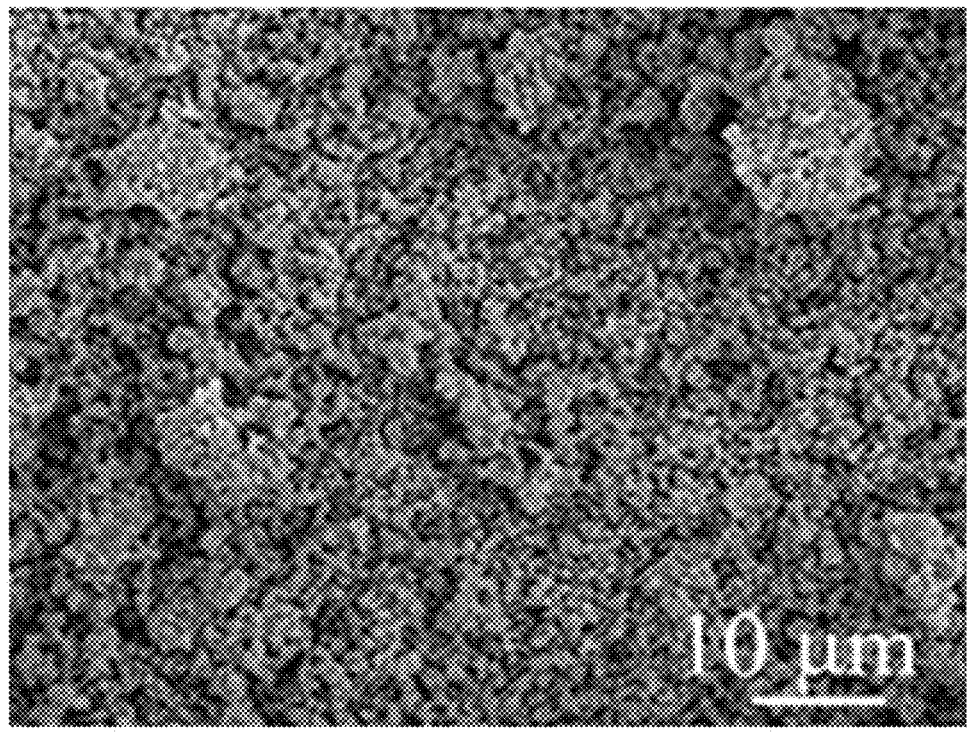
FIG. 15: SEM image of $(Ba_{0.4}Sn_{0.6})(Zr_{0.5}Ti_{0.5})O_3$. Particle sizes ranged ~0.5 to 2.0 μm.
Figure 16:
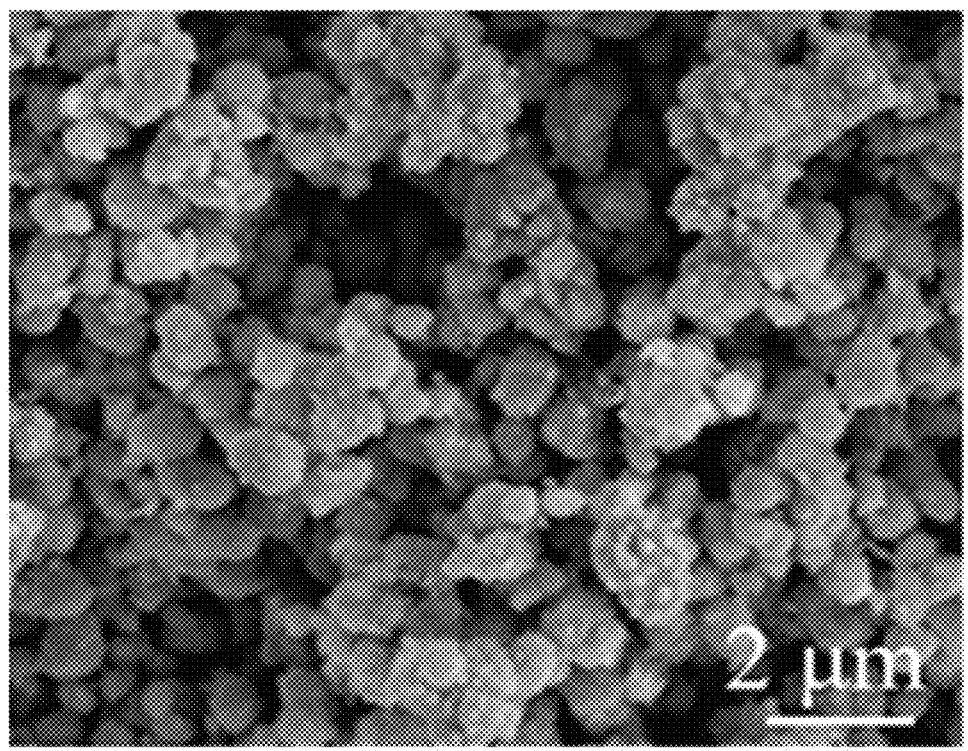
FIG. 16: SEM image of $(Ba_{0.4}Sn_{0.6})(Zr_{0.5}Ti_{0.5})O_3$. Particle sizes ranged ~0.5 to 2.0 μm.

Particle Sizes and Morphologies. Scanning electron microscope (SEM) images were taken to measure the particle sizes and morphologies of the perovskite products both before and after the substitution of the Sn(II) cations. This was used to probe for evidence of whether the perovskite structure had melted and re-crystallized, or alternatively, if a relatively 'soft' Sn(II)-exchange had occurred to give the products without it melting. Shown in FIG. 9-FIG. 16 are the SEM images taken for the $(Ba_{1-x}Sn_x)(Zr_{0.5}Ti_{0.5})O_3$ family of compounds, for 0%, 20%, 40%, and 60% Sn(II) substitution. The crystallite particles of the unsubstituted $Ba(Zr_{0.5}Ti_{0.5})O_3$, FIG. 9 and FIG. 10, exhibited an almost cubic-shaped morphology with smooth surfaces and sizes ranging from ~0.5 to 2 μm. The perovskite with 20% Sn substitution, FIG. 11 and FIG. 12, showed the same general particle sizes but with slightly more irregular morphologies with roughened surfaces. The perovskite samples with 40% and 60% Sn(II) substitution showed the same trend.

Significantly, no evidence was found for particle coarsening or agglomerating that would indicate the melting or dissolution of the $Ba(Zr_{0.5}Ti_{0.5})O_3$ particles during the substitution of the Sn(II) cations. The incorporation of Sn(II) cations can even be achieved to some extent without the breakup of the particles, up to about 20% Sn(II). However, the addition of larger amounts of Sn(II) significantly fractures the particles owing to the difference in ionic size between the Ba(II) and Sn(II) cations, which have crystal radii of ~1.35 Å and ~0.95 Å, respectively. As the crystal radius of 12-fold coordinate Sn(II) is unknown, the preceding values for 6-fold coordination are used only as a common reference point to compare the relative crystal radii of Ba and Sn(II). The trends in the measured Ba:Sn molar ratios from energy dispersive X-ray spectroscopy were consistent with the results of the structure refinements and the loaded reaction stoichiometries, Table 1.

Thermodynamic Calculations of Stability. To probe the stability of the perovskite oxides, total energies of each of the compositions were obtained from DFT results available in the Open Quantum Materials Databases. Some solid solutions were also calculated for consistency using the VASP software package. Prior studies by Hautier et al. have demonstrated that total energies can be used to determine the reaction energies for the formation of metal oxides at 0 K (Hautier et al. *Phys. Rev. B—Condens. Matter Mater. Phys.* 2012, 85, 155028). The calculated reaction energies have been shown to be accurate within a mean deviation of close to zero and a standard deviation of only ~24 meV atom$^{-1}$, i.e., much smaller than the reaction energies. The reaction energies, e.g., $AO+BO_2 \rightarrow ABO_3$, indicate the extent of metastability ($\Delta E_{decomp}>0$) of the perovskite toward decomposition to a more stable polymorph or the binary oxides. Stabilities were estimated as a function of both A/A'- and B/B'-site compositions.

Figure 40:
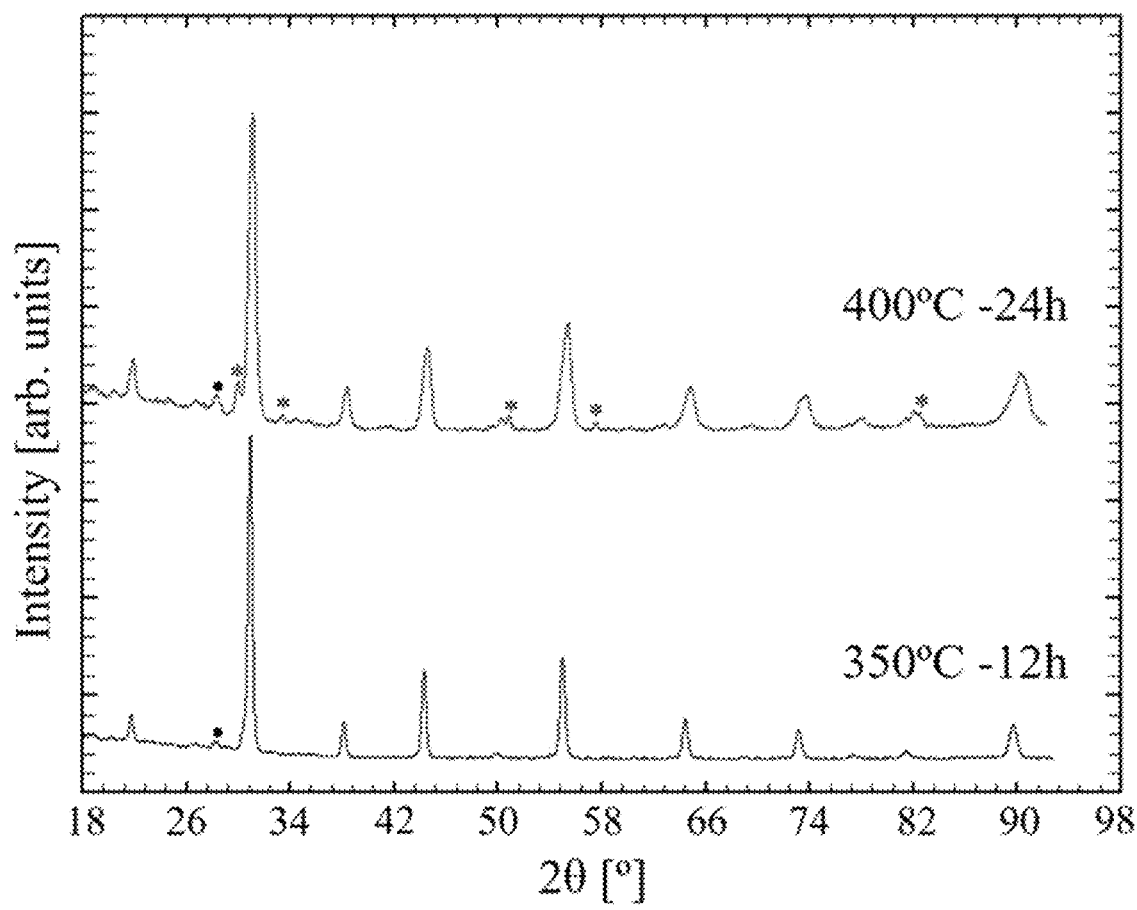
FIG. 40. X-ray powder diffractograms for $Ba_{0.7}Sn_{0.3}Zr_{0.5}Ti_{0.5}O_3$ synthesized at 350° C. for 12 h and 400° C. for 24 h (•—$ZrO_2$, *—SnO). $Ba_{0.7}Sn_{0.3}Zr_{0.5}Ti_{0.5}O_3$, which could be successfully synthesized with only a small $ZrO_2$ side product, shows significant formation of SnO and $ZrO_2$ with increased reaction temperature and time.
Figure 41:
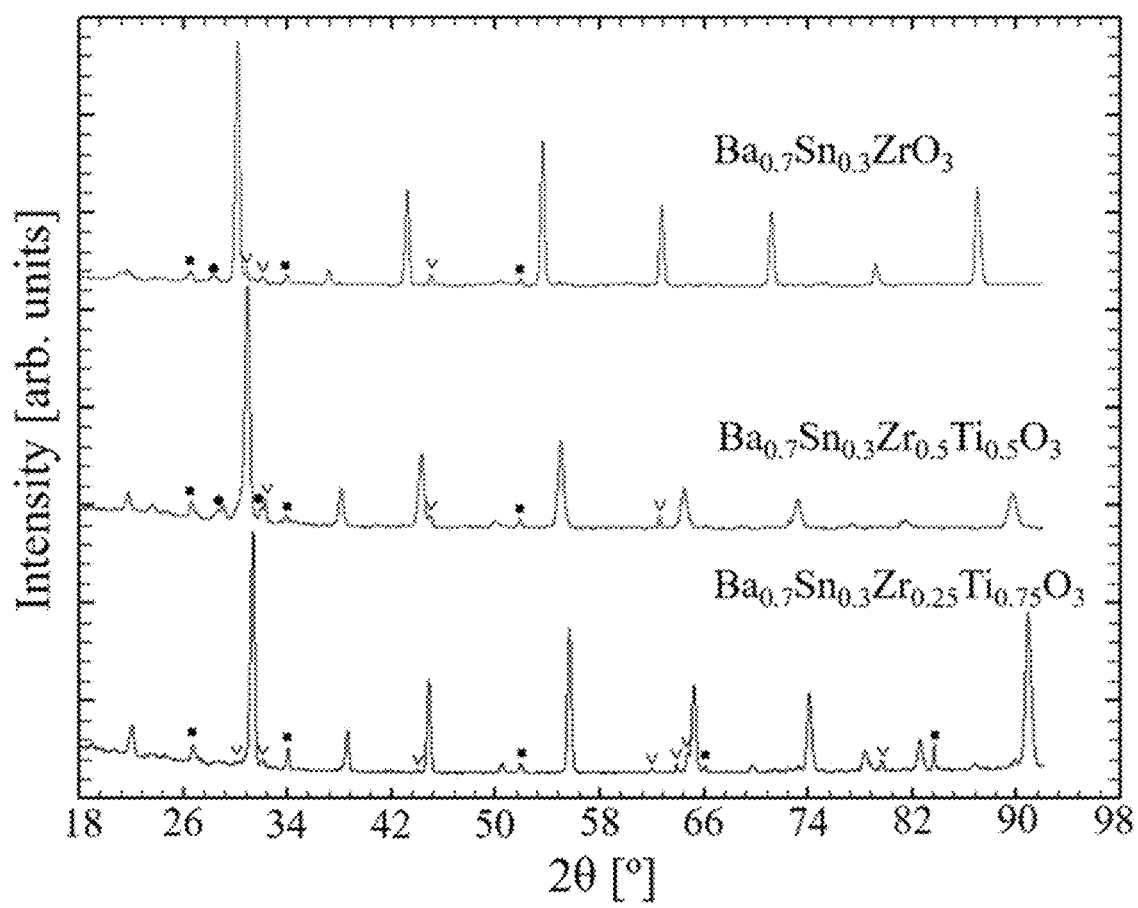
FIG. 41. X-ray powder diffractograms of products after $Ba_{0.7}Sn_{0.3}Zr_{0.25}Ti_{0.75}O_3$, $Ba_{0.7}Sn_{0.3}Zr_{0.5}Ti_{0.5}O_3$, and $Ba_{0.7}Sn_{0.3}ZrO_3$ were heated to 800° C. for 8 h under vacuum (•—$ZrO_2$, •—$SnO_2$, V-Sn). The BSZT phases all showed decomposition to binary oxides ($SnO_2$ and Sn are SnO disproportionation products) with a perovskite phase remaining.
Figure 42:
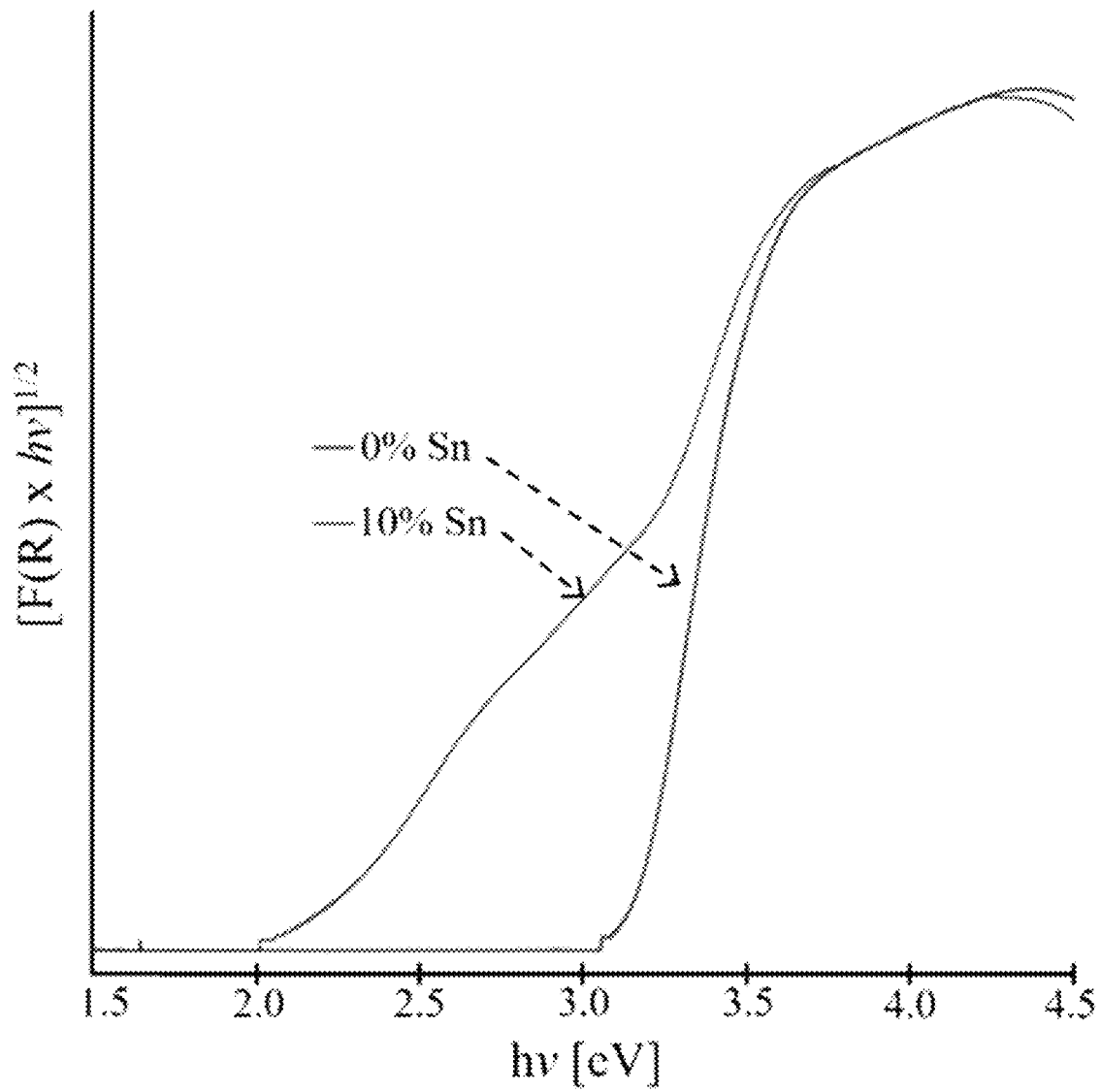
FIG. 42. UV-Vis diffuse reflectance data as a Tauc plots of $(F(R) \times hv)^n$ versus hv (eV) where n=½ for indirect transitions for $Ba_{1-x}Sn_xTiO_3$. The indirect transition was significantly red shifted compared to the parent BZT phase upon substitution of Sn(II).
Figure 43:
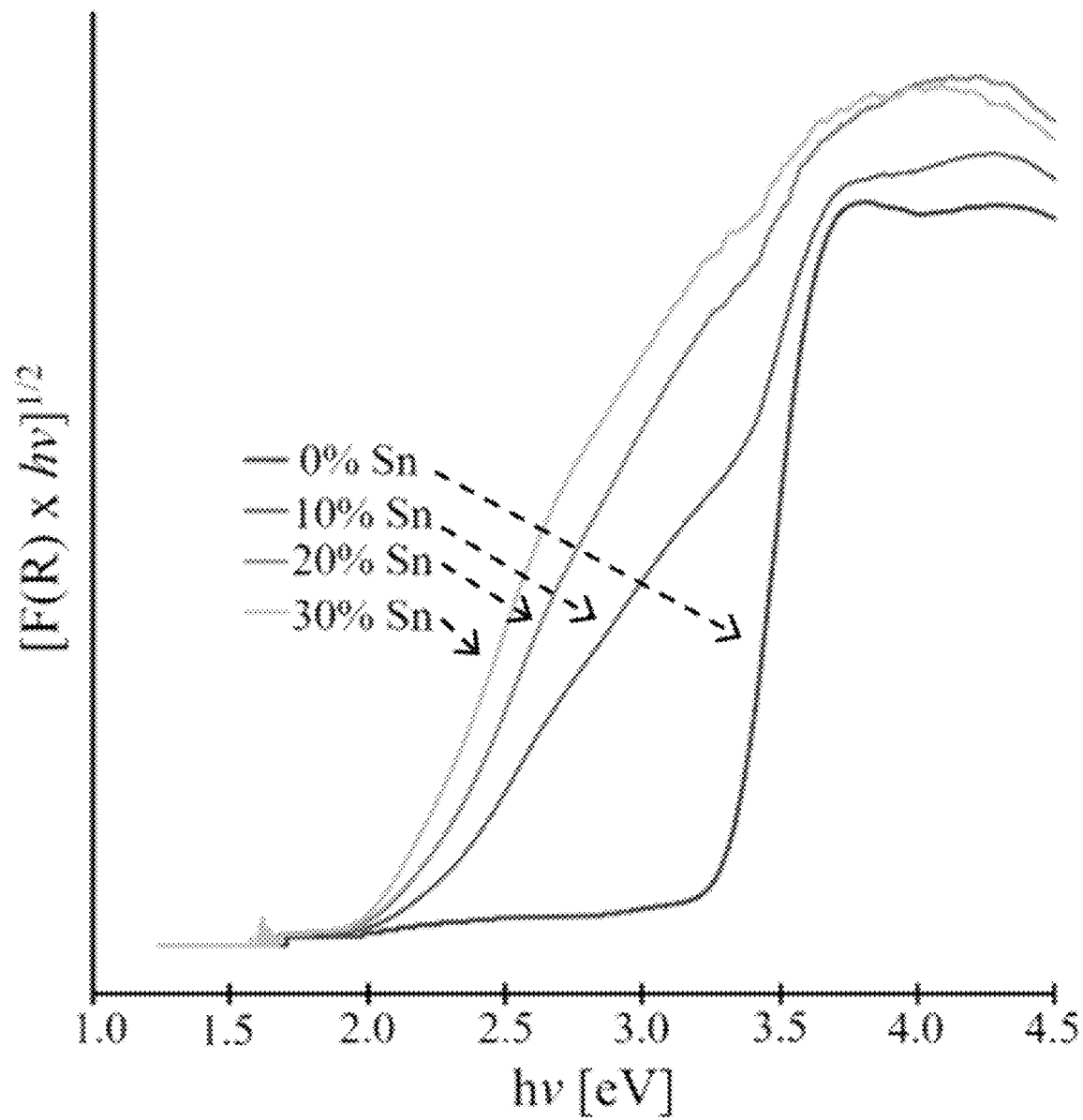
FIG. 43. UV-Vis diffuse reflectance data as a Tauc plots of $(F(R) \times hv)^n$ versus hv (eV) where n=½ for indirect transitions for $Ba_{1-x}Sn_xZr_{0.25}Ti_{0.75}O_3$. The indirect transition was significantly red shifted compared to the parent BZT phase upon substitution of Sn(II).
Figure 44:
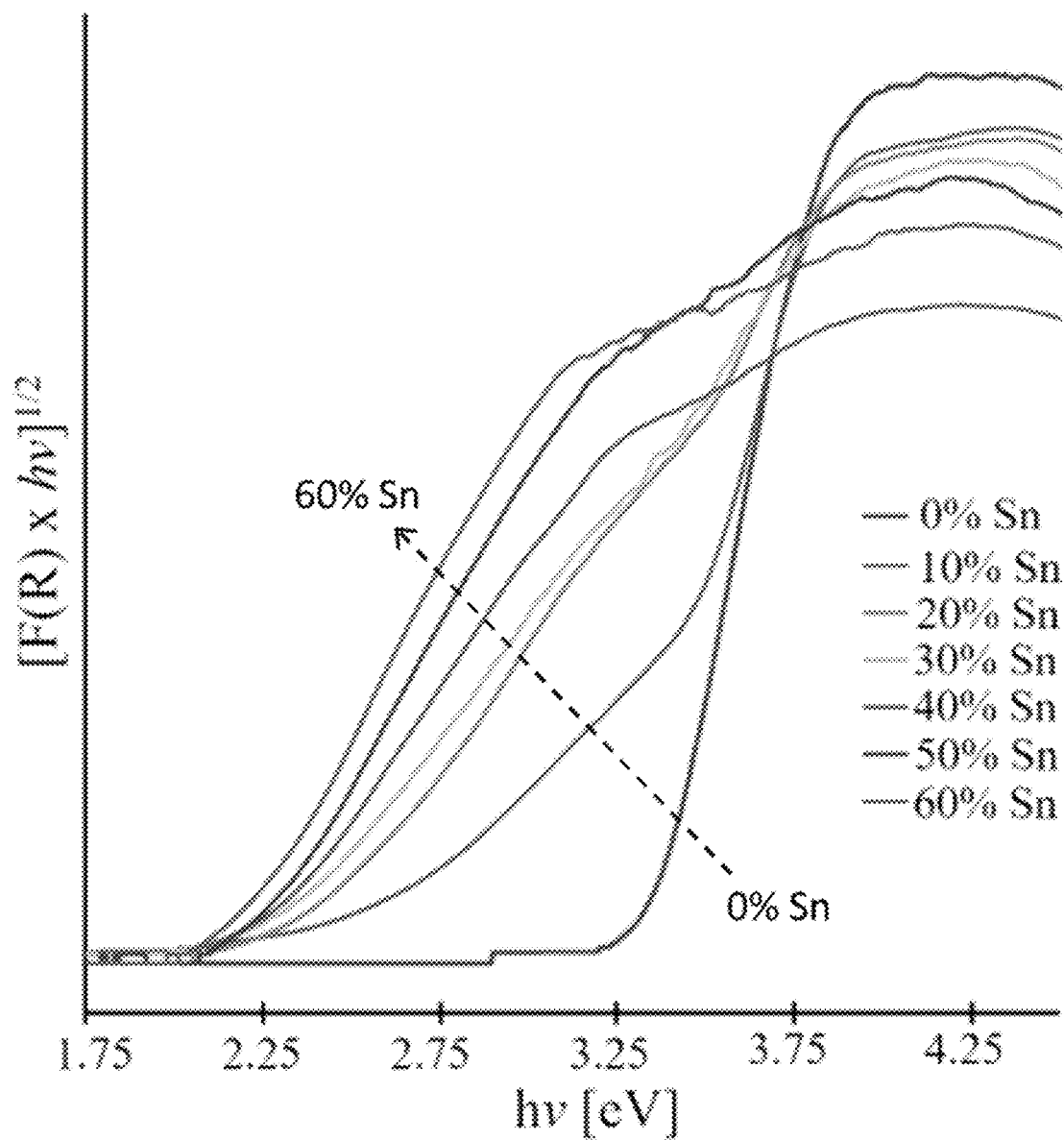
FIG. 44. UV-Vis diffuse reflectance data as a Tauc plots of $(F(R) \times hv)^n$ versus hv (eV) where n=½ for indirect transitions for $Ba_{1-x}Sn_xZr_{0.5}Ti_{0.5}O_3$. The indirect transition was significantly red shifted compared to the parent BZT phase upon substitution of Sn(II).
Figure 45:
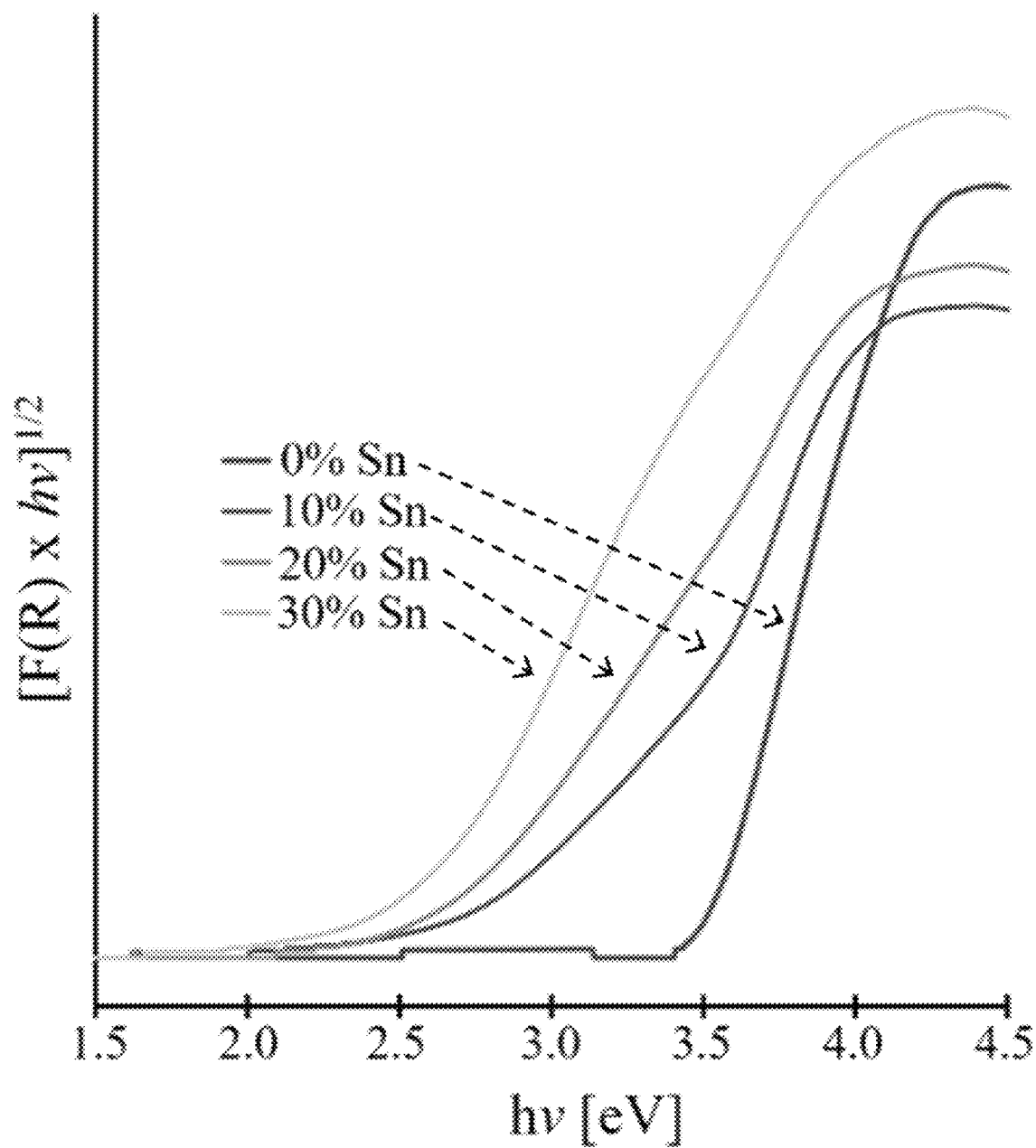
FIG. 45. UV-Vis diffuse reflectance data as a Tauc plots of $(F(R) \times hv)^n$ versus hv (eV) where n=½ for indirect transitions for $Ba_{1-x}Sn_xZr_{0.75}Ti_{0.25}O_3$. The indirect transition was significantly red shifted compared to the parent BZT phase upon substitution of Sn(II).
Figure 46:
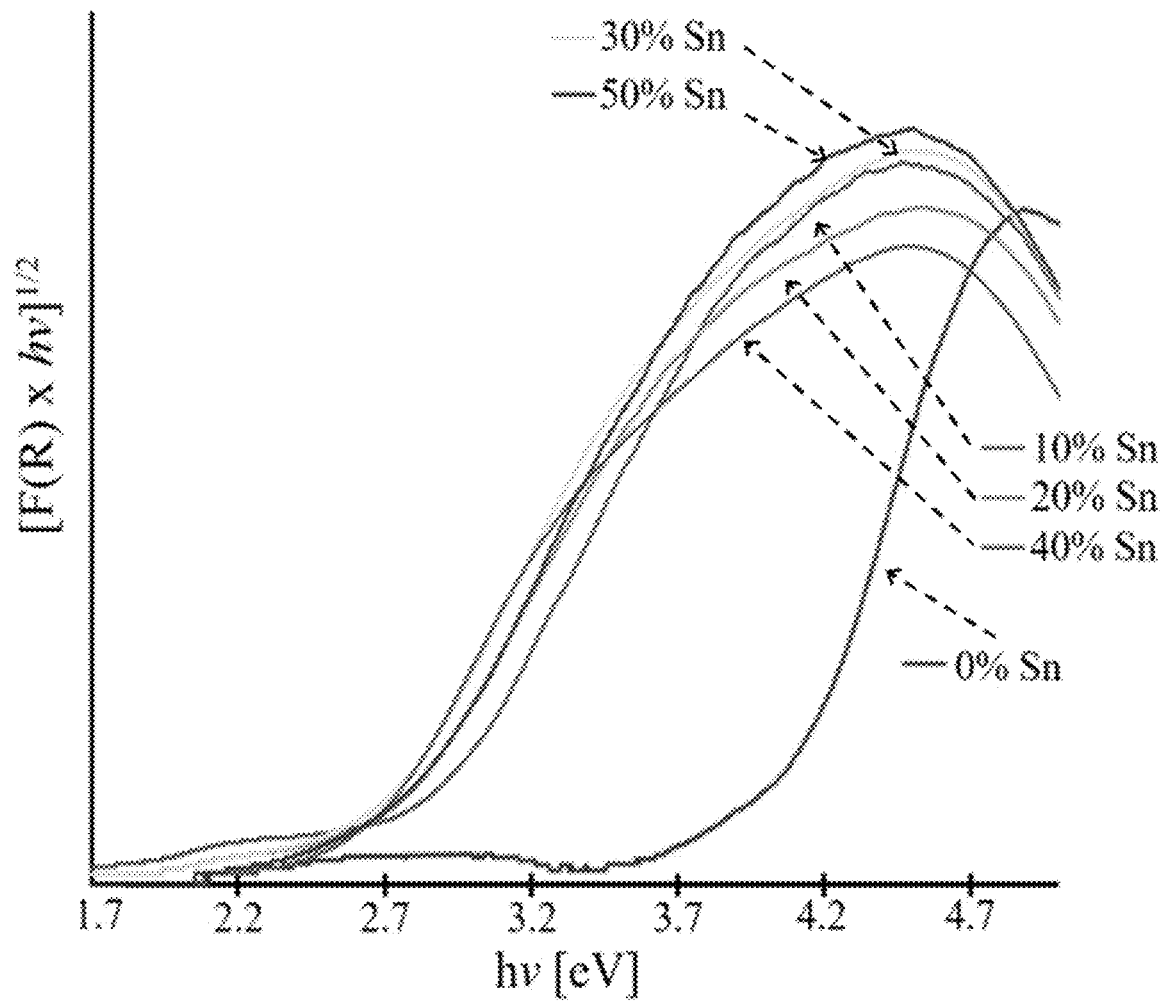
FIG. 46. UV-Vis diffuse reflectance data as a Tauc plots of $(F(R) \times hv)^n$ versus hv (eV) where n=½ for indirect transitions for $Ba_{1-x}Sn_xZrO_3$. The indirect transition was significantly red shifted compared to the parent BZT phase upon substitution of Sn(II).
Figure 47:
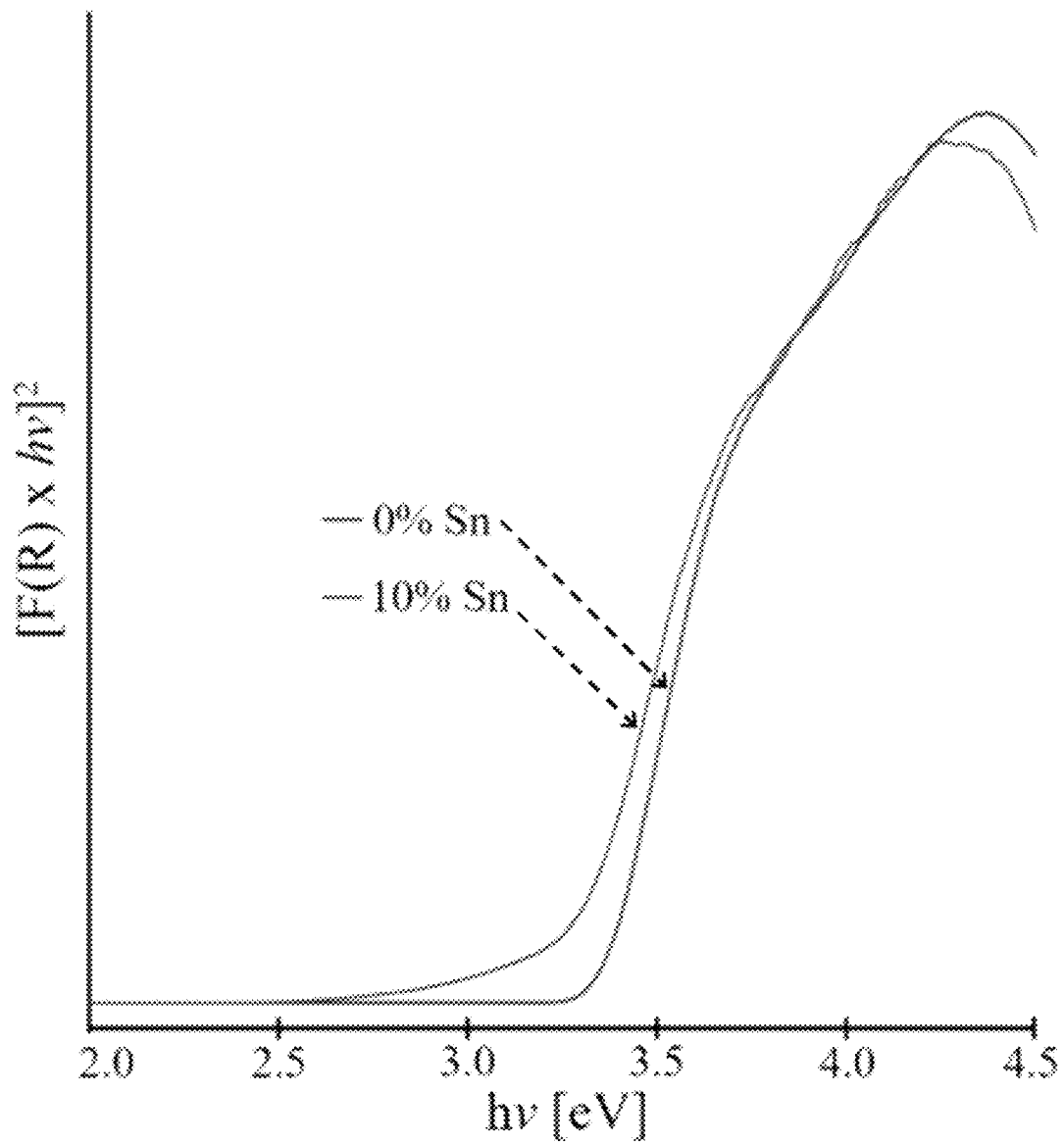
FIG. 47. UV-Vis diffuse reflectance data as a Tauc plots of $(F(R) \times hv)^n$ versus hv (eV) where n=2 for direct transitions for $Ba_{1-x}Sn_xTiO_3$.
Figure 48:
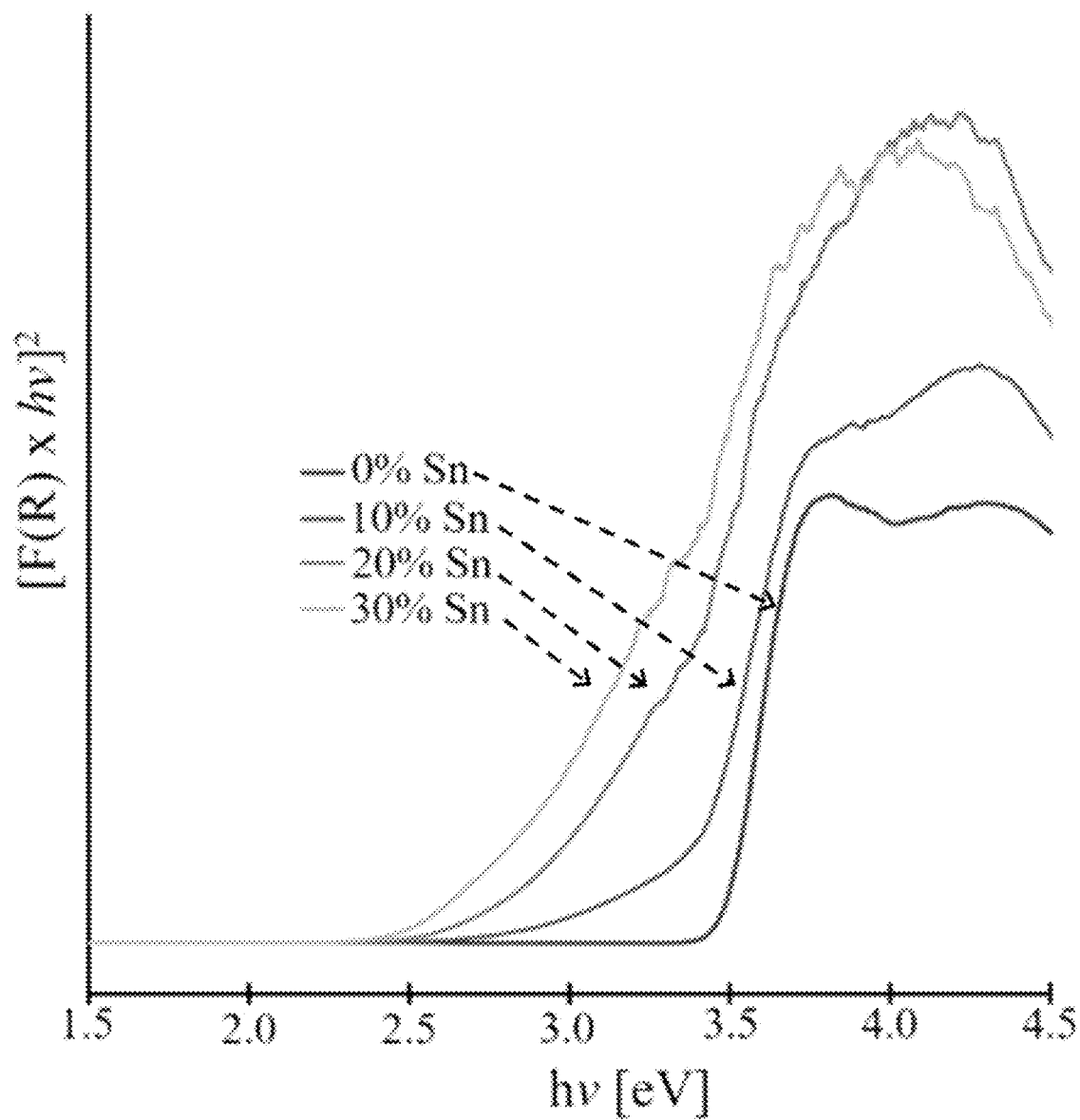
FIG. 48. UV-Vis diffuse reflectance data as a Tauc plots of $(F(R) \times hv)^n$ versus hv (eV) where n=2 for direct transitions for $Ba_{1-x}Sn_xZr_{0.25}Ti_{0.75}O_3$.
Figure 49:
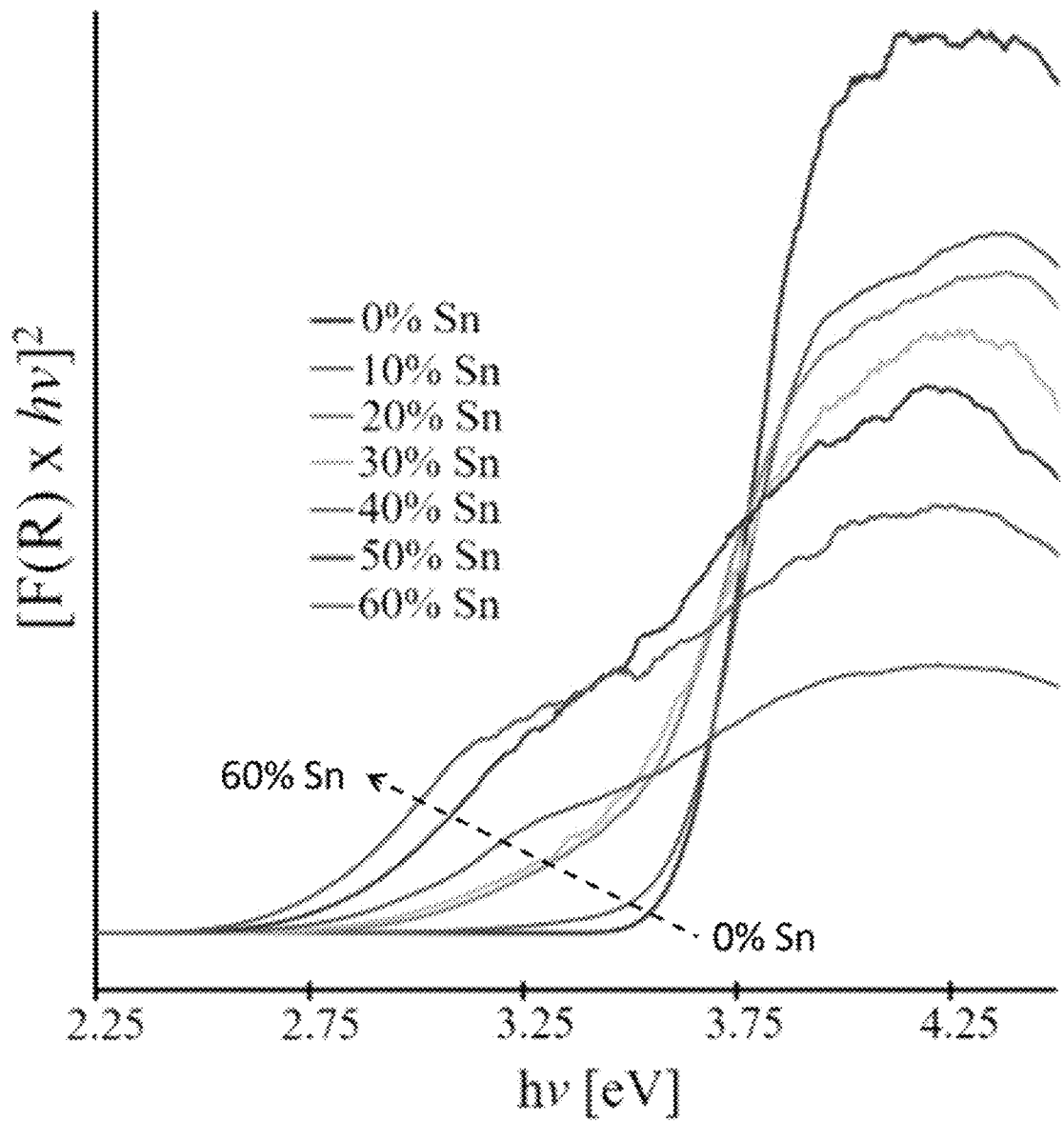
FIG. 49. UV-Vis diffuse reflectance data as a Tauc plots of $(F(R) \times hv)^n$ versus hv (eV) where n=2 for direct transitions for $Ba_{1-x}Sn_xZr_{0.5}Ti_{0.5}O_3$.
Figure 50:
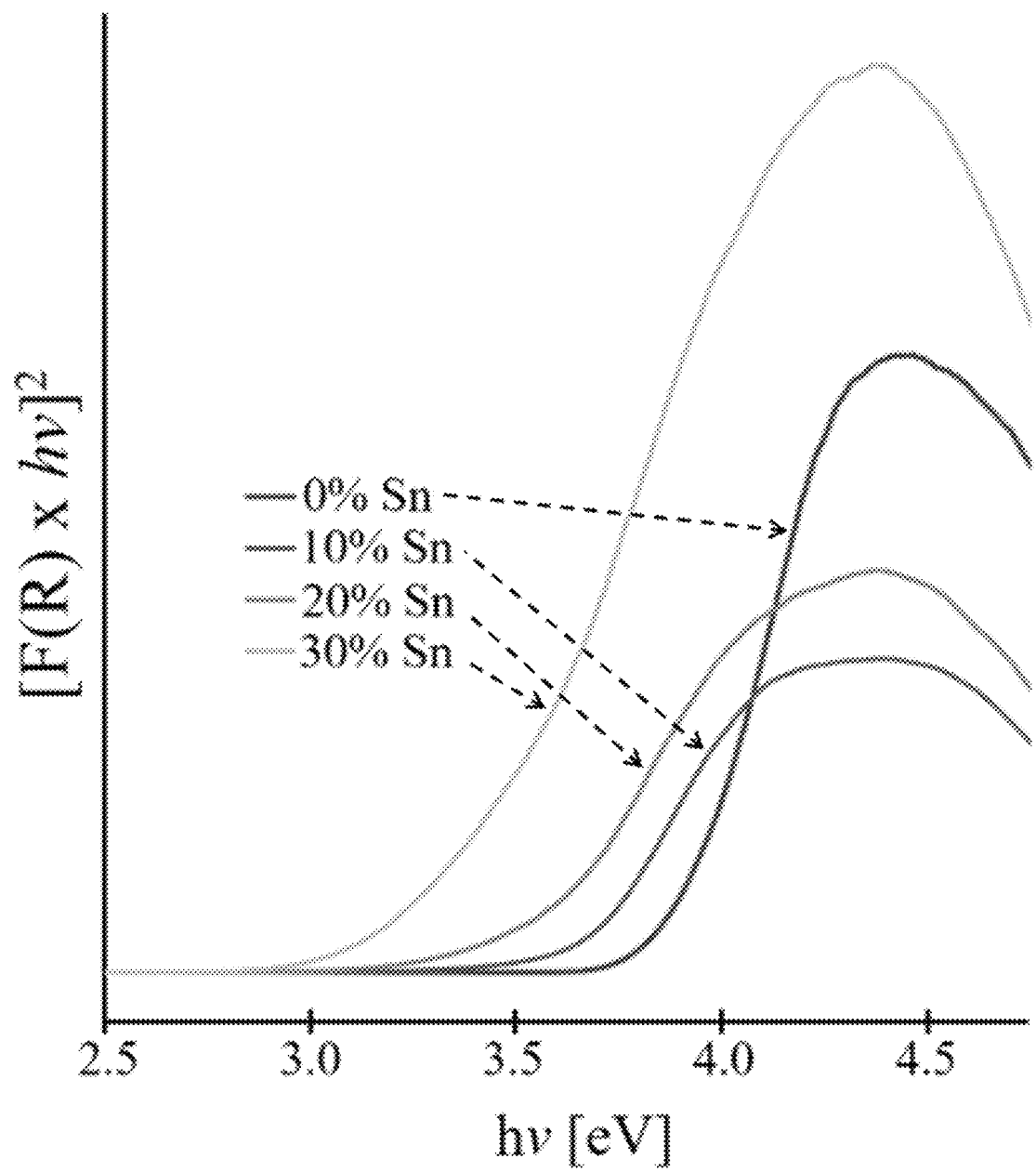
FIG. 50. UV-Vis diffuse reflectance data as a Tauc plots of $(F(R) \times hv)^n$ versus hv (eV) where n=2 for direct transitions for $Ba_{1-x}Sn_xZr_{0.75}Ti_{0.25}O_3$.
Figure 51:
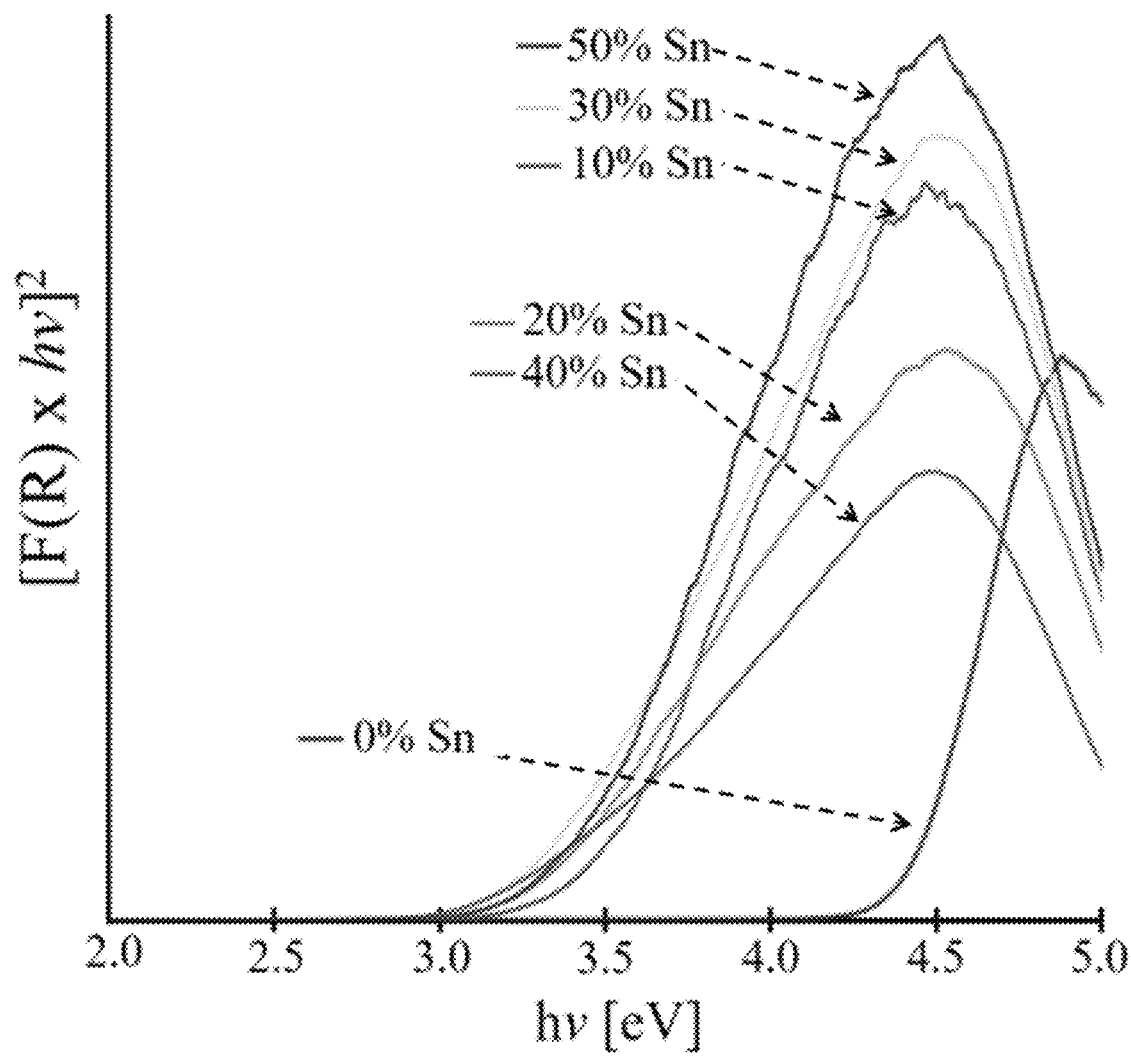
FIG. 51. UV-Vis diffuse reflectance data as a Tauc plots of $(F(R) \times hv)^n$ versus hv (eV) where n=2 for direct transitions for $Ba_{1-x}Sn_xZrO_3$.

The decomposition pathways calculated for the $(Ba_{1-x}Sn_x)(Zr_{1-y}Ti_y)O_3$ (BSZT) perovskites were based upon the experimentally observed products at each composition. For example, both pure Sn(II)-based perovskites are highly thermodynamically unstable with respect to decomposition to the binary oxides, e.g., $SnZrO_3 \rightarrow SnO+ZrO_2$ by a significant ~2.3 eV formula$^{-1}$ (~0.46 eV atom$^{-1}$). By comparison, $BaZrO_3$ is thermodynamically stable with respect to decomposition to the constituent binary oxides. For a mixed Ba(II)/Sn(II) solid solution the decomposition is calculated according to the following reaction: 2 $(Ba_{0.5}Sn_{0.5})ZrO_3 \rightarrow BaZrO_3+SnO+ZrO_2$. The decomposition products are consistent with the experimental product distributions, as shown for example in FIG. 40 and FIG. 41. In a mixed Ba(II)/Sn(II) and Ti(IV)/Zr(IV) solid solution of BSZT, the decomposition reaction proceeds by the formation of a mixture of SnO and $ZrO_2/TiO_2$.

Figure 17:
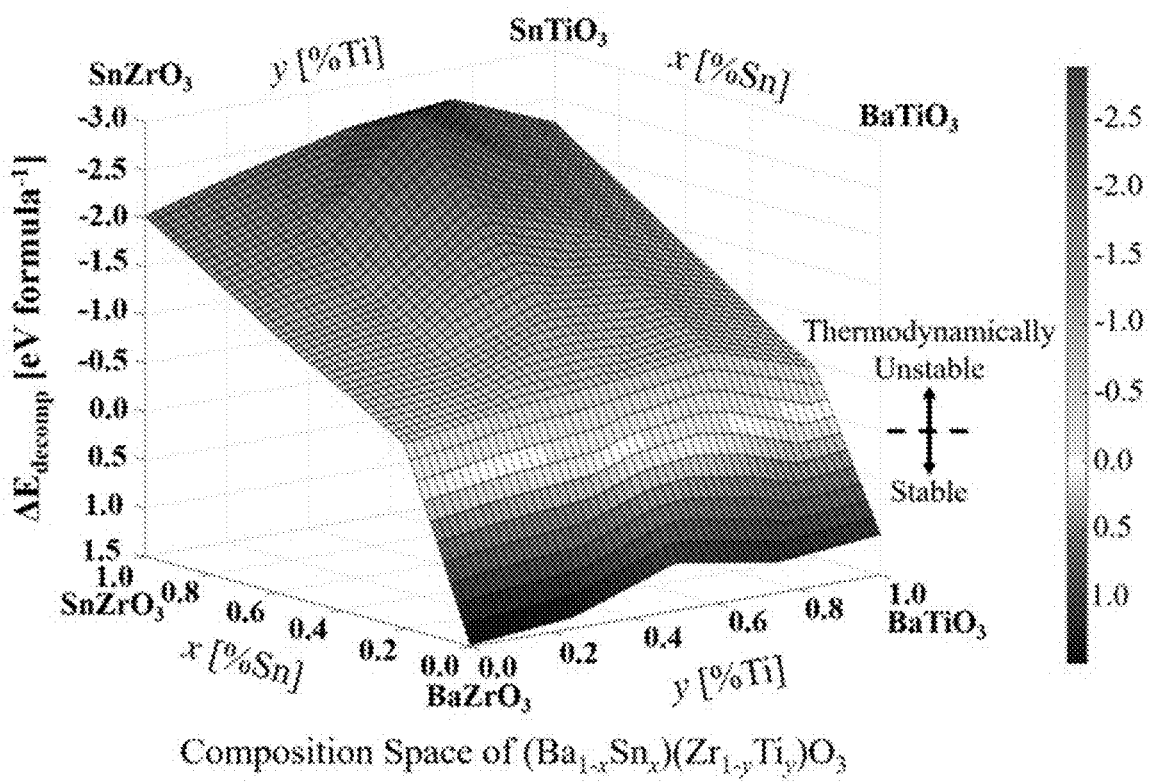
FIG. 17: Calculated reaction energy landscape for perovskite decomposition at 0 K in the composition space spanning $BaTiO_3$—$BaZrO_3$—$SnTiO_3$—$SnZrO_3$, as representing the mixed A/A'- and B/B'-site solid solution $Ba_{1-x}Sn_xZr_{1-y}Ti_yO_3$. The orange to red colors denote increasing instability and the light blue to dark blue colors indicate increasing stability.

The decomposition energies of the reactions were calculated and plotted in FIG. 17 as a function of the A/A'-site (Ba/Sn; x-axis) and B/B'-site (Zr/Ti; y-axis) compositions in the $BaTiO_3$—$BaZrO_3$—$SnTiO_3$—$SnZrO_3$ system. All 100% Sn(II)-based perovskites are thermodynamically unstable, e.g., $SnTiO_3$ is thermodynamically unstable with respect to decomposition to SnO and $TiO_2$ by a significant ~2.0 eV formula$^{-1}$ (~0.40 eV atom$^{-1}$). Starting from the thermodynamically stable $BaTiO_3$, an increasing substitution of Sn(II) into the structure can be modeled as the solid solution $(Ba_{1-x}Sn_x)TiO_3$ with increasing x, shown in FIG. 17 (upper right x-axis). The solid solution rapidly becomes unstable with respect to decomposition beyond x ~0.15, or ~15% Sn(II) cations, in agreement with prior synthetic studies using high temperature conditions that have found ~10% or less of Sn(II) can be incorporated into titanate perovskites. Similar results are found for the zirconate analogue, i.e., $(Ba_{1-x}Sn_x)ZrO_3$ in FIG. 17 (x-axis; lower left), which is predicted to be metastable beyond ~15% Sn(II) cations. Consistent results are found for Sn(II)-substitution across the entire mixed-Ti/Zr composition range of the $(Ba_{1-x}Sn_x)(Zr_{1-y}Ti_y)O_3$ solid solution. At all compositions, a higher Sn(II) content leads to a rapid decrease in stability with a nearly linear negative slope in the perovskite formation energy of ~0.5 eV formula$^{-1}$.

An enhanced synthesizability of metastable perovskites containing Sn(II) cations is found with an increasing Zr substitution on the B-site, although these compositions are more highly metastable. With 0% Zr, i.e., $BaTiO_3$, only ~10% Sn(II) could be substituted before the product converted to the more stable ilmenite structure type. However, up to 50% to 60% Sn(II) substitution could be achieved in the perovskite structure when Zr(IV) cations were substituted for Ti(IV) cations on the B-site, leading to the metastable $(Ba_{0.5}Sn_{0.5})ZrO_3$ or $(Ba_{0.4}Sn_{0.6})(Ti_{0.5}Zr_{0.5})O_3$. These compositions occur in the areas of high metastability, FIG. 17, and are highly unstable with respect to decomposition to the binary oxides by ~0.27 eV atom$^{-1}$ and ~0.25 eV atom$^{-1}$, respectively. By comparison, it has typically been considered that an excess free energy above some empirically-defined limit, e.g., ranging from −0.05 to 0.15 eV atom$^{-1}$, will render a metastable phase not synthesizable (Sun et al. *Sci. Adv.* 2016, 2 (11), e160025; Aykol et al. *Sci. Adv.* 2018, 4, eaaq0148). The Sn(II)-substitution obtained by the low-temperature flux reactions greatly exceeds the thermodynamic limits of stability with a metastability that has not been found using high temperature synthetic methods.

Possible explanations for the successful synthesis of the highly metastable BSZT compositions are the configurational entropy and/or the kinetic stabilization provided by the high cohesive energy of the underlying perovskite network. As has been shown for entropy-stabilized oxides and alloys, enhanced phase stability can result when a large number of different elements are mixed and disordered over the same crystallographic sites (Yeh et al. *Adv. Eng. Mater.* 2004, 6 (5), 299-303; Rost et al. *Nat. Commun.* 2015, 6, 8485). For BSZT, which has two sites mixed with two metal cations, the calculated $S_{max}$ is only on the order of ~5.0×10$^{-5}$ eV K$^{-1}$, or ~0.015 eV at room temperature. This is significantly smaller than the calculated decomposition energies, showing this is too small to be responsible for the stabilization of BSZT. Furthermore, entropy stabilized solids become more stable with increasing temperature rather than decompose as observed for BSZT. While the $(Ba_{0.7}Sn_{0.3})(Zr_{0.5}Ti_{0.5})O_3$ composition can be successfully synthesized, exchange reactions performed at higher temperatures for longer time clearly results in decomposition, FIG. 40. Additionally, heating of the BSZT compositions with >10% Sn(II) cations at higher temperatures leads to decomposition, FIG. 41.

Large-scale studies have shown that metastable phases are more frequently found, i.e., synthesizable, when they have higher cohesive energies (Sun et al. *Sci. Adv.* 2016, 2 (11), e160025; Aykol et al. *Sci. Adv.* 2018, 4, eaaq0148). These findings indicate that stronger bonds can be more capable of 'locking in' energetically unfavorable atomic arrangements. Furthermore, the likelihood of a ground state of a metastable phase being phase separated rather than polymorphic increases with the number of elements, with inhibition of the atomic diffusion and segregation providing a kinetic barrier for decomposition to more thermodynamically favored products (Sun et al. *Sci. Adv.* 2016, 2 (11), e160025). Perovskite oxides have been found to exhibit relatively high cohesive energies, especially for zirconates (Goudochnikov et al. *J. Phys.: Condens. Matter* 2007, 19, 176201), and can therefore kinetically stabilize against decomposition by inhibiting significant cation and anion diffusion. The above factors help to understand the high amount of Sn(II) that can be substituted under these reaction conditions into different compositions of the $Ba(Zr_{1-y}Ti_y)O_3$ perovskite. The synthesis of metastable $(Ba_{1-x}Sn_x)(Zr_{1-y}Ti_y)O_3$ (BSZT), with a positive free energy of formation, is driven by the larger negative free energy of formation of BaClF in the reaction. The low reaction temperature, short reaction time, and high cohesive energy of the BZT phases inhibit long-range ion diffusion. When comparing $BaTiO_3$ and $BaZrO_3$, the former readily converts to the ilmenite-structure type with the substitution of >10% Sn(II) cations of the same composition without the need for significant ion diffusion. By contrast, the ilmenite structure is not stable for the zirconate perovskite and must therefore decompose by significant cation diffusion and segregation into simpler binary oxides. As compared to $BaTiO_3$, the $BaZrO_3$ perovskite also has a higher cohesive energy (−41.43 eV versus −39.69 eV) and a significantly higher melting point (2,700° C. versus 1,625° C.). As a result, $BaZrO_3$ can incorporate a much higher amount of ~50-60% Sn(II) cations with a high metastability before the onset of decomposition.

A high metastability is also achieved for the mixed B-site solid solution of 50% Zr(IV) and 50% Ti(IV) cations, i.e., starting from the $Ba(Zr_{0.5}Ti_{0.5})O_3$ perovskite. In this perovskite up to ~60% Sn(II) can be attained, i.e., $(Ba_{0.4}Sn_{0.6})(Zr_{0.5}Ti_{0.5})O_3$. Its decomposition is inhibited as significant ion diffusion is required for decomposition to occur to give the binary oxides $ZrO_2$ and SnO. The $Ba(Zr_{0.5}Ti_{0.5})O_3$ solid solution is the composition where both the Zr(IV) and Ti(IV) are the most diluted in the perovskite lattice, and consequently, the greatest ion diffusion is required for decomposition. For example, the synthesis of $MS_2$ (M=Fe, Co, Ni)

has similarly shown that crystalline metastable intermediates are observed during the reaction of $Na_2S_2$ with $MCl_2$ that are trapped owing to the limited ion diffusion achieved under low temperature solid-state reaction conditions in a similar fashion to BSZT (Martinolich et al. *J. Am. Chem. Soc.* 2016, 138 (34), 11031-11037). This suggests that an effective approach for the synthesis of metastable phases is the dilution of multiple different cations over equivalent crystallographic sites, requiring maximal ion diffusion for their decomposition.

Figure 18:
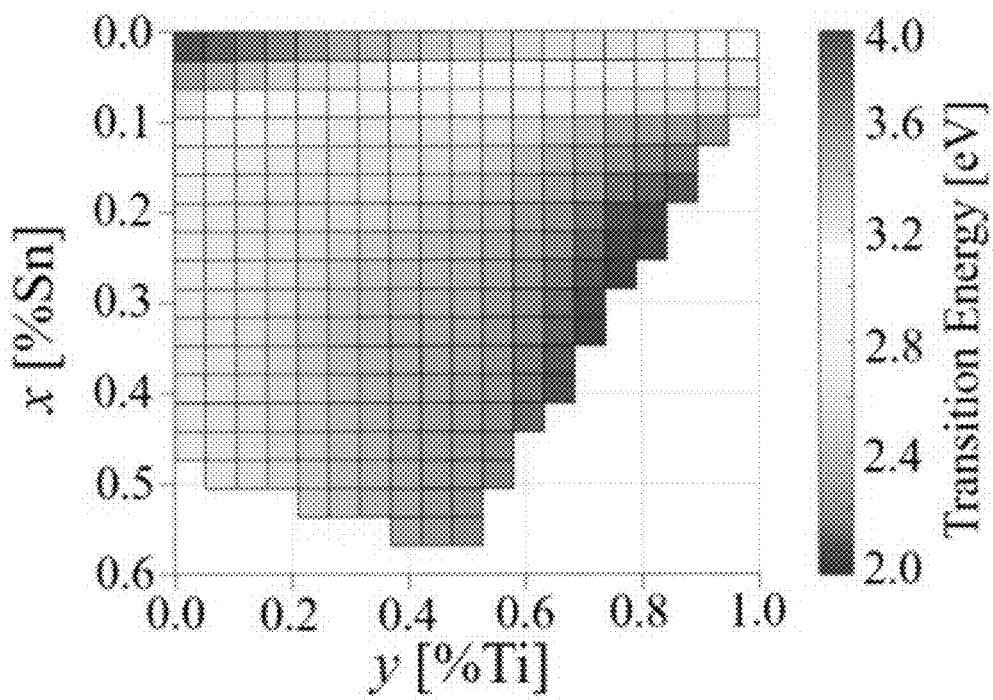
FIG. 18: Experimentally observed indirect bandgap size of $(Ba_{1-x}Sn_x)(Zr_{1-y}Ti_y)O_3$ as a function of the Ba/Sn A-site (x-axis) and Zr/Ti B-site (y-axis) compositions. The blue to yellow to red colors indicate the decreasing bandgap sizes.
Figure 19:
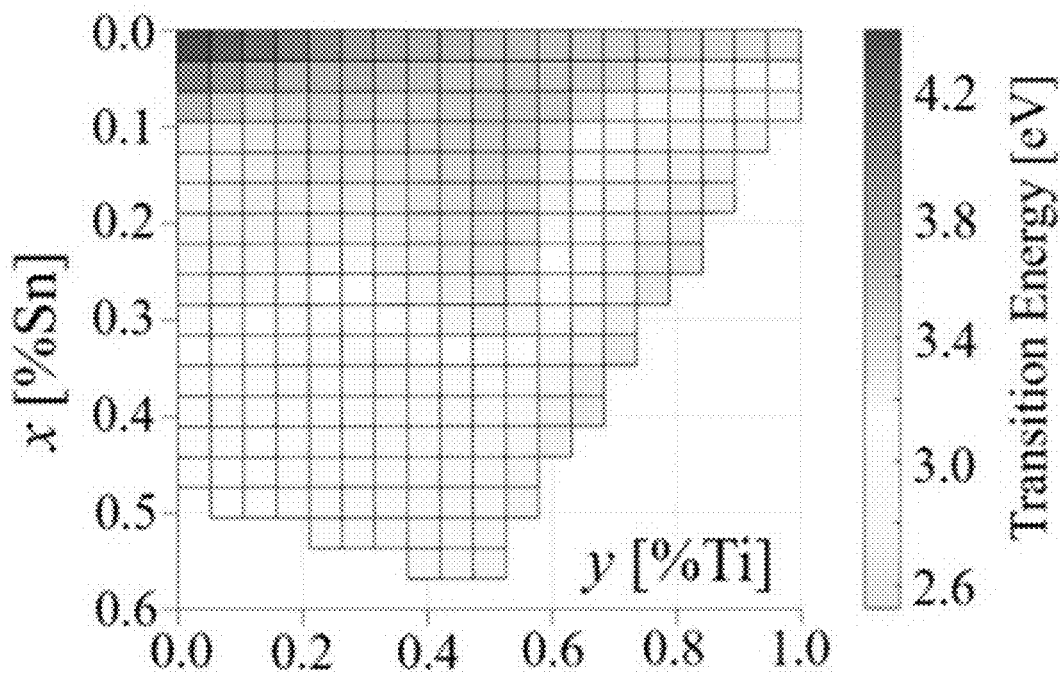
FIG. 19: Experimentally observed direct bandgap transition of $(Ba_{1-x}Sn_x)(Zr_{1-y}Ti_y)O_3$ as a function of the Ba/Sn A-site (x-axis) and Zr/Ti B-site (y-axis) compositions. The blue to yellow to red colors indicate the decreasing bandgap sizes.
Figure 20:
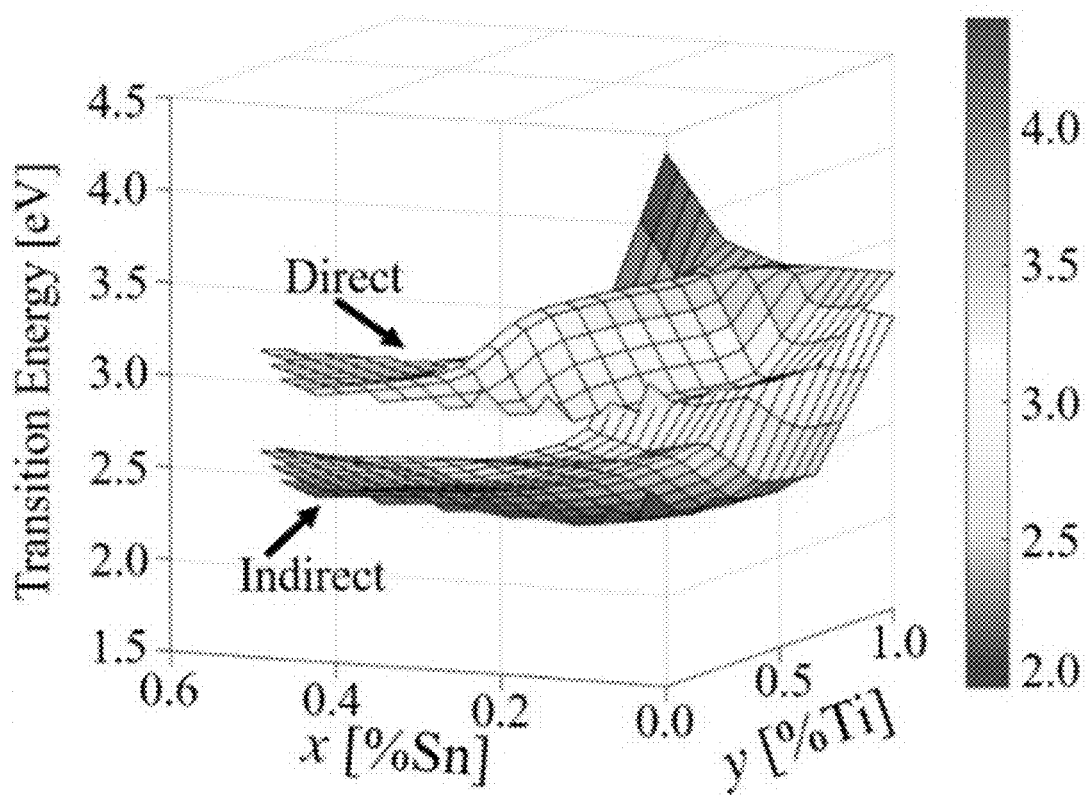
FIG. 20: Both the indirect bandgap (FIG. 18) and direct bandgap (FIG. 19) transitions of $(Ba_{1-x}Sn_x)(Zr_{1-y}Ti_y)O_3$ are plotted together as a function of the Ba/Sn A-site (x-axis) and Zr/Ti B-site (y-axis) compositions. The blue to yellow to red colors indicate the decreasing bandgap sizes.

Optical Properties and Electronic Structure. Metal oxides containing the Sn(II) cation are under intense investigation as small bandgap semiconductors. Optical absorption measurements were taken to probe how the increasing Sn(II) substitution impacts the band gap. The direct and indirect bandgap energies are plotted together in FIG. 18-FIG. 20 as a function of the mixed A/A'-site (Ba/Sn; x-axis) and B/B'-site (Zr/Ti; y-axis) stoichiometries. All compositions show a lowest energy indirect bandgap transition spanning a wide range from ~3.90 eV for $BaZrO_3$ to ~1.95 eV for $(Ba_{0.7}Sn_{0.3})(Zr_{0.25}Ti_{0.75})O_3$, with direct band gaps for each composition that is ~0.2 eV to 0.8 eV higher in energy. The band gap is generally found to decrease with increasing Sn(II) and Ti(IV) compositions, as labeled by the red areas in FIG. 18. As the Sn(II) concentration increases, an absorption edge at lower energy forms and grows as a result of the increasing density of the Sn(II) states in the valence band. These results are consistent with prior research on solid solutions with tunable chemical compositions (Palasyuk et al. *Inorg. Chem.* 2010, 49 (22), 10571-10578; Boltersdorf et al. *J. Phys. Chem. C* 2016, 120 (34), 19175-19188). Compositions with the highest amounts of Sn(II) cations exhibit the smallest band gaps, e.g., 1.95 eV for $(Ba_{0.7}Sn_{0.3})(Zr_{0.25}Ti_{0.75})O_3$, 2.14 eV for $(Ba_{0.4}Sn_{0.6})(Zr_{0.5}Ti_{0.5})O_3$, and 2.40 eV for $(Ba_{0.7}Sn_{0.3})(Zr_{0.75}Ti_{0.25})O_3$. The regions of the BSZT composition space with the smallest bandgap sizes also correspond to the areas of highest metastability in FIG. 17. The $ZrO_2$ impurity found in some samples exhibits a band gap of >5.0 eV, significantly higher in energy than found for the BSZT phases. These results show an underlying relationship between high metastability and the formation of the smallest band gaps.

The dependence of the bandgap size on the BSZT composition can be fitted to the standard bowing equation (Wu et al. *Solid St. Commun.* 2003, 127, 411-414):

$$E_g^{BSZT}(x) = E_g^1 \cdot x + E_g^2 (1-x) - bx(1-x)$$

wherein $E_g^1$ and $E_g^2$ are the band gaps of the endpoint compositions, x is the mole fraction of each, and b is the bowing parameter. Starting from –10% Sn(II) in each BSZT composition, an increasing Sn(II) substitution could be well-fitted to a bowing parameter of 0.45 eV. The largest change in the indirect band gap occurred with the increase from 0% to 10% Sn(II) cations, decreasing the band gap by a consistent ~0.75 to 0.9 eV for all compositions. For example, the 3.30 eV bandgap size of $Ba(Zr_{0.5}Ti_{0.5})O_3$ was decreased to 2.54 eV with the introduction of only 10% Sn(II) cations. The bowing parameter value, fitted from 10% to 60% Sn(II) cations, represents the extent of band widening and dispersion that occurs with increasing amounts of —O—Sn—O—Sn—O connectivity within the structure. The band dispersion also has a significant impact on the energetic separation between the indirect and direct bandgap transitions that increases with the Sn(II) and Ti(IV) cations, shown in FIG. 20 and FIG. 42-FIG. 51, with the valence band widening having a predominant effect on the indirect transition.

Figure 52:
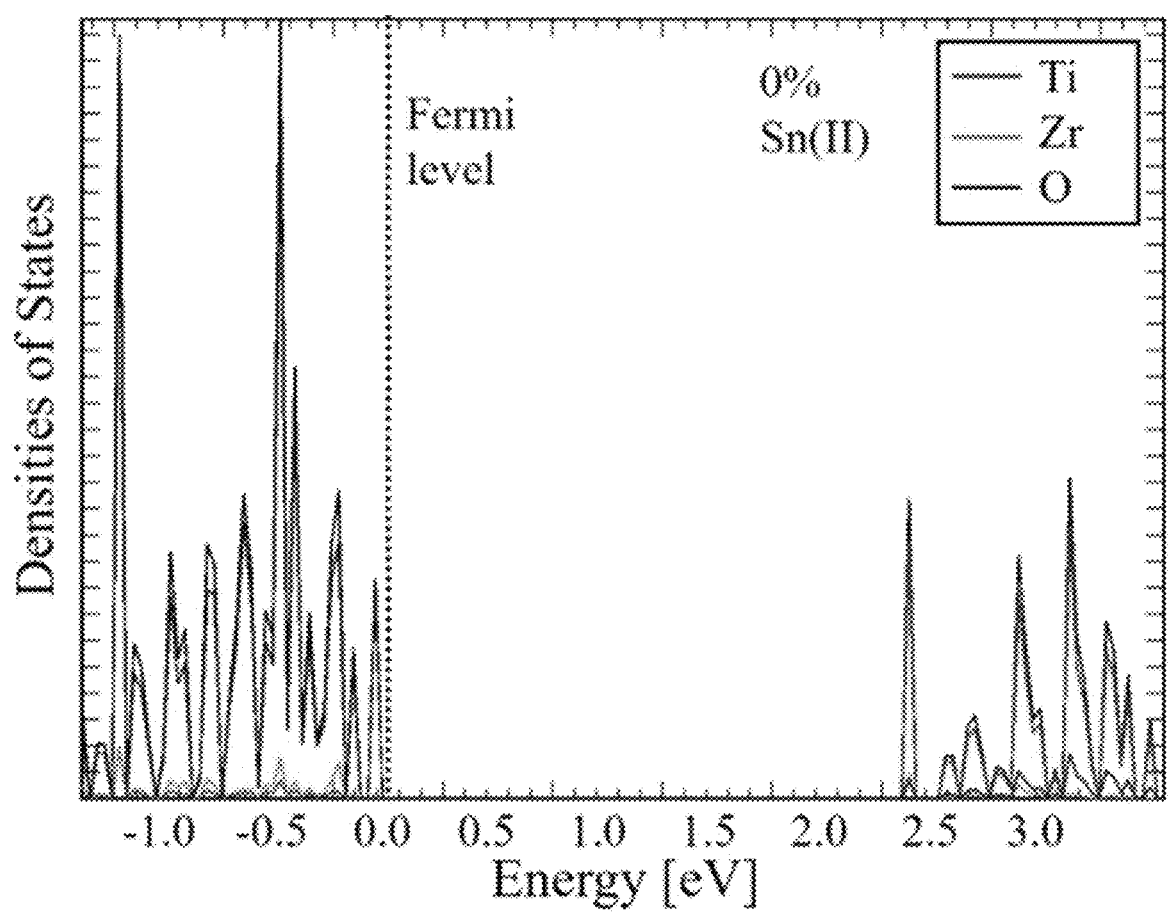
FIG. 52. Densities-of-States (DOS) plot for $Ba(Zr_{0.5}Ti_{0.5})O_3$. The contributions of the individual atomic orbitals are represented by colored lines and the total DOS by the black line. In each, the Fermi level is located at 0 eV.
Figure 53:
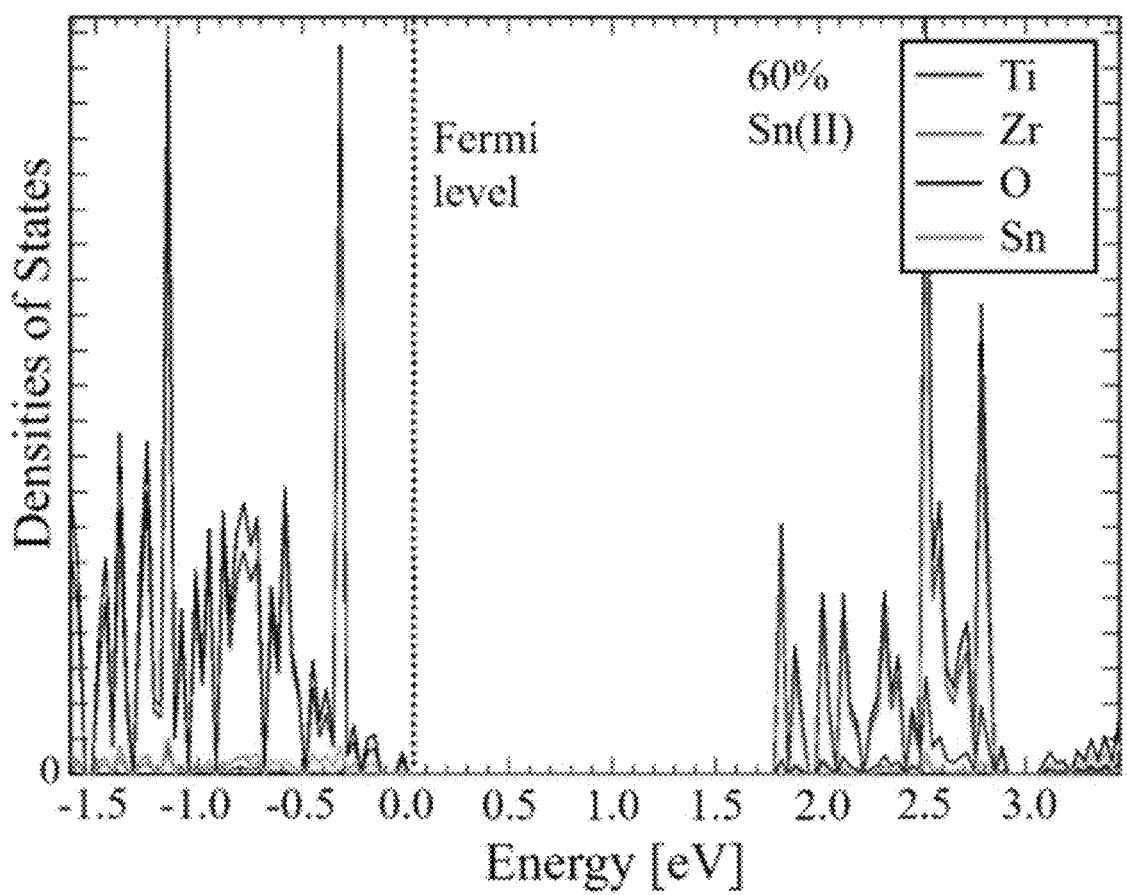
FIG. 53. Densities-of-States (DOS) plot for $(Ba_{0.4}Sn_{0.6})(Zr_{0.5}Ti_{0.5})O_3$. The contributions of the individual atomic orbitals are represented by colored lines and the total DOS by the black line. In each, the Fermi level is located at 0 eV.

Electronic structure calculations were performed in order to probe the origins of the changes in the bandgap size with increasing Sn(II) substitution, given in FIG. 52-FIG. 53. For $Ba(Zr_{0.5}Ti_{0.5})O_3$, the band gap is primarily set by the energetic distance between the Ti 3d- and O 2p-based states, with the Zr 4d orbitals located at higher energies. After substitution of 60% Sn(II) cations, the valence band is now composed of strongly interacting Sn 5 s and O 2p states, with a shift of the valence band edge to higher energies. These results are consistent with prior electronic structure investigations of Sn(II)-containing oxides, wherein the Sn 5 s orbitals interact with the O 2p orbitals at the valence band edge and result in a smaller band gap (Noureldine et al. *Catal. Sci. Technol.* 2016, 6 (21), 7656-7670; O'Donnell et al. *J. Electrochem. Soc.* 2019, 166 (5), H3084-H3090). As the concentration of Sn(II) increases, the Sn 5 s contributions in the valence band increases. This is a result of the extended —O—Sn—O—Sn—O-network that is formed with greater Sn(II) substitution, and which increases the Sn—O antibonding interactions.

Suspended Particle Photocatalysis. Prior experimental and computational studies have predicted that Sn(II)-containing oxides frequently have favorable band energetics for efficient photocatalysis under sunlight (Noureldine et al. *Catal. Sci. Technol.* 2016, 6 (21), 7656-7670; O'Donnell et al. *J. Electrochem. Soc.* 2019, 166 (5), H3084-H3090; Boltersdorf et al. *Chem. Mater.* 2017, 28, 8876-8889; Emery et al. *Scient. Data* 2017, 4, 170153; Saal et al. JOM 2013, 65, 1501-1509; Nishiro et al. *Chem Commun.* 2017, 53, 629-632). For example, previous photocatalytic measurements on $Sn_2TiO_4$, with a band gap of only ~1.55 eV, showed high activity for molecular oxygen evolution with an apparent quantum yield of ~1.0% under 420 nm irradiation (O'Donnell et al. *J. Electrochem. Soc.* 2019, 166 (5), H3084-H3090; Boltersdorf et al. *Chem. Mater.* 2017, 28, 8876-8889). Extended —O—Sn—O—Sn—O connectivity can result in highly disperse valence bands, yielding low carrier effective masses and high carrier mobilities (Ha et al. *J. Mater. Chem. C* 2017, 5 (23), 5772-5779).

Photocatalytic activities across the full range of synthesizable $(Ba_{1-x}Sn_x)(Zr_{1-y}Ti_y)O_3$ (BSZT) powders were measured for molecular oxygen evolution. These rates are plotted collectively in FIG. 21-FIG. 23 as a function of the mixed A-site Ba/Sn (x) and B-site Zr/Ti (y) compositions. Photocatalytic rates were taken under combined ultraviolet and visible (UV+Vis) light ($\lambda$>230 nm) or under only visible-light ($\lambda$>400 nm) irradiation, FIG. 21 and FIG. 22, respectively, and Table 4. Bandgap transitions of the BZT phases, i.e., $Ba(Zr_{1-y}Ti_y)O_3$, all occur in the ultraviolet energies of >3.2 eV. Accordingly, these perovskites all showed little to no activity under visible-light irradiation, but relatively high activity under UV+Vis light of ~170 to 210 $\mu$mol $O_2$ $h^{-1}g^{-1}$. In contrast, the substitution of >10% Sn(II) cations in the BSZT phases, i.e., $(Ba_{1-x}Sn_x)(Zr_{1-y}Ti_y)O_3$, resulted in visible-light band gaps and significantly higher activities under both ultraviolet and visible-light irradiation. The higher rates are attributable in part to the absorption of a larger fraction of visible-light wavelengths. Under combined ultraviolet-visible or visible-only irradiation, the highest measured photocatalytic activities peaked at around the $(Ba_{0.6}Sn_{0.4})(Zr_{0.5}Ti_{0.5})O_3$ composition with rates of ~408 $\mu$mol $O_2$ $h^{-1}g^{-1}$ and ~216 $\mu$mol $O_2$ $h^{-1}g^{-1}$, respectively. Conservative estimates of the apparent quantum yields (AQY) give lower limits of ~0.51% (230 nm<$\lambda$<564 nm) and ~0.39% (400 nm<$\lambda$<564 nm) for this composition. The bubbles of molecular oxygen that evolved very rapidly adhered strongly to the particles' surfaces, significantly slowing the apparent reaction rates that were measured volumetrically. This was a result of the particles becoming increasingly hydrophobic with increasing Sn(II) substitution.

TABLE 4

Photocatalytic Rates of BSZT Compounds for Molecular Oxygen Evolution Under UV + Vis and Visible-Light Irradiation.

| Composition | UV + Vis [μmol $O_2$ $h^{-1}g^{-1}$] | Vis [μmol $O_2$ $h^{-1}g^{-1}$] | % Visible |
|---|---|---|---|
| $BaZr_{0.25}Ti_{0.75}O_3$ | 211 | 50 | 24 |
| $Ba_{0.9}Sn_{0.1}Zr_{0.25}Ti_{0.75}O_3$ | 232 | 166 | 72 |
| $Ba_{0.8}Sn_{0.2}Zr_{0.25}Ti_{0.75}O_3$ | 28 | 188 | 66 |
| $Ba_{0.7}Sn_{0.3}Zr_{0.25}Ti_{0.75}O_3$ | 197 | 188 | 95 |
| $BaZr_{0.5}Ti_{0.5}O_3$ | 173 | 95 | 55 |
| $Ba_{0.9}Sn_{0.1}Zr_{0.5}Ti_{0.5}O_3$ | 311 | 106 | 34 |
| $Ba_{0.8}Sn_{0.2}Zr_{0.5}Ti_{0.5}O_3$ | 293 | 205 | 70 |
| $Ba_{0.7}Sn_{0.3}Zr_{0.5}Ti_{0.5}O_3$ | 311 | 184 | 59 |
| $Ba_{0.6}Sn_{0.4}Zr_{0.5}Ti_{0.5}O_3$ | 408 | 216 | 53 |
| $Ba_{0.5}Sn_{0.5}Zr_{0.5}Ti_{0.5}O_3$ | 314 | 188 | 60 |
| $Ba_{0.4}Sn_{0.6}Zr_{0.5}Ti_{0.5}O_3$ | 265 | 183 | 69 |
| $BaZr_{0.75}Ti_{0.25}O_3$ | 200 | 40 | 20 |
| $Ba_{0.9}Sn_{0.1}Zr_{0.75}Ti_{0.25}O_3$ | 152 | 180 | 120 |
| $Ba_{0.8}Sn_{0.2}Zr_{0.75}Ti_{0.25}O_3$ | 167 | 148 | 89 |
| $Ba_{0.7}Sn_{0.3}Zr_{0.75}Ti_{0.25}O_3$ | 136 | 165 | 121 |

Figure 21:
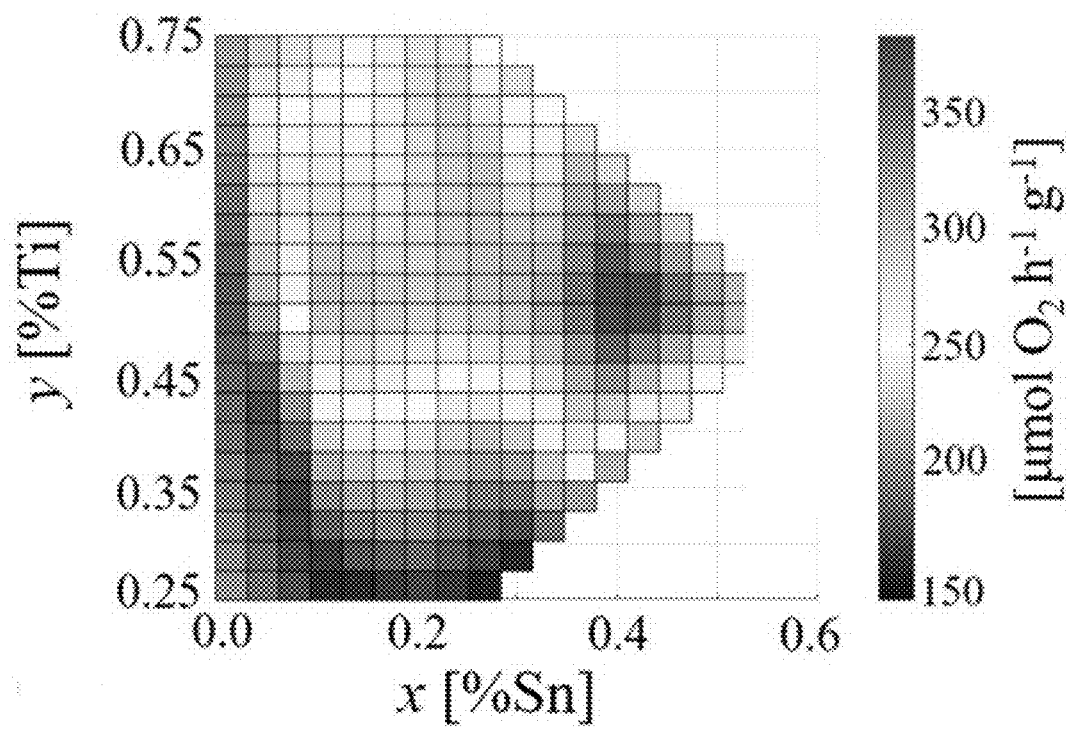
FIG. 21: Plot of photocatalytic rate of suspended particles of $(Ba_{1-x}Sn_x)(Zr_{1-y}Ti_y)O_3$, as a function of the Ba/Sn A-site (x-axis) and Zr/Ti B-site (y-axis) compositions, for molecular oxygen evolution (μmol $O_2$ $h^{-1}$ $g^{-1}$) under combined ultraviolet+visible light (λ>230 nm) irradiation. The blue to red coloring denotes higher photocatalytic rates.
Figure 22:
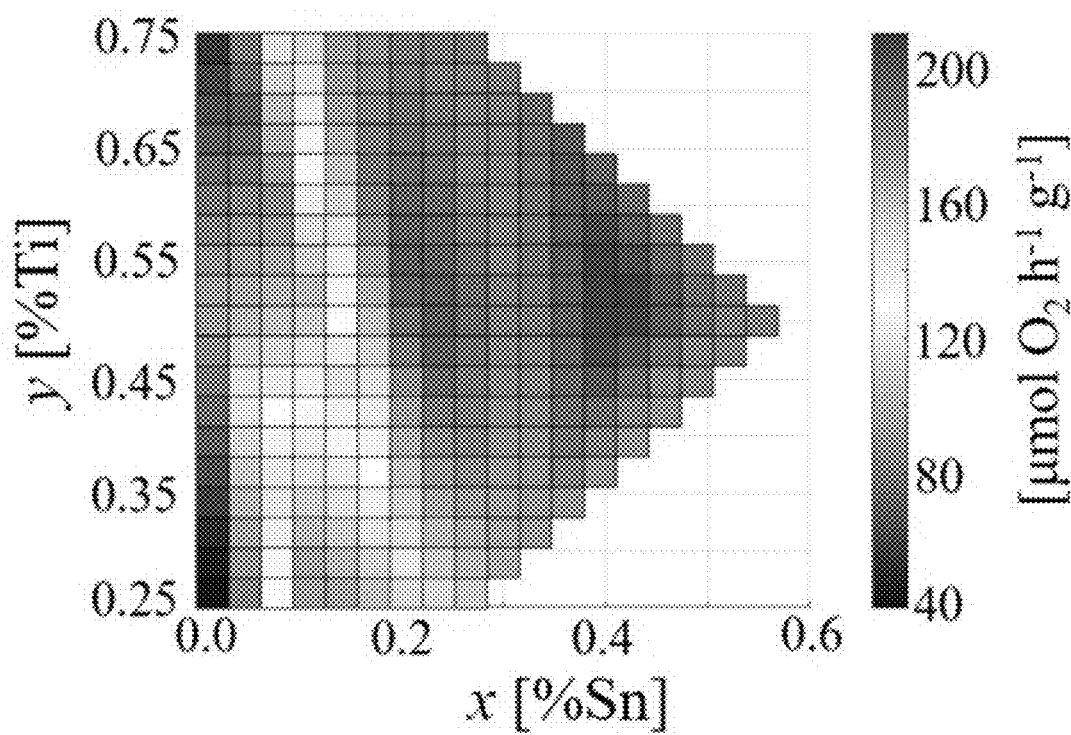
FIG. 22: Plot of photocatalytic rate of suspended particles of $(Ba_{1-x}Sn_x)(Zr_{1-y}Ti_y)O_3$, as a function of the Ba/Sn A-site (x-axis) and Zr/Ti B-site (y-axis) compositions, for molecular oxygen evolution (μmol $O_2$ $h^{-1}$ $g^{-1}$) under only visible-light irradiation (λ>400 nm). The blue to red coloring denotes higher photocatalytic rates.
Figure 23:
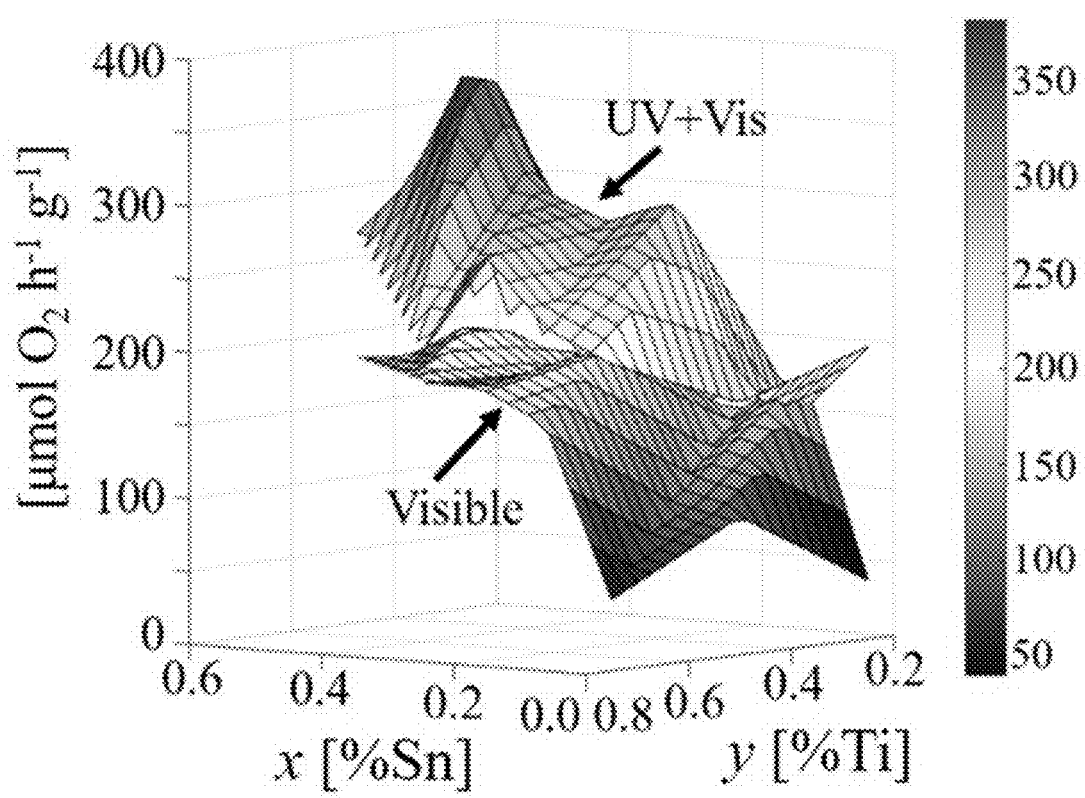
FIG. 23: Plots of photocatalytic rates of suspended particles of $(Ba_{1-x}Sn_x)(Zr_{1-y}Ti_y)O_3$, as a function of the Ba/Sn A-site (x-axis) and Zr/Ti B-site (y-axis) compositions, for molecular oxygen evolution (μmol $O_2$ $h^{-1}$ $g^{-1}$) under combined ultraviolet+visible light (λ>230 nm) (FIG. 21) and under only visible-light irradiation (λ>400 nm) (FIG. 22) plotted together. The blue to red coloring denotes higher photocatalytic rates.
Figure 25:
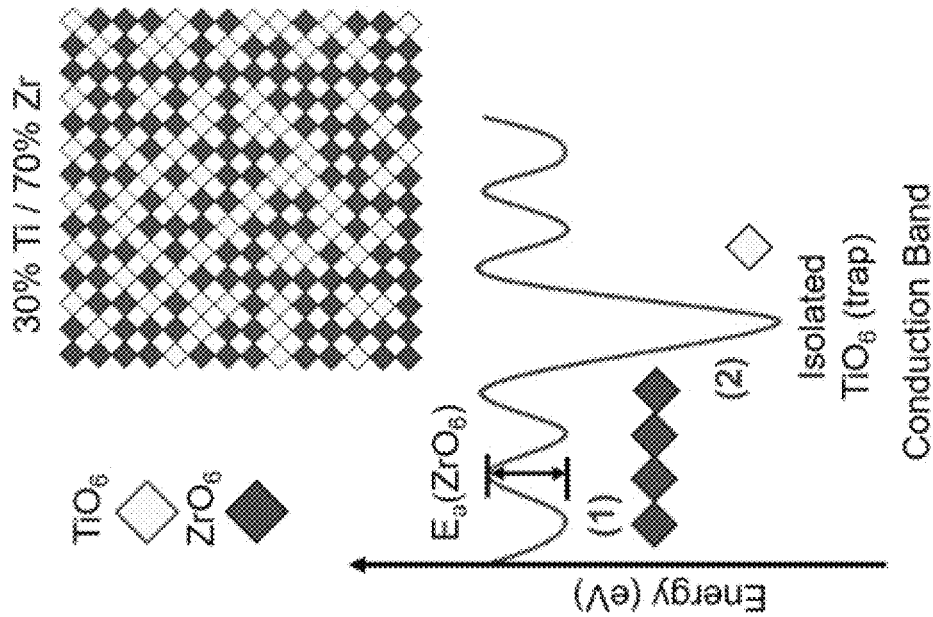
FIG. 25. Schematic illustration of a $TiO_6/ZrO_6$ solid solution, red and white squares respectively, wherein the $TiO_6$ octahedra are mixed at a concentration below the percolation threshold. The energy diagram (lower) show the polaron hopping with activation barriers ($E_a$) between the $ZrO_6$ or $TiO_6$ octahedra.
Figure 24:
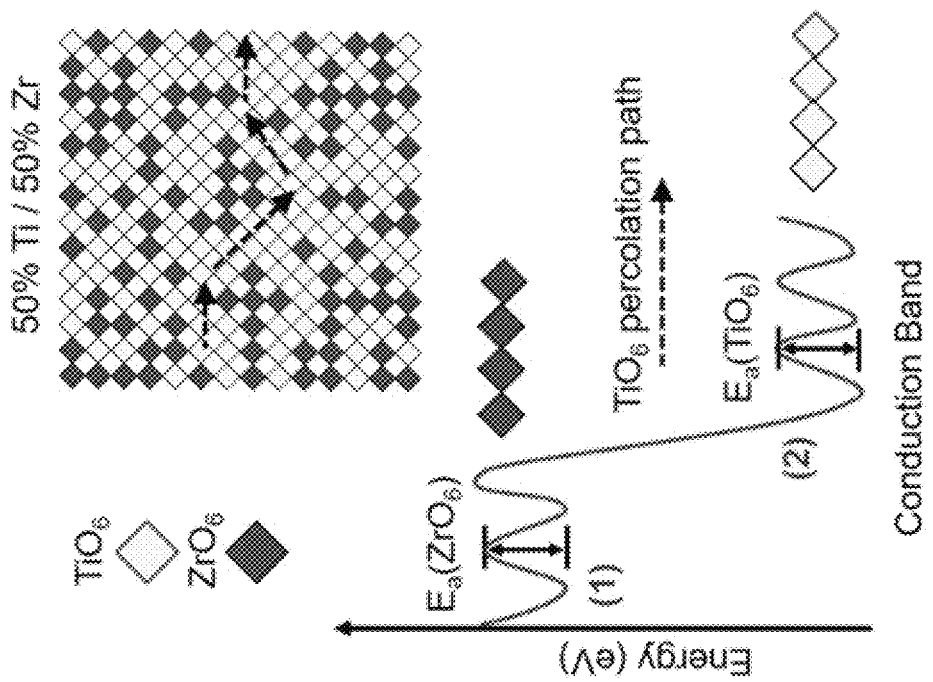
FIG. 24. Schematic illustration of a $TiO_6/ZrO_6$ solid solution, red and white squares respectively, wherein the $TiO_6$ octahedra are mixed at a concentration above the percolation threshold. The energy diagram (lower) shows the polaron hopping with activation barriers ($E_a$) between the $ZrO_6$ or $TiO_6$ octahedra.
Figure 26:
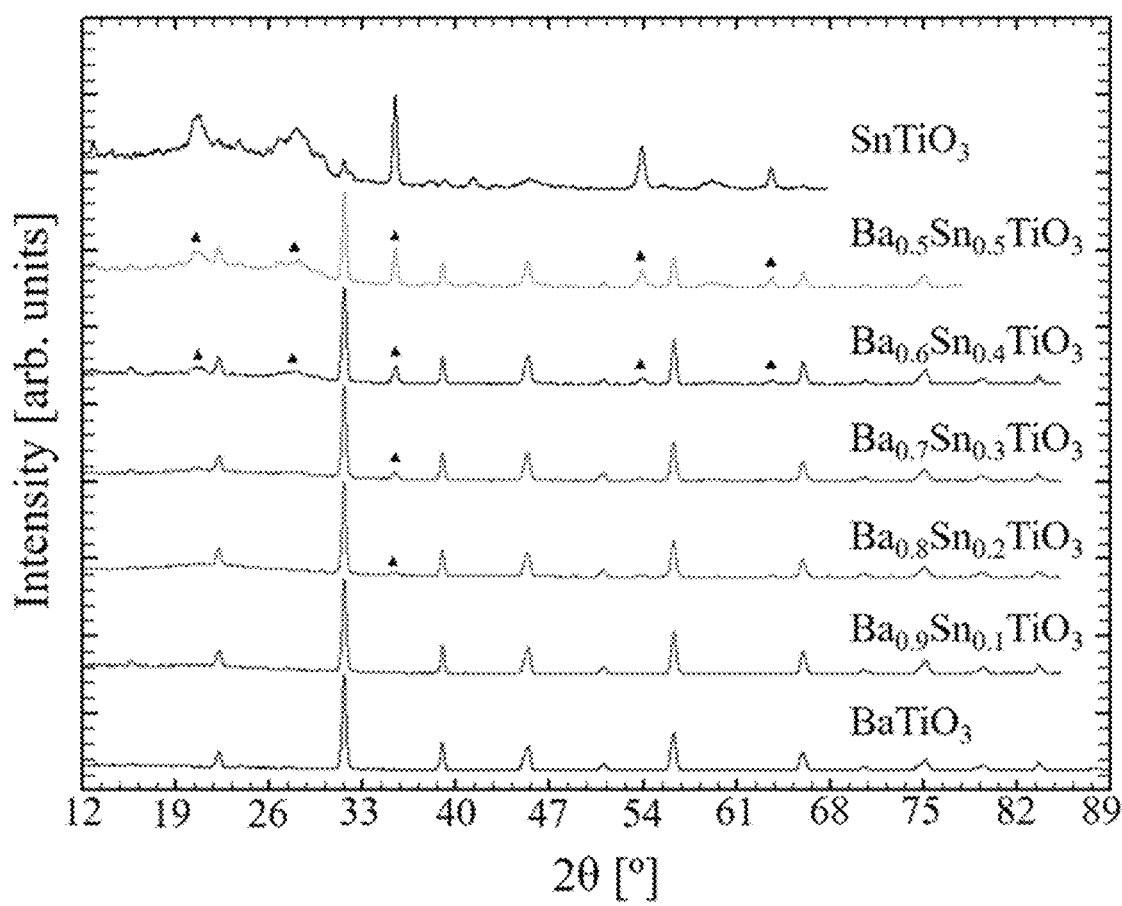
FIG. 26. PXRD for $Ba_{1-x}Sn_xTiO_3$ series (▲-ilmenite-type $SnTiO_3$). $BaTiO_3$ has a tetragonal P4MM perovskite structure while, $SnTiO_3$ crystallizes in an ilmenite-type structure (R3-).
Figure 27:
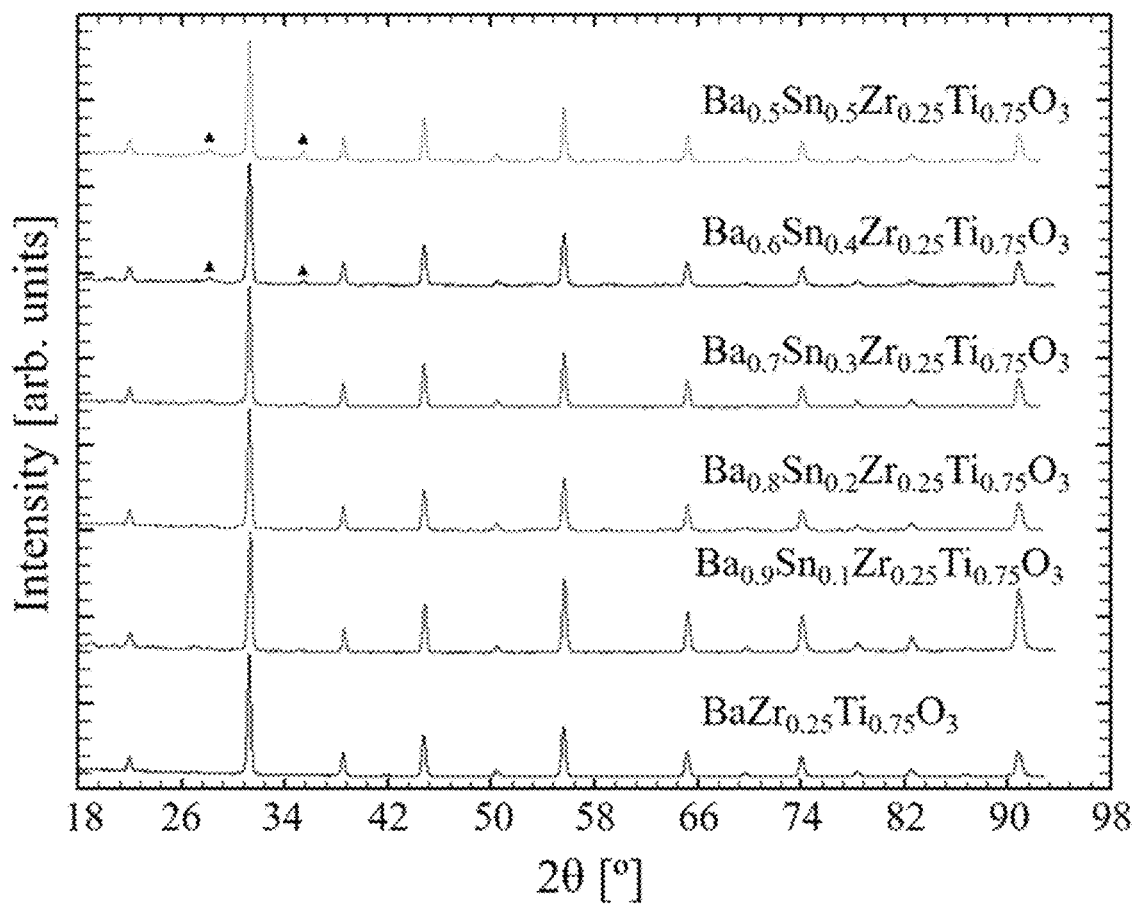
FIG. 27. PXRD of $Ba_{1-x}Sn_xZr_{0.25}Ti_{0.75}O_3$ series (▲-ilmenite-type $SnTiO_3$).
Figure 28:
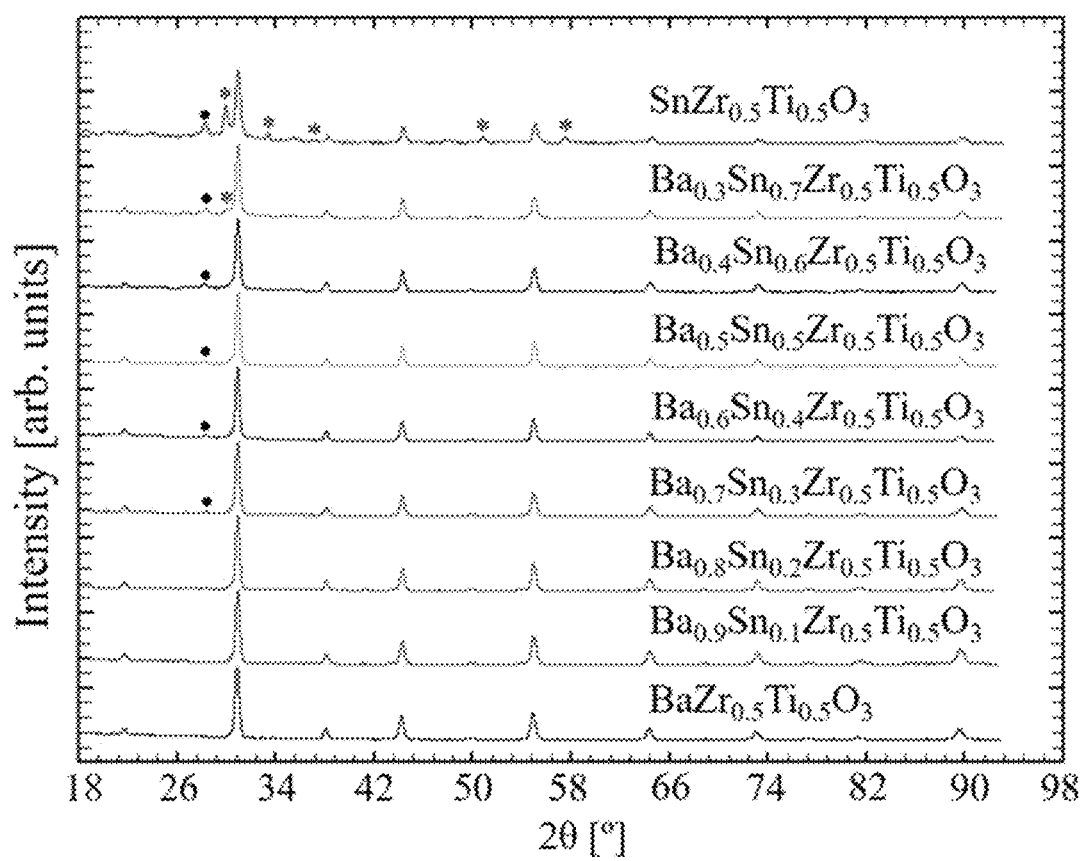
FIG. 28. PXRD for $Ba_{1-x}Sn_xZr_{0.5}Ti_{0.5}O_3$ series (•—$ZrO_2$, *—SnO)
Figure 29:
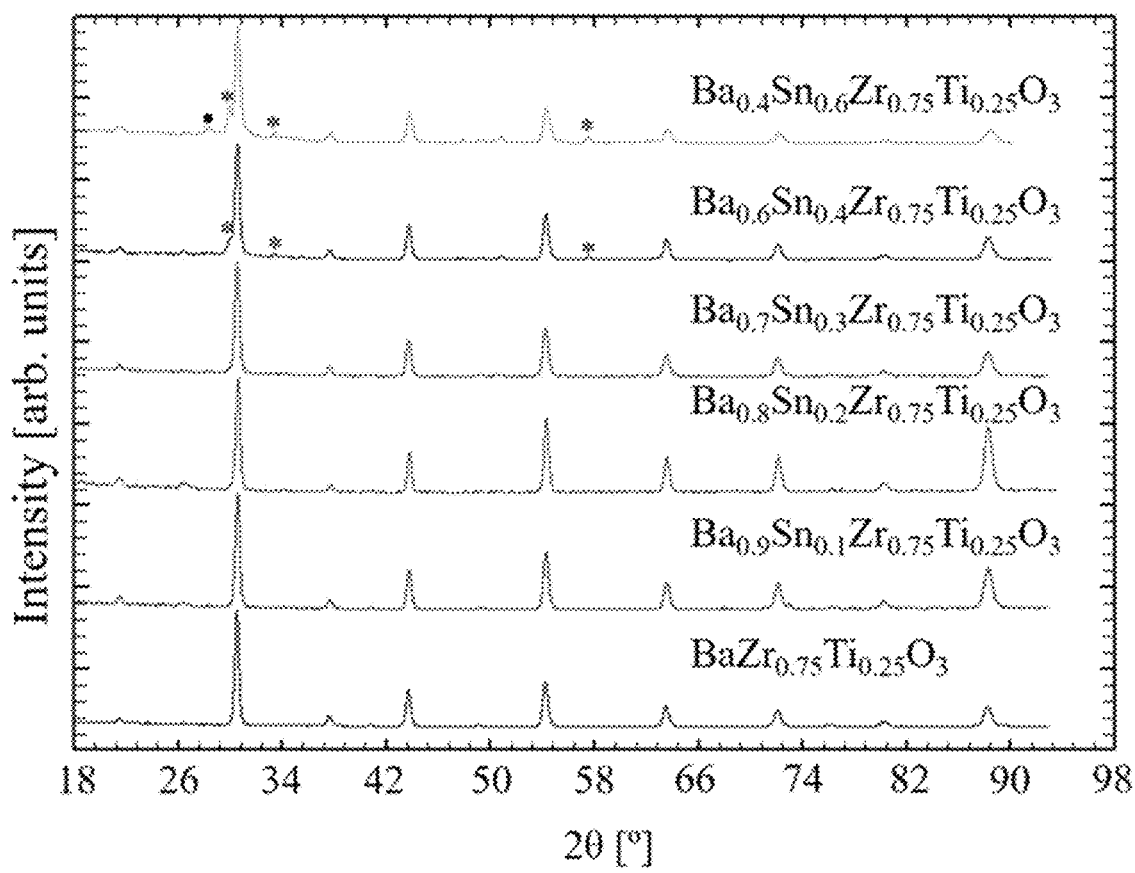
FIG. 29. PXRD for $Ba_{1-x}Sn_xZr_{0.75}Ti_{0.25}O_3$ series (•—$ZrO_2$, *—SnO).
Figure 30:
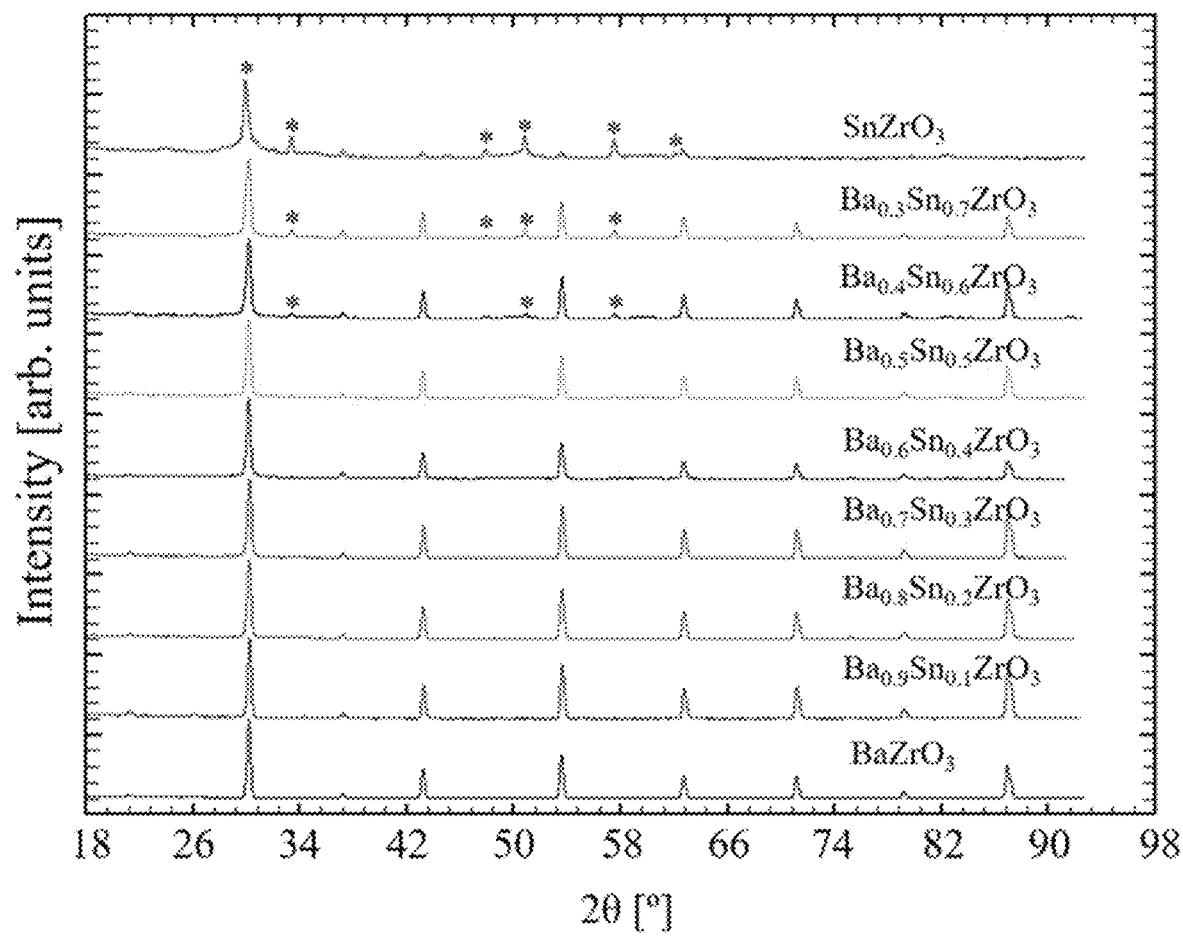
FIG. 30. PXRD for the $Ba_{1-x}Sn_xZrO_3$ series (*—SnO).

The Sn(II)-containing BSZT compositions all showed similar high photocatalytic rates for molecular oxygen production under visible-light irradiation, FIG. 22, while there was a detectable peaking in the rates at x=0.4 and y=0.5 under combined ultraviolet-visible irradiation, FIG. 21. In this case the electrons are excited across the band gap into a range of relatively lower to higher energies within the conduction band. As the conduction band is composed of a disordered distribution of the empty d-orbitals of the Ti(IV) and Zr(IV) cations, it might be assumed that a significant amount of local trapping of the excited electrons could predominate. Recent results have suggested that photocatalytic activities can peak beyond the percolation threshold of disordered solid solutions (Zoellner et al. *Inorg. Chem.* 2019, 58, 6845), whereby extended diffusion pathways 'open up' across the extended crystalline structure at specific compositions. The percolation threshold is defined by the concentration at which the charged carriers are no longer trapped in isolated, low-energy defects, but instead coalesce to form a new band with an accompanying delocalization of excited carriers (Kirkpatrick. *Rev. Mod. Phys.* 1973, 45, 574). An example of a two-dimensional percolation network is shown schematically in FIG. 24-FIG. 25 for a mixed $TiO_6/ZrO_6$ solid solution where the octahedra have 4-fold connectivity. The percolation pathways form the conduction band edge, owing to the lower-energy Ti d-orbitals relative to the Zr d-orbitals. For a two-dimensional network, the percolation threshold is reached at 50% Ti(IV) substitution, shown as white squares in FIG. 24, while it is not reached for only 30% Ti(IV) substitution, FIG. 25. For the former, the thermalization of the excited charge carriers to the band edges thus leads to delocalization throughout the percolation network, such as reported previously for the Nb(V)/Ta(V) cation solid solution (Zoellner et al. *Inorg. Chem.* 2019, 58, 6845). Similarly, the holes will thermalize to the valence band edge composed of Sn-5 s and O-2p based states and will become delocalized at Sn(II) concentrations that exceed the percolation threshold.

The percolation thresholds for both the A-site (Ba/Sn) and B-site (Ti/Zr) cations, $P_a$ and $P_b$, respectively, can be calculated to within a few percent for the three-dimensional cubic perovskite structure using the equation by Shante and Kirkpatrick (Shante et al. *Adv. Phys.* 1971, 20(85), 325-357):

$$z \times p_c = \frac{d}{d-1}$$

where z is the coordination number, $p_c$ is the percolation threshold, and d is the lattice dimensionality. The percolation threshold is the minimum concentration of a cation to form a complete path of adjacent sites, i.e., —O—Ti—O—Ti—O— or —O—Sn—O—Sn—O—, extending to the particles' surfaces. For the A-site Sn(II) cations, with 12-fold coordination and a dimensionality of 3, the percolation threshold corresponds to a $p_c(Sn)$ of only ~12.5%, and for the B-site Ti(IV) cations (z=6, d=3) this occurs at a $p_c(Ti)$ of ~25%. Thus, all compositions with >12.5% Sn(II) cations have extended —O—Sn—O—Sn—O connectivity for diffusion pathways of the charge carriers to reach the surfaces. This Sn(II) concentration represents the threshold at which higher visible-light activity is observed across the entire range of BSZT compositions, as found in the red-shaded region in FIG. 22, consistent with the relationship between percolation theory, charge-carrier delocalization, and photocatalytic activity. For the conduction band states, all compositions with >25% Ti(IV) cations have extended —O—Ti—O—Ti—O connectivity to provide percolation pathways for excited electrons. This is consistent with the much lower ultraviolet-visible photocatalytic rates for all perovskites with 25% or less Ti(IV) cations, as found in the blue-colored regions of FIG. 21. In this compositional region, the conduction electrons are more localized and have a higher probability for recombination rather than reaching the particles' surfaces to drive water oxidation. In the combined ultraviolet-visible photocatalytic data, FIG. 21, the peak in the highest photocatalytic rates is found for compositions with →25% Ti(IV) cations and >20% Sn(II) cations. This peak occurs under irradiation conditions where charge separation and diffusion have a major impact on photocatalytic rates, rather than simply a result of the smaller band gaps.

It is notable that the photocatalytic rates and apparent quantum yields of the BSZT perovskites are comparable to those initially reported for what is currently the best oxygen-evolving photocatalyst, i.e., $BiVO_4$ of ~100 μmol $O_2$ $h^{-1}g^{-1}$ and an AQY=0.3% (Kato et al. *Chem. Lett.* 2004, 33, 1348-1349). However, the bandgap sizes of the BSZT perovskites are smaller than $BiVO_4$ by about −0.4 to 0.5 eV and can absorb a larger fraction of sunlight. Accordingly, optimization of photocatalytic reaction conditions, including surface cocatalysts and film processing of the BSZT phases, can provide higher attainable rates and AQY's.

CONCLUSIONS

Flux-assisted reaction conditions were used to synthesize the highest known amounts of Sn(II) cations in a perovskite, $(Ba_{1-x}Sn_x)(Zr_{1-y}Ti_y)O_3$, consisting of mixed A-site Sn(II)/Ba(II) cations and B-site Ti(IV)/Zr(IV) cations in a statistically disordered distribution. The highest attainable Sn(II) substitutions were found for the Zr(IV)-richer compositions, of up to ~60% Sn(II) in $(Ba_{0.4}Sn_{0.6})(Zr_{0.5}Ti_{0.5})O_3$ or ~50-60% Sn(II) in $(Ba_{0.4}Sn_{0.6})ZrO_3$. These represented the most metastable perovskites that could be synthesized, with remarkably high reaction energies for decomposition of ~0.25 to 0.27 eV atom$^{-1}$. Their synthesizability is shown to be possible via the large cohesive energy of the underlying perovskite structure that limits the diffusion of ions required for decomposition to simpler oxides. The optical bandgap size decreased from ~3.90 eV to ~1.95 eV with higher Sn(II) and Ti(IV) compositions, in correlation with the compositions showing the highest metastability. The BSZT powders exhibited high photocatalytic rates under ultraviolet-visible or visible-light irradiation for molecular oxygen evolution that peaked at ~408 µmol $O_2$ $h^{-1}g^{-1}$ and ~216 µmol $O_2$ $h^{-1}g^{-1}$, respectively, for the $(Ba_{0.6}Sn_{0.4})(Zr_{0.5}Ti_{0.5})O_3$ composition. The highest rates were found for compositions that exceeded the percolation threshold for the A-site Sn(II) cations and the B-site Ti(IV) cations. These results demonstrate a route to highly metastable perovskites in order to target their smaller optical band gaps and favorable photocatalytic properties.

Figure 54:
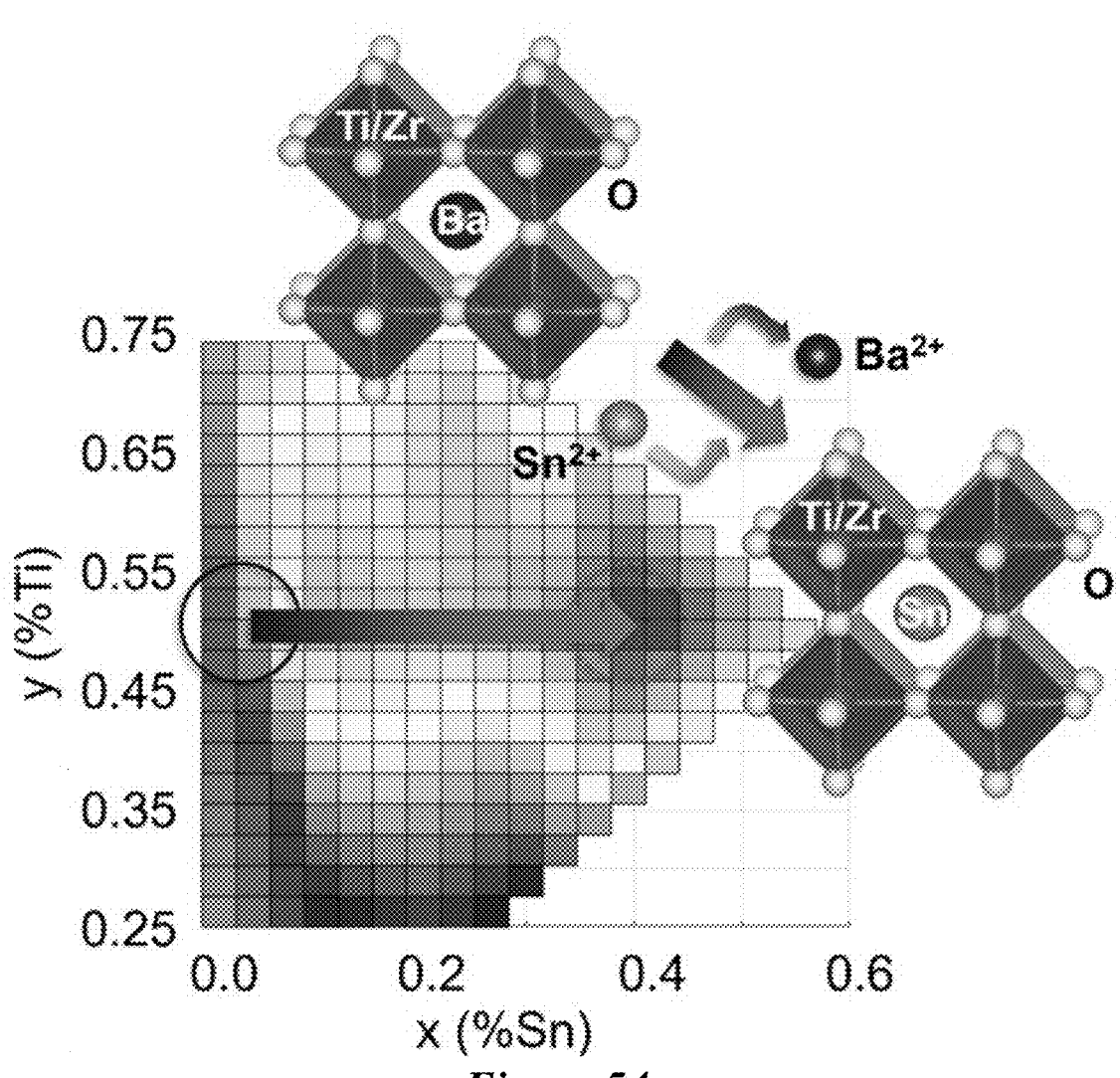
FIG. 54. Photocatalytic rates of $(Ba_{1-x}Sn_x)(Zr_{1-y}Ti_y)O_3$ as a function of the Ba/Sn A-site (x-axis) and Zr/Ti B-site (y-axis) compositions, for molecular oxygen evolution. The highest photocatalytic activities are found with increasing metastability and Sn(II) substitution, as highlighted in the diagram upon crossing from the blue to the red shaded regions.

The synthesizability of metastable semiconductors were explored herein, yielding a rich system of small bandgap photocatalysts for water oxidation. The highest photocatalytic activities are found with increasing metastability and Sn(II) substitution, as highlighted in FIG. 54 upon crossing from the blue to the red shaded regions.

Example 2—Production of Lead-Free Piezoelectric Ceramics and Applications in Electronic Devices One of the most widely used ceramics in the electronics industry is lead zirconate titanate, known as ferroelectric PZT, which shows a strong piezoelectric effect. This material contains over 60% highly toxic lead by weight and can cause significant safety issues during its processing and use, as lead is volatile and easily released into the environment. In the manufacturing and use of PZT, lead exposure can come from direct contact as well as from its release into the soil, drinking water, and air. This problem has been broadly recognized in a number of large industries that utilize this material as a piezoelectric component. Regulating federal agencies around the world have been placing increasingly stringent restrictions on the use of lead in commercial products and in manufacturing processes. The toxicity of PZT also hinders important in vivo uses, such as in piezoelectric-powered pacemakers and biocompatible sensors (Lu et al. Scientific Reports, 2015, 5, 16065), as lead can slowly dissolve into a subject's bloodstream. Lead is also one of the most common toxic elements found at Superfund sites. While the increasing use of PZT represents a dangerous and growing concern, it also continues to be mass produced and utilized in a plethora of products because there are currently no suitable replacements for it.

A solution to this problem is the replacement of the lead content of PZT with an equivalent, but far less toxic element, via a low-temperature chemical reaction. This reaction replaces toxic lead with tin, which has a significantly less toxic profile. For example, the tin content of inorganic compounds is poorly absorbed with usually very low buildup in the body. It also shows little to no evidence for being carcinogenic or mutagenic. The tin-based version of PZT, otherwise known as SZT, has been forecasted to show equivalent or superior piezoelectric properties and to be an ideal replacement. Thus, a chemical process to prepare SZT has been highly sought after in industry and academia, but with no prior success.

Described herein is a low-temperature process that exchanges lead for tin within PZT, resulting in lead-free SZT while retaining the same chemical structure as PZT. This chemical reaction occurs in inexpensive and nontoxic solvents and occurs with an ion exchange that switches out the lead for tin at near room temperature. These processing conditions are favorable as compared to the significantly higher processing temperatures of >1,000° C. needed to make PZT. The method described herein is currently the only known method that can prepare SZT material. Furthermore, the method described herein can be used to replace lead from existing raw feedstocks of PZT.

A wide range of PZT-based industries is impacted by lead toxicity and requires lead-free electronic substitutes. The lead-containing PZT piezoelectrics are the basis for a multitude of applications that include power sources, sensors, actuators, motors, and photovoltaics. For example, lead-containing piezoelectrics are used in ultrasound, electric lighters, microphones, fuses, guitar pickups, inkjet printers, loudspeakers, laser electronics among a multitude of many current device applications and markets. The market size for piezoelectrics is predicted to grow from ~$23.54 billion (in 2016) per year to ~$31.33 billion per year, by the year 2022. In particular, there is a rising demand for lead-free piezoelectrics in the automobile industry for uses in motors and actuators, and which currently represents the second largest market for PZT ceramics. Across all industries worldwide, the manufacture of lead-containing piezoelectrics is on the order of 1,250 to 4,000 tons per year. This represents a growing field of companies that would benefit from supplying lead-free and environmentally benign replacements, as well as in utilizing new manufacturing processes that can remove lead from their current PZT raw materials.

Example 3

Lead-containing ferroelectrics, such as PZT, are well known and widely commercialized for their outstanding piezoelectric properties. Owing to the toxicity of lead, lead-free substitutes have been highly sought after in industry. Disclosed herein, a range of low-temperature reaction conditions have been discovered in order to produce lead-free ferroelectric materials that can be further developed, for example, as environmentally-benign multilayer ceramic capacitors and as piezoelectric transducers. The process involves replacing the toxic Pb(II) cation with the isoelectronic Sn(II) cation that can function in a very similar chemical role. The methods can produce of lead-free ferroelectric films and single crystals.

The methods and products thereof described herein are more environmentally friendly. The process described herein is performed at a relatively low temperature (e.g., from 50° C. to 250° C.), and uses inexpensive and nontoxic solvents. The methods described herein can be used to extract lead from existing materials used commercially.

The materials made using the methods described herein can be used as piezoelectrics. Piezoelectrics have many widespread commercial uses as actuators, sensors and transducers, high voltage and power sources, and in photovoltaics.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The methods of the appended claims are not limited in scope by the specific methods described herein, which are intended as illustrations of a few aspects of the claims and any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

What is claimed is:

1. A perovskite material comprising:

$$[A_{1-x}Sn_x][Zr_{1-y}Ti_y]O_3$$

where:
A is Ba or Pb;
when A is Ba, then:
  x is from 0.1 to less than 1; and
  y is 0, 0.25, 0.5, or 0.75;
when A is Pb, then;
  x is from greater than 0 to less than 1; and
  y is from 0 to less than 1.

2. The perovskite material of claim 1, wherein the perovskite material comprises $[Ba_{1-x}Sn_x][Zr_{1-y}Ti_y]O_3$.

3. The perovskite material of claim 1, wherein the perovskite material comprises $Ba_{0.8}Sn_{0.2}Zr_{0.25}Ti_{0.75}O_3$, $Ba_{0.8}Sn_{0.2}Zr_{0.5}Ti_{0.5}O_3$, $Ba_{0.6}Sn_{0.4}Zr_{0.5}Ti_{0.5}O_3$, $Ba_{0.4}Sn_{0.6}Zr_{0.5}Ti_{0.5}O_3$, $Ba_{0.8}Sn_{0.2}Zr_{0.75}Ti_{0.25}O_3$, $Ba_{0.8}Sn_{0.2}ZrO_3$, $Ba_{0.6}Sn_{0.4}ZrO_3$, or a combination thereof.

4. The perovskite material of claim 1, wherein the perovskite material comprises $[Pb_{1-x}Sn_x][Zr_{1-y}Ti_y]O_3$.

5. The perovskite material of claim 1, wherein the perovskite material is metastable.

6. The perovskite material of claim 1, wherein the perovskite material is ferroelectric.

7. The perovskite material of claim 1, wherein the perovskite material comprises a semiconductor with a bandgap that overlaps with at least a portion of the solar spectrum.

8. The perovskite material of claim 1, wherein the perovskite material is biocompatible.

9. A method of making a perovskite material, the method comprising a peritectic flux reaction between a preliminary perovskite material and a Sn(II)-halide salt, thereby making a perovskite material comprising:

$$[A_{1-x}Sn_x][B_{1-y}B'_y]O_3$$

where:
A, if present, is selected from the group consisting of Li, Na, K, Rb, Cs, Be, Mg, Ca, Sr, Ba, Sc, Y, La, Ag, Cd, Tl, Pb, Ce, Pr, Nd, Pm, Sm, Eu, Gd, Tb, Dy, Ho, Er, Tm, Yb, Lu, or a combination thereof;
B and B', if present, are independently selected from the group consisting of Al, Sc, Ti, V, Cr, Mn, Fe, Co, Ni, Cu, Zn, Ga, Ge, Y, Zr, Nb, Mo, Ru, Rh, Pd, Ag, Cd, In, Sn, Sb, Te, La, Hf, Ta, W, Re, Os, Ir, Pt, Au, Bi, or a combination thereof;
x is from greater than 0 to 1; and
y is from 0 to 1;
with the proviso that A and B are different, A and B' are different, and B and B' are different.

10. The method of claim 9, wherein the method comprises contacting a preliminary perovskite comprising $A[B_{1-y}B'_y]O_3$ with a Sn(II)-halide salt comprising $SnCl_2$ and/or $SnF_2$.

11. The method of claim 9, wherein the preliminary perovskite comprises lead zirconate titanate (PZT).

12. The method of claim 9, wherein the perovskite material substantially excludes lead.

13. A method of converting a lead-containing perovskite to a lead-free perovskite by extracting the lead from the lead-containing perovskite by performing a peritectic flux reaction between the lead-containing perovskite and a Sn(II)-halide salt, wherein the lead-free perovskite material comprises:

$$[A_{1-x}Sn_x][B_{1-y}B'_y]O_3$$

where:
A, if present, is selected from the group consisting of Li, Na, K, Rb, Cs, Be, Mg, Ca, Sr, Ba, Sc, Y, La, Ag, Cd, Tl, Ce, Pr, Nd, Pm, Sm, Eu, Gd, Tb, Dy, Ho, Er, Tm, Yb, Lu, or a combination thereof;
B and B', if present, are independently selected from the group consisting of Al, Sc, Ti, V, Cr, Mn, Fe, Co, Ni, Cu, Zn, Ga, Ge, Y, Zr, Nb, Mo, Ru, Rh, Pd, Ag, Cd, In, Sn, Sb, Te, La, Hf, Ta, W, Re, Os, Ir, Pt, Au, Bi, or a combination thereof;
x is from greater than 0 to 1; and
y is from 0 to 1;
with the proviso that A and B are different, A and B' are different, and B and B' are different.

14. A method of use of the perovskite material of claim 1 as a photocatalyst for photocatalytic fuel generation, the perovskite material having a bandgap, wherein the method comprises contacting the photocatalyst with a fuel precursor to form a mixture and illuminating the mixture with light that overlaps with a least a portion of the bandgap of the perovskite material, thereby converting the fuel precursor to fuel.

15. The method of claim 14, wherein the fuel precursor comprises water or the fuel comprises hydrogen.

16. The method of claim 14, wherein the perovskite material exhibits a photocatalytic rate of from 100 µmol $O_2$ $h^{-1}$ $g^{-1}$ to 5000 µmol $O_2$ $h^{-1}$ $g^{-1}$ under electromagnetic irradiation at one or more wavelengths from 230 nm to 1023 nm.

17. A device comprising the perovskite material of claim 1.

18. The device of claim 17, wherein the device comprises a biocompatible sensor.

19. The device of claim 17, wherein the device comprises a piezoelectric device.

* * * * *